United States Patent
Ladner et al.

(10) Patent No.: US 9,114,144 B2
(45) Date of Patent: *Aug. 25, 2015

(54) KALLIKREIN-INHIBITOR THERAPIES

(75) Inventors: Robert C. Ladner, Ijamsville, MD (US); Arthur C. Ley, Newton, MA (US); Shirish Hirani, Arlington, MA (US); Anthony Williams, Melrose, MA (US); Maria Grazia De Simoni, Milan (IT); Luigi Bergamaschini, Milan (IT)

(73) Assignee: Dyax Corp., Burlington, MA (US)

( * ) Notice: Subject to any disclaimer, the term of this patent is extended or adjusted under 35 U.S.C. 154(b) by 481 days.

This patent is subject to a terminal disclaimer.

(21) Appl. No.: 13/228,300

(22) Filed: Sep. 8, 2011

(65) Prior Publication Data

US 2012/0015881 A1    Jan. 19, 2012

Related U.S. Application Data

(63) Continuation of application No. 11/929,822, filed on Oct. 30, 2007, now Pat. No. 8,034,775, which is a continuation of application No. 11/466,979, filed on Aug. 24, 2006, now Pat. No. 7,704,949, which is a continuation of application No. 10/953,902, filed on Sep. 27, 2004, now Pat. No. 7,153,829, which is a continuation-in-part of application No. 10/456,986, filed on Jun. 6, 2003, now Pat. No. 7,064,107.

(60) Provisional application No. 60/387,239, filed on Jun. 7, 2002, provisional application No. 60/407,003, filed on Aug. 28, 2002.

(51) Int. Cl.
*A61K 38/16* (2006.01)
*A61P 43/00* (2006.01)
*A61K 38/57* (2006.01)

(52) U.S. Cl.
CPC ..................................... *A61K 38/57* (2013.01)

(58) Field of Classification Search
CPC . A61K 2300/00; A61K 38/57; A61K 31/195; A61K 38/00; C07K 14/47
See application file for complete search history.

(56) References Cited

U.S. PATENT DOCUMENTS

| | | |
|---|---|---|
| 3,682,776 A | 8/1972 | Grundmann et al. |
| 3,691,016 A | 9/1972 | Patel |
| 3,969,287 A | 7/1976 | Jaworek et al. |
| 4,118,481 A | 10/1978 | Schnabel et al. |
| 4,153,687 A | 5/1979 | Schnabel et al. |
| 4,179,337 A | 12/1979 | Davis et al. |
| 4,195,128 A | 3/1980 | Hildebrand et al. |
| 4,229,537 A | 10/1980 | Hodgins et al. |
| 4,247,642 A | 1/1981 | Hirohara et al. |
| 4,330,440 A | 5/1982 | Ayers et al. |
| 4,377,572 A | 3/1983 | Schwarz et al. |
| 4,399,216 A | 8/1983 | Axel et al. |
| 4,447,224 A | 5/1984 | Decant |
| 4,447,233 A | 5/1984 | Mayfield |
| 4,595,674 A | 6/1986 | Tschesche et al. |
| 4,609,725 A | 9/1986 | Brady et al. |
| 4,634,665 A | 1/1987 | Axel et al. |
| 4,657,893 A | 4/1987 | Krantz et al. |
| 4,845,242 A | 7/1989 | Powers et al. |
| 4,881,175 A | 11/1989 | Ladner |
| 4,931,385 A | 6/1990 | Block et al. |
| 4,946,778 A | 8/1990 | Ladner et al. |
| 4,966,852 A | 10/1990 | Wun et al. |
| 5,106,833 A | 4/1992 | Broze, Jr. et al. |
| 5,118,668 A | 6/1992 | Auerswald et al. |
| 5,166,133 A | 11/1992 | Houston et al. |
| 5,179,017 A | 1/1993 | Axel et al. |
| 5,212,091 A | 5/1993 | Diaz-Collier et al. |
| 5,223,409 A | 6/1993 | Ladner et al. |
| 5,260,203 A | 11/1993 | Ladner et al. |
| 5,278,144 A | 1/1994 | Wolf |
| 5,278,285 A | 1/1994 | Ebbers et al. |
| 5,312,736 A | 5/1994 | Rasmussen et al. |
| 5,372,933 A | 12/1994 | Zamarron et al. |
| 5,373,090 A | 12/1994 | Norris et al. |
| 5,378,614 A | 1/1995 | Petersen et al. |
| 5,407,915 A | 4/1995 | Fritz et al. |
| 5,409,895 A | 4/1995 | Morishita et al. |
| 5,426,224 A | 6/1995 | Lee et al. |
| 5,441,931 A | 8/1995 | Sprecher et al. |
| 5,444,156 A | 8/1995 | Veloso et al. |
| 5,446,090 A | 8/1995 | Harris |
| 5,455,338 A | 10/1995 | Sprecher et al. |
| 5,466,783 A | 11/1995 | Wun et al. |
| 5,563,123 A | 10/1996 | Innis et al. |
| 5,576,294 A | 11/1996 | Norris et al. |

(Continued)

FOREIGN PATENT DOCUMENTS

| | | |
|---|---|---|
| AT | 275583 T | 9/2004 |
| AT | E275583 T1 | 4/2005 |
| CA | 2180950 A1 | 8/1995 |
| DE | 69533472 T2 | 1/2006 |
| EP | 0132732 A2 | 2/1985 |

(Continued)

OTHER PUBLICATIONS

Attwood (Science 290: 471-473, 2000).*
Skolnick et al. (Trends in Biotech. 18: 34-39, 2000).*
International Search Report including Written Opinion from International Application No. PCT/08/73665 dated Feb. 5, 2008.
International Search Report including Written Opinion from International Application No. PCT/US08/74061 dated Dec. 28, 2008.

(Continued)

*Primary Examiner* — Sharon Wen
(74) *Attorney, Agent, or Firm* — Wolf, Greenfield & Sacks, P.C.

(57) ABSTRACT

Methods are described for preventing or reducing ischemia, e.g., cerebral ischemia, and/or reperfusion injury, e.g., reperfusion injury associated with cerebral ischemia, in a patient.

7 Claims, 9 Drawing Sheets

(56) References Cited

U.S. PATENT DOCUMENTS

| | | |
|---|---|---|
| 5,583,107 A | 12/1996 | Wolf et al. |
| 5,585,089 A | 12/1996 | Queen et al. |
| 5,589,359 A | 12/1996 | Innis et al. |
| 5,618,696 A | 4/1997 | Norris et al. |
| 5,629,176 A | 5/1997 | Bj.o slashed.rn et al. |
| 5,635,187 A | 6/1997 | Bathurst et al. |
| 5,648,331 A | 7/1997 | Koudsi et al. |
| 5,663,143 A | 9/1997 | Ley et al. |
| 5,672,662 A | 9/1997 | Harris et al. |
| 5,677,146 A | 10/1997 | Sprecher et al. |
| 5,693,761 A | 12/1997 | Queen et al. |
| 5,693,762 A | 12/1997 | Queen et al. |
| 5,695,760 A | 12/1997 | Faanes et al. |
| 5,696,088 A | 12/1997 | Innis et al. |
| 5,719,041 A | 2/1998 | Lazarus et al. |
| 5,736,364 A | 4/1998 | Kelley et al. |
| 5,739,208 A | 4/1998 | Harris |
| 5,747,449 A | 5/1998 | Lasters et al. |
| 5,770,568 A | 6/1998 | Auerswald et al. |
| 5,780,265 A | 7/1998 | Dennis et al. |
| 5,786,328 A | 7/1998 | Dennis et al. |
| 5,795,865 A | 8/1998 | Markland et al. |
| 5,795,954 A | 8/1998 | Lazarus et al. |
| 5,800,385 A | 9/1998 | Demopulos et al. |
| 5,804,376 A | 9/1998 | Braxton et al. |
| 5,824,870 A | 10/1998 | Baszczynski et al. |
| 5,834,244 A | 11/1998 | Dennis et al. |
| 5,843,895 A | 12/1998 | Lazarus et al. |
| 5,849,992 A | 12/1998 | Meade et al. |
| 5,853,723 A | 12/1998 | Jacobs et al. |
| 5,863,893 A | 1/1999 | Dennis et al. |
| 5,869,637 A | 2/1999 | Au-Young et al. |
| 5,874,407 A | 2/1999 | Kelley et al. |
| 5,880,256 A | 3/1999 | Dennis et al. |
| 5,900,461 A | 5/1999 | Harris |
| 5,914,316 A | 6/1999 | Brown et al. |
| 5,932,462 A | 8/1999 | Harris et al. |
| 5,951,974 A | 9/1999 | Gilbert et al. |
| 5,962,266 A | 10/1999 | White et al. |
| 5,990,237 A | 11/1999 | Bentley et al. |
| 5,994,125 A | 11/1999 | Markland et al. |
| 6,001,596 A | 12/1999 | Hillman et al. |
| 6,004,579 A | 12/1999 | Bathurst et al. |
| 6,008,196 A | 12/1999 | Curran et al. |
| 6,010,880 A | 1/2000 | Markland et al. |
| 6,013,448 A | 1/2000 | Braxton et al. |
| 6,013,763 A | 1/2000 | Braisted et al. |
| 6,017,723 A | 1/2000 | Rao et al. |
| 6,057,287 A | 5/2000 | Markland et al. |
| 6,063,764 A | 5/2000 | Creasey et al. |
| 6,071,723 A | 6/2000 | Markland et al. |
| 6,087,473 A | 7/2000 | Conklin et al. |
| 6,090,916 A | 7/2000 | Vlasuk et al. |
| 6,103,499 A | 8/2000 | Markland et al. |
| 6,103,500 A | 8/2000 | Innis et al. |
| 6,113,896 A | 9/2000 | Lazarus et al. |
| 6,126,933 A | 10/2000 | Warne et al. |
| 6,159,938 A | 12/2000 | Gyorkos et al. |
| 6,171,587 B1 | 1/2001 | Wun et al. |
| 6,174,721 B1 | 1/2001 | Innis et al. |
| 6,180,607 B1 | 1/2001 | Davies et al. |
| 6,214,966 B1 | 4/2001 | Harris |
| 6,242,414 B1 | 6/2001 | Johnson et al. |
| 6,258,351 B1 | 7/2001 | Harris |
| 6,261,279 B1 | 7/2001 | Demopulos et al. |
| 6,306,884 B1 | 10/2001 | Buckman et al. |
| 6,333,402 B1 | 12/2001 | Markland et al. |
| 6,348,558 B1 | 2/2002 | Harris et al. |
| 6,362,254 B2 | 3/2002 | Harris et al. |
| 6,362,276 B1 | 3/2002 | Harris et al. |
| 6,376,604 B2 | 4/2002 | Kozlowski |
| 6,407,213 B1 | 6/2002 | Carter et al. |
| 6,413,507 B1 | 7/2002 | Bentley et al. |
| 6,423,498 B1 | 7/2002 | Markland et al. |
| 6,432,397 B1 | 8/2002 | Harris |
| 6,455,639 B1 | 9/2002 | Yasukohchi et al. |
| 6,472,195 B2 | 10/2002 | Hillman et al. |
| 6,515,100 B2 | 2/2003 | Harris |
| 6,534,276 B1 | 3/2003 | Wun et al. |
| 6,548,262 B2 | 4/2003 | Gentz et al. |
| 6,576,235 B1 | 6/2003 | Williams et al. |
| 6,583,108 B1 | 6/2003 | Tamburini et al. |
| 6,610,281 B2 | 8/2003 | Harris |
| 6,624,246 B2 | 9/2003 | Kozlowski |
| 6,664,331 B2 | 12/2003 | Harris et al. |
| 6,689,582 B1 | 2/2004 | Davies et al. |
| 6,710,125 B2 | 3/2004 | Kozlowski |
| 6,774,180 B2 | 8/2004 | Kozlowski et al. |
| 6,783,960 B2 | 8/2004 | Innis et al. |
| 6,783,965 B1 | 8/2004 | Sherman et al. |
| 6,806,360 B2 | 10/2004 | Wun et al. |
| 6,814,982 B2 | 11/2004 | Poncin et al. |
| 6,914,135 B2 | 7/2005 | Sheppard et al. |
| 6,953,674 B2 | 10/2005 | Markland et al. |
| 6,989,369 B2 | 1/2006 | Ladner et al. |
| 7,064,107 B2 | 6/2006 | Ley et al. |
| 7,067,144 B2 | 6/2006 | Demopulos et al. |
| 7,078,383 B2 | 7/2006 | Ley et al. |
| 7,153,829 B2 | 12/2006 | Ladner et al. |
| 7,166,576 B2 | 1/2007 | Cicardi et al. |
| 7,235,530 B2 | 6/2007 | Blair et al. |
| 7,276,480 B1 | 10/2007 | Ladner et al. |
| 7,550,427 B2 | 6/2009 | Ley et al. |
| 7,628,983 B2 | 12/2009 | Markland et al. |
| 7,704,949 B2 | 4/2010 | Ladner et al. |
| 7,718,617 B2 | 5/2010 | Cicardi et al. |
| 7,811,991 B2 | 10/2010 | Ladner et al. |
| 7,851,442 B2 | 12/2010 | Ladner et al. |
| 7,919,462 B2 | 4/2011 | Markland et al. |
| 8,034,775 B2 | 10/2011 | Ladner et al. |
| 8,124,586 B2 | 2/2012 | Ladner et al. |
| 8,188,045 B2 | 5/2012 | Blair et al. |
| 8,283,321 B2 | 10/2012 | Markland et al. |
| 2001/0027180 A1 | 10/2001 | Isaacs |
| 2002/0102703 A1 | 8/2002 | Sheppard et al. |
| 2002/0111460 A1 | 8/2002 | Holloway |
| 2003/0012969 A1 | 1/2003 | Clark |
| 2003/0096733 A1 | 5/2003 | Ny et al. |
| 2003/0100070 A1 | 5/2003 | Holloway |
| 2003/0113726 A1 | 6/2003 | Tsuchihashi et al. |
| 2003/0114372 A1 | 6/2003 | White et al. |
| 2003/0153046 A1 | 8/2003 | Jensen et al. |
| 2003/0175919 A1 | 9/2003 | Ley et al. |
| 2003/0223977 A1 | 12/2003 | Ley et al. |
| 2004/0038893 A1 | 2/2004 | Ladner et al. |
| 2004/0044075 A1 | 3/2004 | Staveski et al. |
| 2004/0049018 A1 | 3/2004 | Bailon et al. |
| 2004/0053206 A1 | 3/2004 | Cicardi et al. |
| 2004/0062746 A1 | 4/2004 | Martinez et al. |
| 2004/0062748 A1 | 4/2004 | Martinez et al. |
| 2004/0106747 A1 | 6/2004 | Bailon et al. |
| 2004/0126361 A1 | 7/2004 | Saifer et al. |
| 2004/0152633 A1 | 8/2004 | Jorgensen et al. |
| 2004/0171794 A1 | 9/2004 | Ladner et al. |
| 2004/0180827 A1 | 9/2004 | Chen et al. |
| 2004/0209243 A1 | 10/2004 | Nixon et al. |
| 2005/0004021 A1 | 1/2005 | Sprecher et al. |
| 2005/0075665 A1 | 4/2005 | Brenzel et al. |
| 2005/0089515 A1 | 4/2005 | Ley et al. |
| 2005/0164928 A1 | 7/2005 | Ladner et al. |
| 2005/0164945 A1 | 7/2005 | Nixon et al. |
| 2005/0180977 A1 | 8/2005 | Nixon et al. |
| 2006/0069020 A1 | 3/2006 | Blair et al. |
| 2006/0194727 A1 | 8/2006 | Ladner et al. |
| 2006/0205671 A1 | 9/2006 | Vinten-Johansen |
| 2006/0228331 A1 | 10/2006 | Peschke et al. |
| 2006/0264603 A1 | 11/2006 | Markland et al. |
| 2007/0020252 A1 | 1/2007 | Ladner et al. |
| 2007/0041959 A1 | 2/2007 | Ley et al. |
| 2007/0049522 A1 | 3/2007 | Ladner et al. |
| 2007/0065407 A1 | 3/2007 | Patten et al. |
| 2007/0079096 A1 | 4/2007 | Chen |
| 2007/0100133 A1 | 5/2007 | Beals et al. |
| 2007/0117752 A1 | 5/2007 | Larsen et al. |

(56) References Cited

U.S. PATENT DOCUMENTS

| | | |
|---|---|---|
| 2007/0213275 A1 | 9/2007 | Clark et al. |
| 2007/0249807 A1 | 10/2007 | Ladner et al. |
| 2007/0253949 A1 | 11/2007 | Golz et al. |
| 2008/0031426 A1 | 2/2008 | Weeks |
| 2008/0038276 A1 | 2/2008 | Sinha et al. |
| 2008/0050716 A1 | 2/2008 | Cicardi et al. |
| 2008/0064637 A1 | 3/2008 | Ladner et al. |
| 2008/0076712 A1 | 3/2008 | Ladner et al. |
| 2008/0131426 A1 | 6/2008 | Ladner et al. |
| 2008/0139473 A1 | 6/2008 | Ladner et al. |
| 2008/0152656 A1 | 6/2008 | Ladner et al. |
| 2008/0182283 A1 | 7/2008 | Markland et al. |
| 2008/0188409 A1 | 8/2008 | Blair et al. |
| 2008/0200646 A1 | 8/2008 | Ladner et al. |
| 2008/0221031 A1 | 9/2008 | Blair et al. |
| 2008/0226655 A1 | 9/2008 | Ladner et al. |
| 2008/0255025 A1 | 10/2008 | Ladner |
| 2008/0260752 A1 | 10/2008 | Ladner et al. |
| 2008/0299050 A1 | 12/2008 | Bortz et al. |
| 2009/0023651 A1 | 1/2009 | Markland et al. |
| 2009/0062195 A1 | 3/2009 | Ladner et al. |
| 2009/0075887 A1 | 3/2009 | Mcpherson |
| 2009/0082267 A1 | 3/2009 | Ladner et al. |
| 2009/0105142 A1 | 4/2009 | Moscicki |
| 2009/0117130 A1 | 5/2009 | Ladner et al. |
| 2009/0123475 A9 | 5/2009 | Siegel |
| 2009/0215119 A1 | 8/2009 | Ladner |
| 2009/0221480 A1 | 9/2009 | Blair et al. |
| 2009/0227494 A1 | 9/2009 | Blair et al. |
| 2009/0227495 A1 | 9/2009 | Blair et al. |
| 2009/0233852 A1 | 9/2009 | Blair et al. |
| 2009/0234009 A1 | 9/2009 | Blair et al. |
| 2009/0247452 A1 | 10/2009 | Ellis et al. |
| 2009/0247453 A1 | 10/2009 | Blair et al. |
| 2009/0264350 A1 | 10/2009 | Blair et al. |
| 2010/0034805 A1 | 2/2010 | Ladner et al. |
| 2010/0183625 A1 | 7/2010 | Sternlicht |
| 2010/0273721 A1 | 10/2010 | Belichard |
| 2010/0286061 A1 | 11/2010 | Devy et al. |
| 2011/0008762 A1 | 1/2011 | Cicardi et al. |
| 2011/0086801 A1 | 4/2011 | Ladner et al. |
| 2011/0136746 A1 | 6/2011 | Markland et al. |
| 2011/0200611 A1 | 8/2011 | Sexton |
| 2012/0015881 A1 | 1/2012 | Ladner et al. |
| 2012/0201756 A1 | 8/2012 | Sexton |
| 2012/0328517 A1 | 12/2012 | Markland et al. |
| 2013/0012438 A1 | 1/2013 | Blair et al. |

FOREIGN PATENT DOCUMENTS

| | | |
|---|---|---|
| EP | 0255011 A2 | 2/1988 |
| EP | 0274826 A1 | 7/1988 |
| EP | 0285123 A2 | 10/1988 |
| EP | 301122 A1 | 2/1989 |
| EP | 0307592 A2 | 3/1989 |
| EP | 0318451 A2 | 5/1989 |
| EP | 0401508 A2 | 12/1990 |
| EP | 0486001 A1 | 5/1992 |
| EP | 0 401 508 B1 | 11/1994 |
| EP | 0621870 B1 | 5/1997 |
| EP | 0621871 B1 | 7/1997 |
| EP | 739355 B1 | 9/2004 |
| EP | 1484339 A2 | 12/2004 |
| JP | 7-504891 T | 6/1995 |
| JP | 9-059838 A | 3/1997 |
| JP | 9-511131 T | 11/1997 |
| JP | 10-503375 A | 3/1998 |
| JP | 2002-524076 A | 8/2002 |
| JP | 2002-543147 | 12/2002 |
| JP | 2009-511131 | 3/2009 |
| WO | 89/10374 A1 | 11/1989 |
| WO | 9002809 A1 | 3/1990 |
| WO | 92/06111 A1 | 4/1992 |
| WO | 93/09233 A2 | 5/1993 |
| WO | 93/14120 A1 | 7/1993 |
| WO | 93/14121 A1 | 7/1993 |
| WO | 93/14122 A1 | 7/1993 |
| WO | 9314120 A1 | 7/1993 |
| WO | 9314121 A1 | 7/1993 |
| WO | 9314122 A1 | 7/1993 |
| WO | 95/18830 A2 | 7/1995 |
| WO | 95/21601 A2 | 8/1995 |
| WO | 9521601 A2 | 8/1995 |
| WO | 95/23860 A3 | 9/1995 |
| WO | WO-96/04377 A1 | 2/1996 |
| WO | 96/04378 A3 | 3/1996 |
| WO | 9620278 A2 | 7/1996 |
| WO | 96/35788 A2 | 11/1996 |
| WO | WO-96/35788 A2 | 11/1996 |
| WO | 9733996 A2 | 9/1997 |
| WO | 98/52976 A1 | 11/1998 |
| WO | 9963090 A2 | 12/1999 |
| WO | WO-99/63090 A1 | 12/1999 |
| WO | 00/14235 A1 | 3/2000 |
| WO | 00/34317 A2 | 6/2000 |
| WO | 019968 A1 | 2/2001 |
| WO | 0114424 A2 | 3/2001 |
| WO | 0168707 A1 | 9/2001 |
| WO | 0179480 A1 | 10/2001 |
| WO | 0206334 A1 | 1/2002 |
| WO | 0206539 A1 | 1/2002 |
| WO | 02092147 A2 | 11/2002 |
| WO | 02094200 A2 | 11/2002 |
| WO | 03006860 A1 | 1/2003 |
| WO | 03066824 A2 | 8/2003 |
| WO | WO-03/066824 A1 | 8/2003 |
| WO | 03/103475 A2 | 12/2003 |
| WO | 2004/019968 A1 | 3/2004 |
| WO | 2004/062646 A1 | 7/2004 |
| WO | 2004/062689 A1 | 7/2004 |
| WO | WO-2004/062657 A | 7/2004 |
| WO | 2005/021557 A2 | 3/2005 |
| WO | 2005021556 A2 | 3/2005 |
| WO | 2005021557 A2 | 3/2005 |
| WO | WO-2005/0021556 | 3/2005 |
| WO | 2005/075665 A2 | 8/2005 |
| WO | 2006/017538 A2 | 2/2006 |
| WO | 2006036860 A2 | 4/2006 |
| WO | 2006/066878 A1 | 6/2006 |
| WO | 2006/089005 A2 | 8/2006 |
| WO | 2007079096 A2 | 7/2007 |
| WO | 2007106746 A2 | 9/2007 |
| WO | 2008000833 A1 | 1/2008 |
| WO | 2009/026334 A2 | 2/2009 |
| WO | 2009026539 A1 | 2/2009 |
| WO | 2009/102927 A1 | 8/2009 |
| WO | 2010003475 A2 | 1/2010 |
| WO | 2010006746 A2 | 1/2010 |
| WO | 2011/085103 A2 | 7/2011 |
| WO | 2012/094587 A1 | 7/2012 |

OTHER PUBLICATIONS

International Search Report of International Application No. PCT/US06/49322 mailed Dec. 7, 2007.

Kanppik et al., "Fully synthetic human combinatorial antibody libraries (HuCAL) based on modular consensus frameworks and CDRs randomized with trinucleotides", J. Mol. Biol. 296:57-86 (2000).

Kaplan, et. al., "A Prealbumin Activator of Preallirrein. 3. Appearance of Chemotactic Activity for Human Neutrophils by the conversion of Human Prekallikrein", J. Exp. Med. vol. 135(1), p. 81-97; p. 92 Fig 10, p. 93 (1972).

Katre et al., "Chemical modification of recombinant interleukin 2 by polyethylene glycol increases its potency in the murine Meth A sarcoma model," PNAS USA, 1987, vol. 84, pp. 1487-1491.

Katre et al., "Immunogenicity of recombinant IL-2 modified by covalent attachment of polyethylene glycol," J. Immunol., 1990, vol. 144, pp. 209-213.

Kaufman, et al., "Amplification and expression of sequences cotransfected with a modular dihydrofolate reductase complementary dna gene", Mol. Biol. 159:601 621 (1982).

(56) References Cited

OTHER PUBLICATIONS

Kelly et al., "Diabetes insipidus in uricase-deficient mice: a model for evaluating therapy with poly(ethylene glycol)—modified," J. Am. Soc. Nephrol., 2001, vol. 12, pp. 1001-1009.

Kemp et al., "Synthesis of Peptide-Functionalized Daicylaminoepinodolidiones," Tetrahedron Letters, 29:5077-5080 (1988).

Kido et al., "Kunitz-type protease inhibitor found in rat mast cells," The Journal of Biological Chemistry, 1988, vol. 263, No. 34, pp. 18104-18107.

Kido et al., "Protease Specificity of Kunitz Inhibitor Domain of Alzheimer's Disease Amyloid Protein Precursor," Biochemical and Biophysical Research Communications, 167:716-721 (1990).

Kirchhofer et al., "Hepsin activates pro-hepatocyte growth factor and is inhibited by hepatocyte growth factor activator-1B (HAI-1B) and HAI-2," FEBS Letters, 2005, vol. 579, pp. 1945-1950.

Kirchhoff, et al., "A Major Human Epididymis-Specific cDNA Encodes a Protein with Sequence Homology to Extracellular Proteinase Inhibitors," Biology of Reproduction, 45:350-357 (1991).

Kline, et al., "Hirulog Peptides with Scissile Bond Replacements Resistant to Thrombin Cleavage," Biochem. Biophys. Res. Comm., 177:1049-1055 (1991).

Kuno et al., "Possible involvement of neutrophil elastase in impaired mucosal repair in patients with ulcerative colitis," Journal of Gastroenterology, 2002, vol. 37, Supple XIV, pp. 22-32.

Kurjan & Herskowitz, "Structure of a Yeast Pheremone Gene (MFα): A putative α-Factor Precursor Contains Four Tandem Copies of Mature α-Factor," Cell, 30: 933-943 (1982).

Laskowski, et al., "Inhibitors with Class-Specific Reactive Sites," Ann. Rev. Biochem., 49:593-626 (1980).

Leatherbarrow, et al., "Design of a Small Peptide-Based Proteinase Inhibitor by Modeling the Active-Site Region of Barley Chymotrypsin Inhibitor 2," Biochemistry, 30:10717-10721 (1991).

Leeb-Lundberg et al. "International union of pharmacology. XLV. Classification of the kinin receptor family: from molecular mechanisms to pathophysiological consequences", (2005) Pharmacol Rev 57, 27-77.

Leonetti et al., "Increasing immunogenicity of antigens fused to Ig-binding proteins by cell surface targeting," The Journal of Immunology, 1998, vol. 160, pp. 3820-3827.

Levy Jerrold H et al: "The therapeutic potential of a kallikrein inhibitor for treating hereditary angioedema.", Expert Opinion on Investigational Drugs Sep. 2006 LNKD-PUBMED:16916274,vol. 15, No. 9, Sep. 2006, pp. 1077-1090.

Ley et al., "Obtaining a Family of High-Affinity, High Specificity Protein Inhibitors of Plasmin and Plasma Kallikrein," Molecular Diversity, 2:119-124, (1996).

Lilla et al., "Active plasma kallikrein localizes to mast cells and regulates epithelial cell apoptosis, adipocyte differentiation, and stromal remodeling during mammary gland involution" J Biol Chem. 284(20):13792-13803 (2009).

Lohmann, et al., Plasmin- and Plasminogen-Activator Inhibitors after Excimer Laser Photorefractive Keratectomy: New Concept in Prevention of Postoperative Myopic Regression and Haze, Refractive and Corneal Surgery, 9:300-302, (1993).

Longa et al., "Reversible middle cerebral artery occlusion without craniectomy in rats" Stroke 20 (1): 84-91 (1989).

Lucas, et al., "The Binding of Human Plasminogen to Fibrin and Fibrinogen," J. Biol. Chem., 258:4249-4256 (1983).

Lumry et al, Interim Results of EDEMA2, a Multicenter, Open-Label, Repeat-Dosing Study of Intravenous and Subcutaneous Administration of Ecallantide (DX-88) in Hereditary Angioedema. J. Allergy and Clinical Immunology 117(2)(Suppl. 1):S179 Abstract 699 (2006).

MacGilchrist, "Effect of the Serine Protease Inhibitor, Aprotinin, on Systemic Haemodynamics and Renal Function in Patients with Hepatic Cirrhosis and Ascites," Clin. Sci., 87:329-335 (1994).

Magklara et al., "Characterization of the enzymatic activity of human kallikrein 6: autoactivation, substrate specificity and regulation by inhibitors," Biochem. Biophys. Res. Commun., Aug. 8, 2003, vol. 307, No. 4, pp. 948-955, Abstract Only.

Mann et al., Hemostasis and Thrombosis, Chapter 10, 2nd Edition, Basic Principles and Clinical Practice: 148-161 (1987).

Mannucci, "Hemostatic Drugs" New England Journal of Medicine, Drug Therapy, 339(4):245-253 (1998).

March, Advanced Organic Chemistry, 3rd Edition, Reactions, Mechanisms, and Structure, John Wiley and Sons, New York: 396-398; 1057-1060; 1099-1100 (1985).

Markland et al., "Iterative Optimization of High-Affinity Protease Inhibitors Using Phage Display. 1. Plasmin," Biochemistry, 35:8045-8057 (1996).

Markland et al., "Iterative Optimization of High-Affinity Protease Inhibitors Using Phage Display. 2. Plasma Kallikrein and Thrombin," Biochemistry 35(24):8058-67 (1996).

Markland et al., "Selection for Protease Inhibitors Using Bacteriophage Display," Methods Enzymol., 267:28-51 (1996).

Mathews, et al., Biochemistry, The Benjamin Cummins Publishing Co., Inc. Redwood City CA: 208-212 (1990).

Mattheakis et al. "An in vitro polysome display system for identifying ligands from very large peptide libraries" Proc. Natl. Acad. Sci. USA 91:9022 (1994).

Maxfield et al., "Conformation of poly(ethylene oxide) in the solid state, melt and solution measured by Raman scattering," Polymer, 1975, vol. 16, pp. 505-509.

McCarty, "Crystal-induced inflammation of the joints," Annual Reviews of Medicine, vol. 21, pp. 357-366 (1970).

McConnell et al., "New Leupeptin Analogues: Synthesis and Inhibition Data," J. Med. Chem., 33:86-93 (1990).

Merriam-Webster reference for the term "prevent." web date: 2010. 2 pages.

Merrifield, "Solid Phase Peptide Synthesis. I. The Synthesis of a Tetrapeptide," Am. Chem. Soc. 85:2149-2154 (1963).

Mine et al., "Structural mechanism for heparin-binding of the third Kunitz domain of human tissue factor pathway inhibitor," Biochemistry, 2002, vol. 41, pp. 78-85.

Miyajima, et al., Secretion of Mature Mouse Interleukin-2 by *Saccharomyces cerevisiae*: Use of a General Secretion vector Containing Promoter and Leader Sequences of the Mating Pheromone a-factor, Gene, 37:155-161 (1985).

Molineux, "Pegylation: engineering improved pharmaceuticals for enhanced therapy," Cancer Treatment Reviews, 2002, vol. 28, pp. 13-16.

Monteseirin, et al., "Plasma Kallikrein Amidolytic Activity in Bronchial Asthma," Allergol. Immunopathol., (Madr)., 20:211-214 (1992).

Moreland, "Intra-articular hyaluronan (hyaluronic acid) and hylans for the treatment of osteoarthritis: mechanisms of action," Arthritis Res. Ther, 2003, vol. 5, pp. 54-67.

Abuchowski et al., "Alteration of immunological properties of bovine serum albumin by covalent attachment of polyethylene glycol," J. Bio. Chem., 1977, vol. 252, pp. 3578-3581.

Abuchowski et al., "Cancer therapy with chemically modified enzymers, I., Antitumor properties of polyethylene glycol-asparaginase conjugates," Cancer Biochem. Biophys., 1984, vol. 7, pp. 175-186.

Abuchowski et al., "Effect of covalent attachment of polyethylene glycol on immunogenicity and circulating life of bovine," J. Biol. Chem., 1977, vol. 252, pp. 3582-3586.

Adams et al: "The role of viscosupplementation with hylan G-F 20 (Synvisc(R)) in the treatment of osteoarthritis of the knee: a Canadian multicenter trial comparing hylan G-F 20 alone, hylan G-F 20 with non-steroidal anti-inflammatory drugs (NSAIDs) and NSAIDs alone", Osteoarthritis and Cartilage, Bailliere Tindall, London, GB, vol. 3, No. 4, pp. 213-225, (Dec. 1, 1995).

Adelman, et al., Proteolysis of Platelet Glycoprotein Ib by Plasmin Is Facilitated by Plasmin Lysine-Binding Regions, Blood, vol. 68 (6): 1280-1284, (Dec. 1986).

(56) References Cited

OTHER PUBLICATIONS

Alberto Migliore et al: "Open pilot study of ultrasound-guided intra-articular injection of hylan G-F 20 (Synvisc) in the treatment of symptomatic hip osteoarthritis", Clinical Rheumatology; Journal of the International League of Associations for Rheumatology, Springer-Verlag, LO, vol. 24, No. 3, pp. 285-289 (Jun. 1, 2005).
Albrecht, et al., Kunitz-Type Proteinase Inhibitors Derived by Limited Proteolysis of the Inter-α-Trypsin Inhibitors From several Mammalian Sera, Hoppe-Seyler's Z. Physiol. Chem., vol. 364: 1703-1708, (Dec. 1983).
Albrecht, et al.., Elastase Inhibition by the Inter-α-Trypsin Inhibitor and Derived Inhibitors of Man and Cattle, Hoppe-Seyler's Z. Physiol. Chem., vol. 364: 1697-1702, (Dec. 1983).
Anba, et al., Improving the Stability of a Foreign Protein in the Periplasmic Space of *Escherichia coli*, Biochimie, vol. 70(6): 727-733, (1988).
Angliker, et al., The Synthesis of Lysylflouromethanes and their Properties as Inhibitors of Trypsin, Plasmin and Cathepsin B, Biochemistry, 241:871-875, (1987).
Appendix A—alignment of SEQ ID No. 23 (DX-890) and SEQ ID No. 12 (IT102), 1 page, Jun. 27, 2007.
Asano M. et al., "Effects of a nonpeptide bradykinin B2 receptor antagonist, FR167344, on different in vivo animal models of inflammation", Br J Pharmacol, vol. 122, p. 1436-1440 (1997).Asano M. et al., Br J Pharmacol, vol. 122, p. 1436-1440 (1997).
Atherton, et al., Peptide Synthesis. Part 2. Procedures for Solid Phase Synthesis using Nα-Fluorenylmethycarbonylamino-acids on Polyamide Supports. Synthesis of Substance P and of Acyl Carrier Protein 65-74 Decapeptide, J. Chem. Soc. Perkins Trans, 1:538-546, (1981).
Attwood, The Babel of Bioinformatics; Science, vol. 290, pp. 471-473 (2000).
Auerswald et al., Expression, Isolation and Characterization of Recombinant [Arg15, Glu52] Aprotinin, Bio. Chem. Hoppe-Seyler, 369:(Suppl)27-35 (1988).
Baba, M et al., States of Tyrosyl Residues and Circular Dichroism of Kunitz Trypsin Inhibitor, J. Biochem 65 (1):113-121 (1969).
Balduyck, et al., Human Urinary Proteinase Inhibitor: Inhibitory Properties and Interaction with Bovine Trypsin, Bio. Chem. Hoppe-Seyler, vol. 366: 9-14, (1985).
Baneyx et al., Construction and Characterization of *Escherichia coli* Strains Deficient in Multiple Secreted Proteases: Protease III Degrades High-Molecular-Weight Substrates In Vivo, J Bacteriol., 173:2696-2703 (1991).
Baneyx et al., "In Vivo Degradation of Secreted Fusion Proteins by the *Escherichia coli* Outer Membrane Protease OmpT", J. Bacteriol., 172:491-494, (1990).
Basu et al., "Structure-function engineering of interferon-b-1b for improving stability, solubility, potency, immunogenicity, and pharmacokinetic properties by site-selective mono-PEGylation," Bioconjugate Chemistry, 2006, vol. 17, pp. 618-630.
Bayes et al., "Gateways to Clinical Trials" Methods Find Exp. Clin. Pharmacol., vol. 28(3): pp. 185-206 (2006).
Beckmann et al., "Preparation of chemically 'mutated' aprotinin homologues by semisynthesis-P1 substitutions change inhibitory specificity," Eur. J. Biochem., vol. 176, pp. 675-682 (1988).
Berge, S.M., et al., "Pharmaceutical salts", J. Pharm. Sci. 66:1-19 (1977).
Bergthorsdottir et al., "Signals that initiate somatic hypermutation of B cell in vitro", J. Immunol., p. 166:2228 (2001).
Berndt, et al.,"Designed Replacement of an Internal Hydration Water Molecule in BPTI: Structural and Functional Implications of a Glycine-to-Serine Mutation," Biochemistry, 32: 4564-4570 (1993).
Bhoola et al., "Bioregulation of Kinins: Kallikreins, Kininogens and Kininases," Pharmacological Reviews, 44 :1-80 (1992).
Blaber et al., "Targeting kallikrein 6-proteolysis attenuates CNS inflammatory disease," The FASEB Journal, express article published online Mar. 19, 2004.

Blijlevens et al: "Palifermin (recombinant keratinocyte growth factor-1): a pleiotropic growth factor with multiple biological activities in preventing chemotherapy- and radiotherapy-induced mucositis", Annals of Oncology, vol. 18, No. 5, Jan. 1, 2007, pp. 817-826.
Bork, "Powers and pitfalls in sequence analysis: the 70% hurdle," Genome Research, vol. 10, pp. 398-400 (2000).
Borregaard et al., "Granules of the human neutrophilic polymorphonuclear leukocyte," Blood, 1997, vol. 89, No. 10, pp. 3503-3521.
Bowdish K, et. al., "Yeast expression of a catalytic antibody with chorismate mutase activity.", J Biol Chem.; 266 (18):11901-8 (Jun. 25, 1991).
Branden et al., "Prediction, Engineering, and Design of Protein," Introduction to Protein Structure, 1991, pp. 247, Garland Publishing Inc., New York.
Brenner, "Errors in genome annotation," Trends in Genetics, vol. 15, No. 4, pp. 132-133 (1999).
Brinkmann et al., "Design of an aprotinin variant with inhibitory activity against chymotrypsin and cathepsin G by recombinant DNA technology," Biol. Chem. Hoppe-Seyler, vol. 371, pp. 43-52 (1990).
Browne et al., "Expression of Recombinant Human Plasminogen and Aglycoplasminogen in HeLa Cells," Genebank, Accession No. M74220 (1991).
Broze et al., "Regulation of Coagulation by a Multivalent Kunitz-Type Inhibitor," Biochemistry, 29:7539-7546, (1990).
Brus et al., "Disease Severity Is Correlated with Plasma Clotting and Fibrinolytic and Kinin-Kallikrein Activity in Neonatal Respiratory Distress Syndrome," Pediatric Research, 41:120-127, (1997).
Buchan et al., "A new model of temporary focal neocortical ischemia in the rat", Stroke 23 (2): 273-9 (1992).
Budavari, ed., Merck index, 11th ed., ISBN 911910-28-X, entries 923, 1745, 2740, 7425, (1989).
Burrage et al., "Matrix metalloproteinases: role in arthritis," Fronteirs in Bioscience, 2006, vol. 11, pp. 529-543.
Cantor et al., "Elastin and elastases in lung disease," 1989, Chapter 16, vol. II, pp. 159-168.
Carey et al., Advanced Organic Chemistry, 3rd Edition, Part B: Reactions and Synthesis, Plenum Press, New York: 678-686 (1990).
Carmichael, "Rodent models of focal stroke: size, mechanism, and purpose", NeuroRx 2: 396-409 (2005).
Carpenter et al., "Rational design of stable lyophilized protein formulations: theory and practice," Parmaceutical Biotechnology, vol. 13, pp. 109-133 (2002).
Casati et al., "Cardiopulmonary support and physiology—tranexamic acid compared with high-dose aprotinin in primary elective heart operations: effects on perioperative bleeding and allogeneic transfusions," The Journal of Thoracic and Cardiovascular Surgery, vol. 120, pp. 520-527 (2000).
Cassim et al., "Kallikrein cascade and cytokines in inflamed joints," Pharmacology and Therapeutics, 2002, vol. 94, pp. 1-34.
Cernak, "Animal models of head trauma", NeuroRx. 2(3): 410-422 (2005).
Chen et al., "A model of focal ischemic stroke in the rat: reproducible extensive cortical infarction", Stroke 17 (4): 738-43 (1986).
Chen et al., "Establishment of an animal model of oral mucositis induced by conditioning regimen of haematopoietic stem cell transplantation" Zhonghua Kou Qiang Yi Xue Za Zhi. 42(11):672-6 (2007). (Abstract only).
Quanta Biodesign, Labeling, Derivatization and Crosslinking Reagents for Biological and Related Materials with dPEGTM, pp. 1-38, Mar. 12, 2004.
Quanta Biodesign, Labeling, Modification and Crosslinking Reagents incorporating our unique monodispersed dPEGTM, pp. 1-31, Nov. 5, 2004.
Quanta Biodesign, Leading innovator, producer and provider of monodisperse descrete PEGTM (dPEGTM) derivatives, Product Catalogue, pp. 1-51, Updated: Jul. 18, 2005.
Quanta Biodesign, Leading innovator, producer and provider of monodisperse discrete PEGTM (dPEGTM) derivatives, Product Catalogue, pp. 1-51, Updated: Nov. 17, 2005.

(56) References Cited

OTHER PUBLICATIONS

Rahman et al., "Identification and functional importance of plasma kallikrein in the synovial fluids of patients with rheumatoid, psoriatic, and osteoarthritis," Annals of the Rheumatic Diseases, vol. 54, pp. 345-350 (1995).
Reichert, "Technology evaluation: lumiliximab, Biogen Idec" Curr Opin Mol Ther., 6(6):675-83 (2004). (Abstract only).
Robbins, K.C. et al., Hemostasis and Thrombosis, Chapter 21, 2nd Edition, Basic Principles and Clinical Practice: 340-357 (1987).
Roberts et al., "Directed evolution of a protein: seleciton of potent neurtophil elastase inhibitor displayed on M13 fusion phage," PNAS USA, vol. 89, pp. 2429-2433 (1992).
Roberts et al., "Protease inhibitor display M13 phage: selection of high-affinity neurtophil elastase inhibitors," Gene, vol. 121, pp. 9-15 (1992).
Roberts, M.J. et al., "Chemistry for peptide and protein PEGylation", Advanced Drug Delivery Reviews, 54, pp. 459-476, 2002.
Rossi, E. et al., The Synthetic Peptide DX88 Binds to Endothelial Cells In Vitro and Retains the Inhibitory Activity on Kallikrein, International Immunopharmacology 2(9):1313, Abstract 142 (2002).
Sainz I.M. et al., "Fifty years of research on the plasma kallikrein-kinin system: from protein structure and function to cell biology and in-vivo pathophysiology" Thromb Haemost 98, 77-83, 2007.
Sartor, R.B., et al., "Selective Kallikrein-Kinin System Activation in Inbred Rats Differentially Susceptible to Granulomatous Enterocolitis," Gastroenterology, 110:1467-1481 (1996).
Scarff et al., "Targeted disruption of SP13/Serpinb6 does not result in development of growth defects, leukocyte dysfunction, or susceptibility to stroke," Molecular and Cellular Biology, May 2004, pp. 4075-4082.
Scatchard, George, The Attractions of Proteins for Small Molecules and Ions, Ann. NY Acad. Sci, 51:660-672 (1949).
Schechter et al, On the Active Site of Proteases, III Mapping the Active Site of Papain; Specific Peptide Inhibitors of Papain, Biochemical and Biophysical Research Communications 32(5):898-902 (1968).
Schechter et al., On the Size of the Active Site on Proteases, I Papain, Biochemical and Biophysical Research Communications 27(2):157-162 (1967).
Schmaier A.H. "Assembly, activation, and physiologic influence of the plasma kallikrein/kinin system" (2008) Int Immunopharmacol8, 161-165.
Schmaier et al., Hemostasis and Thrombosis, Chapter 2, 2nd Edition, Basic Principals and Clinical Practice: 18-38 (1987).
Schmid-Elsaesser, et al., "A critical reevaluation of the intraluminal thread model of focal cerebral ischemia: evidence of inadvertent premature reperfusion and subarachnoid hemorrhage in rats by laser-Doppler flowmetry" Stroke 29 (10): 2162-70 (1989).
Schmidt et al., "A male accessory gland peptide with protease inhibitory activity in *Drosophila funebris*," Swiss-Prot, Accession #P11424 (1992).
Schnabel et al., Aprotinin: Preparation by Partial Desulphurization of Aprotinin by Means of Raney Nickel and Comparison with Other Aprotinin Derivatives, Biol. Chem. Hoppe-Seyler, 367:1167-1176 (1986).
Schoonooghe, et. al., "Efficient production of human bivalent and trivalent anti-MUC1 Fab-scFv antibodies in *Pichia pastoris*", BMC Biotechnol. Aug. 11, 2009;9:70.
Schopf, "IDEC-114 (IDEC)" Curr Opin Investig Drugs, 2(5):635-8 (2001). (Abstact only).
Schwartz et al., "Stability studies on derivatives of the bovine trypsin inhibitor," Biochemistry, vol. 26, pp. 3544-3551 (1987).
Shearwater Corporation, Polyethylene Glycol and Derivatives for Biomedical Applications, pp. 1-17, catalogue—2001.
Shearwater Polymers, Inc., Polyethylene Glycol and Derivatives, pp. 1-50, catalogue—Jul. 1997.
Shearwater Polymers, Inc., Polyethylene Glycol Derivatives: Functionalized Biocompatible Polymers for Research and Pharmaceuticals, pp. 1-50, catalogue—2000.
Shearwater Polymers, Inc., pp. 2-49, catalogue—Mar. 1995.

Sheppard, et al., Acid-Labile Resin Linkage Agents for Use in Solid Phase Peptide Synthesis, Int. J. Peptide Protein Res., 20:451-454 (1982).
Sheridan, et al., A Multicenter Trial of the Use of the Proteolytic Enzyme Inhibitor Aprotinin in Colorectal Surgery, Dis. Colon Rectum, 32:505-508 (1989).
Sherman et al., "Chapter 11: Conjugation of high-molecular weight poly(ethylene glycol) to cytokinds: granulocyte-macrophage colony-stimulating factors as model substrates," American Chemical Society, 1997, pp. 155-169.
Shibuya, et. al., "Primary Structure of Guinea Pig Plasma Prekallikrein", Immunopharmacology, vol. 45 (1-3), p. 127-34, Abstract p. 131, Fig 1, 2 (1999).
Siebeck et al., "Inhibition of plasma kallikrein with aprotinin in porcine endotoxin shock," J. Trauma, vol. 34, pp. 193-198 (1993).
Skolnick et al., "From genes to protein structure and function: novel applications of computational apporaches in the genomic era," Trends in Biotech., 2000, vol. 18, No. 1, pp. 34-39.
Sonis et al. "An animal model for mucositis induced by cancer chemotherapy" (1990) Oral Surg Oral Med Oral Pathol. 69:437-43.
Sonis et al. "Validation of a new scoring system for the assessment of clinical trial research of oral mucositis induced by radiation or chemotherapy. Mucositis Study Group." (1999) Cancer 85:2103-13.
Sprecher et al., "Molecular cloning, expression, and partial characterization of a second human tissue-factor-pathway inhibitor," PNAS USA, 1994, vol. 91, No. 8, pp. 3353-3357.
Sprecher et al., "Molecular Cloning, Expression, and Partial Characterization of a Second Human Tissue-Factor-Pathway Inhibitor," Proc. Natl. Acad. Sci. USA, 91:3353-3357 (1994).
Stadnicki et al., "Activation of plasma contact and coagulation systems and neutrophils in the active phase of ulcerative colitis," Digestive Diseases and Sciences, 1997, vol. 42, No. 1, pp. 2356-2366.
Stadnicki et al., "Activation of the Kallikrein-Kinin System in Indomethacin-Induced Entercolitis in Genetically Susceptible Rats," J. Invest. Med., 44:299A (1996).
Stadnicki et al., "Selective Plasma Kallikrein Inhibitor Attenuates Acute Intestinal Inflammation in Lewis Rat," Dig. Dis. Sci., 41:912-920 (1996).
Sunkureddi et al., "Clinical signs of gout," Hospital Physician, 2006, pp. 39-41.
Supplementary European Search Report from European Application No. 8798232 dated Feb. 1, 2012.
Supplemental European Search Report and Search Opinion from European Application No. 3791557.6 dated Oct. 19, 2007.
Supplemental European Search Report and Search Opinion from European Application No. 7758271.6 dated Jun. 18, 2010.
Supplemental European Search Report from EP App. No. 04786615.7 dated Jan. 20, 2009.
Supplementary Euopean Search Report dated Jan. 19, 2009 from EP App. No. 04782687.0.
Supplementary European Search Report from European Application No. 3757339.1 dated Apr. 23, 2008.
Chen et al., "Refined 2-5 A X-ray Crystal Structure of the Complex Formed by Porcine Kallikrein A and the Bovine Pancreatic Trypsin Inhibitor—Crystallization, Patterson Search, Structure Determination, Refinement, Structure and Comparison with its Components and with the Bovine Trypsin-Pancreatic Trypsin Inhibitor Complex" J. Mol. Biol., 164:283-311 (1983).
Chen et al., Solution Structure of a Kunitz-type Chymotrypsin Inhibitor Isolated from the Elapid Snake *Bungarus fasciatus*, J. Biological Chemistry 276:45079-45087 (2001).
Chung et al., "Human plasma prekallikrein, a zumogen to a serine protease that contains four tandem repeats," GenBank, Accession #P03952 (1986).
Churg et al., "Proteases and emphysema," Curr. Opin. Pulm. Med., 2005, vol. 11, pp. 153-159.
Colman et al., Hemostasis and Thrombosis Basic Principles and Clinical Practice, Chapter 1, 2nd Edition, 3-17 (1987).
Colman et al., "The Plasma Kallikrein-Kinin System in Sepsis, Inflammatory Arthritis, and Enterocolitis" Clinical Reviews in Allergy and Immunology, vol. 16, pp. 365-384 (1998).

(56) References Cited

OTHER PUBLICATIONS

Colman R. W., "Plasma and tissue Kallikrein in Arthritis and Inflammatory Bowel Disease", Immunopharmacology, Jan. 1, 1999, pp. 103-108, vol. 43, No. 2/03, Elsevier Science Publishers, BV.

Colman RW et al., "Activation of the kallikrein-kinin system in arthritis and enterocolitis in genetically susceptible rats: modulation by a selective plasma kallikrein inhibitor", Proceedings of the Association of American Physicians, Jan. 1, 1997, pp. 10-22, vol. 109, No. 1, Cambridge, MA US.

Colman, "Plasma and tissue kallikrein in arthritis and inflammatory bowel disease," Immunopharmacology, 1999, vol. 43, pp. 103-108.

Colman, et al., "Contact System: A Vascular Biology Modulator With Anticoagulant, Profibrinolytic, Antiadhesive, and Proinflammatory Attributes" Blood, 90, 3819-3843 (1997).

Communication received in EP Patent Application 03791557.6, dated Nov. 27, 2008.

Communication received in EP Patent No. 1 484 339, dated Sep. 29, 2005.

Cumming et al., "Hemodynamic, Renal, and Hormonal Aprotinin in an Ovine Model of Septic Shock," Critical Care Medicine, 20:1134-1139 (1992).

Cunningham et al., "Structural and functional characterization of tissue factor pathway inhibitor following degradation by matrix metalloproteinase-8," Biochem. J., 2002, vol. 367, pp. 451-458.

Currie et al., "Design and Synthesis of a Bicyclic Non-Peptidep-Bend Mimetic of Enkephalin," Tetrahedron, 49:3489-3500 (1993).

De Haard, et al. "A large non-immunized human Fab fragment phage library that permits rapid isolation and kinetic analysis of high affinity antibodies". J. Biol. Chem 274:18218-30, (1999).

De Wildt, et al., "Characterization of human variable domain antibody fragments against the U1 RNA-associated A protein, selected from a synthetic and patient-derived combinatorial V gene library" Eur J Immunol. 26(3):629-39 (1996).

Debiopharm borchure, "Engineering protein inhibitor of human neutrophil elastase EPIO-hNE4 (DX-890)," Dated Oct. 2004, printed from www.debio.com/e/pdf/fiche_epi_hne4_e.pdf.

Dela Cadena et al., "Inhibition of plasma kallikrein prevents peptidoglycan-induced arthritis in the Lewis rat," FASEB J., 1995, vol. 9, pp. 446-452.

Dela Cadena et al., "Role of Kallikrein-Kinin System in the Pathogenesis of Bacterial Cell Wall-Induced Inflammation and Enterocolitis," Transact. Assoc. Am. Physicians, 105:229-237 (1992).

Dela Cadena, et al., "Inhibition of Plasma Kallikrein Prevents Peptidoglycan-Induced Arthritis in the Lewis Rat," FASEB Journal, 9:446-452 (1995).

Delacourt et al., "Protection against acute lung injury by intravenous or intratracheal pretreatment with EPI-HNE-4, a new potent neutrophil elastase inhibitor," Am. J. Respir. Cell Mol. Biol., Mar. 26, 2002, vol. 26, No. 3, pp. 290-297.

Delaria et al., "Characterization of placental bikunin, a novel human serine protease inhibitor," J. Biological Chemistry, May 2, 1997, vol. 272, No. 18, pp. 12209-12214.

Delgado et al., "The uses and properties of PEG-linked proteins," Critical Review in Therapeutic Drug Carrier Systems, 1992, vol. 9, No. 3,4, pp. 249-304.

Deng, et. al., "Production of recombinant humanized anti-HBsAg Fab antibody by fermentation" Sheng Wu Gong Cheng Xue Bao, 20(5):800-4 (Sep. 2004) (Abstact Only).

Dennis & Lazarus, "Kunitz Domain Inhibitors of Tissue Factor-Factor VIIa (I. Potent Inhibitors Selected from Libraries by Phage Display)," Journal of Biological Chemistry 269:22129-22136 (1994).

Dennis & Lazarus, "Kunitz Domain Inhibitors of Tissue Factor-Factor VIIa (II. Potent and Specific Inhibitors by Competitive Phage Selection)," Journal of Biological Chemistry, 269:22137-22144 (1994).

Dennis et al., "Potent and Selective Kunitz Domain Inhibitors of Plasma Kallikrein Designed by Phage Display," J. Biol. Chem., 270:25411-25417 (1995).

Devani et al., "Kallikrein-kinin system in inflammatory bowel disease: intestinal involvement and correlation with the degree of tissue inflammation," Digestive and Liver Disease, 2005, vol. 37, pp. 665-673.

Dhalluin et al., "Structural, kinetic, and thermodynamic analysis of the binding of the 40kDa PEG-interferon-a-2a and its individual positional isomers to the extracellular domain of the receptor IFNAR2," Bioconjugate Chemistry, 2005, vol. 16, pp. 518-527.

Diaz et al., "The Design of Water Soluble β-Sheet Structure Based on a Nucleation Strategy," Tetrahedron, 49:3533-3545 (1993).

Dimaio et al., "A New Class of Potent Thrombin Inhibitors That Incorporates a Scissile Pseudopeptide Bond," FEBS Lett., 282(1):47-52 (1991).

Dittmar et al., "External carotid artery territory ischemia impairs outcome in the endovascular filament model of middle cerebral artery occlusion in rats" Stroke 34: 2252-7 (2003).

Doerks et al., "Protein annotation: detective work for function prediction," Trends in Genetics, vol. 14, No. 6, pp. 248-250 (1998).

Donnelly et al., "Therapy for chronic obstructive pulmonary disease in the 21st century," Drugs, 2003, vol. 63, pp. 1973-1998.

Dragosits, et. al., "The response to unfolded protein is involved in osmotolerance of *Pichia pastoris*" BMC Genomics. Mar. 26, 2010;11:207.

Dufton, "Protein inhibitors and dendrotoxins," Eur. J. Biochem., vol. 153, pp. 647-654. (1985).

Eigenbrot et al. "Structural Effects Induced by Removal of a Disulfide-Bridge: The X-ray Structure of the C30A/C51A Mutant of Basic Pancreatic Trypsin Inhibitor at 1.6 A," Protein Engineering, 3:591-598 (1990).

Eigenbrot et al., "Structural effects induced by removal of a disulfide-bridge: the X-ray structure of the C20A/C51A mutant of basic pancreatic trypsin inhibitor at 1.6 Å," Protein Engineering, 1990, vol. 3, No. 7, pp. 591-598.

Ellis et al., "The Urokinase Receptor: Involvement in Cell Surface Proteolysis and Cancer Invasion," Ann. NY. Acad. Sci., 667:13-31 (1992).

Enzon Pharmaceuticals, Macromolecular Engineering Technologies, 2004, pp. 1-14.

Extended European Search Report and Search Opinion for 08798517.2 dated Oct. 26, 2010.

Extended European Search Report and Search Opinion from European Application No. 05 799 587.0 dated Nov. 15, 2012.

Extended European Search Report and Search Opinion from European Application No. 10180486.2 dated Feb. 9, 2011.

Extended European Search Report and Search Opinion from European Application No. 10180484.7 dated Feb. 28, 2011.

Extended European Search Report and Search Opinion from European Application No. 10164197.5 dated Oct. 1, 2010.

Extended European Search Report and Search Opinion from European Application No. 8798517.2 dated Oct. 26, 2010.

Extended European Search Report and Search Opinion from European Application Serial No. 10180484.7 dated Feb. 28, 2011.

Extended European Search Report and the European Search Opinion from European Application No. 8018863.4 dated Mar. 18, 2009.

Extended European Search Report from European Application No. 10 72 9465 dated Jan. 18, 2013.

Extended European Search Report from European Application No. 7758271.6 dated Jun. 24, 2010.

Fidler & Ellis, "The Implications of Angiogenesis for the Biology and Chemistry of Cancer Metastasis," Cell, 79:185-188 (1994).

Fields & Noble, "Solid Phase Peptide Synthesis Utilizing 9-fluorenylmethocarbonyl Amino Acids," Int. J. Peptide Protein Research, 35:161-214 (1990).

Fife, et al, "Cartilage matrix glycoprotein is present in serum in experimental canine osteoarthritis" J Clin Invest. 84(5):1432-1439 (1989).

Fraedrich, et al., "Reduction of Blood Transfusion requirement in Open Heart Surgery by Administration of High Doses of Aprotinin-Preliminary Results," Thorac Cardiovasc Surgeon, 37:89-91 (1989).

Freidinger, et al., "Protected Lactam-Bridged Dipeptides for Use as Conformational Constraints in Peptides," Journal of Organic Chemistry, 47:104-109 (1982).

(56) References Cited

OTHER PUBLICATIONS

Fries et al., "Inter-a-inhibitor, hyaluronan and inflammation," Acta Biochimica Polonica, 2003, vol. 50, No. 3, pp. 735-742.
Frisbie, "An animal model for venous thrombosis and spontaneous pulmonary embolism." Spinal Cord 43, 635-639 (2005).
G Yetkin et al: "The healing effect of TGF-[alpha] on gastric ulcer induced by acetylsalicylic acid in rats", International Journal of Pharmaceutics, vol. 277, No. 1-2, Jun. 1, 2004, pp. 163-172.
Galeffi, et. al., "Functional expression of a single-chain antibody to ErbB-2 in plants and cell-free systems" J Transl Med. Sep. 29, 2006;4:39.
Gardell, et al., "The Search for the Ideal Thrombolytic Agent: Maximize the Benefit and Minimize the Risk," Toxicologic Pathology, 21(2):190-198 (1993).
Gerriets et al., "Complications and pitfalls in rat stroke models for middle cerebral artery occlusion: a comparison between the suture and the macrosphere model using magnetic resonance angiography", Stroke 35: 2372-2377 (2004).
Girard et al., "Functional significance of the Kunitz-type inhibitory domains of lipoprotein-associated coagulation inhibitor," Nature, 1989, vol. 338, pp. 518-520.
Girard et al., "Functional Significance of the Kunitz-type Inhibitory Domains of Liporotein-Associated Coagulation Inhibitor," Nature, 338:518-520 (1989).
Girard, et al., "Structure of the Human Lipoprotein-associated Coagulation Inhibitor Gene," The Journal of Biological Chemistry, 266:5036-5041 (1991).
Goldenberg et al., "Circular and circularly permuted forms of bovine pancreatic trypsin inhibitor," J. Mol. Biol., vol. 165, pp. 407-413 (1983).
Gonzalez-Quevedo et al., The Synthetic Kunitz Domain Protein DX88 to Treat Angioedema in Patients with Hereditary Angioedema, International Immunopharmacology 2(9):1318 Abstract 205 (2002).
Goodson et al., "Site-directed PEGylation of recombinant interleukin-2 at its glycosylation site," Bio Technology, 1990, vol. 8, pp. 343-346.
Graham et al., "Animal models of ischemic stroke: balancing experimental aims and animal care", Comp Med 54:486-496 (2004).
Greilich et al., "Antifibrinolytic therapy during cardiopulmonary bypass reduces proinglammatory cytokine levels: a randomized, double-blind, placebo-controlled study of x-aminocaproic acid and aprotinin," J. Thorac. Cardiovasc. Surg., 2003, vol. 126, pp. 1498-1503.
Grimaldi et al., "Trasylol in the treatment of acute arthritis due to microcrystals," Reumatismo, vol. 23, No. 5, pp. 217-221, (1971) (Abstract only).
Gulberg et al., "Biosynthesis, processing and sorting of neutrophil proteins: insight into neutrophil granule development," Eur. Journal of Haematology, 1997, vol. 58, pp. 137-153.
Guzman et al. "Mono-iodoacetate-induced histologic changes in subchondral bone and articular cartilage of rat femorotibial joints: an animal model of osteoarthritis." Toxicol Pathol. 31(6):619-24 (2003).
Hagihara et al., "Screening for stable mutants with amino acid pairs substituted for the disulfide bond between residues 14 and 38 of bovine pancreatic trypsin inhibitor (BPTI)," The Journal of Biological Chemistry, 2002, vol. 277, No. 52, pp. 51043-51048.
Han, Eun D. et al., Increased Vascular Permeability in C1 Inhibitor-Deficient Mice Mediated by the Bradykinin Type 2 Receptor, J. Clinical Investigation 109(8):1057-1063 (2002).
Han, Eun D. Reversal of the Increased Vascular Permeability in C1 Inhibitor Deficient Mice: Therapeutic Approaches, International Immunopharmacology 2(9):1315 Abstract 176 (2002).
Hanes et al., "Picomolar affinity antibodies from a fully synthetic naive library selected and evolved by ribosome display" Nat Biotechnol. 18:1287-92 (2000).
Herter et al., "Hepatocyte growth factor is a preferred in vitro substrate for the human hepsin, a membrane-anchored serine protease implicated in prostate and ovarian cancers," Biochem. J., 2005, vol. 390, pp. 125-136.
Hoet, et al., "Generation of high-affinity human antibodies by combining donor-derived and synthetic complementarity-determining-region diversity" Nat Biotechnol. 23(3)344-8 (2005).
Hoogenboom et al. "Natural and designer binding sites made by phage display technology" Immunol Today 2:371-8 (2000).
Hoogenboom et al., "Antibody phage display technology and its applications" Immunotechnology 4:1-20 (1998).
Hoover, et al., "Amino Acids of the Recombinant Kringle 1 Domain of Human Plasminogen that Stabilize Its Interaction w-Amino Acids," Biochemistry, 32:10936-10943 (1993).
Hortin, et al., "Allosteric Changes in Thrombin's Activity Produced by peptides Corresponding to Segments of Natural Inhibitors and Substrates," The Journal of Biological Chemistry, 266:6866-6871 (1991).
Horwitz, et. al., "Secretion of functional antibody and Fab fragment from yeast cells.", Proc Natl Acad Sci U S A. 85(22):8678-82 (Nov. 1988).
Hostomsky, et al., "Solid Phase Assembly of Cow Colostrum Trypsin Inhibitor Gene," Nucleic Acids Research, 15:4849-4856 (1987).
Huang et al., "Kinetics of factor Xa inhibition by tissue factor pathway inhibitor," The Journal of Biological Chemistry, 1993, vol. 268, No. 36, pp. 26950-26955.
Huang et al., "Novel peptide inhibitors of angiotensin-converting enzyme 2," The Journal of Biological Chemistry, 2003, vol. 278, No. 18, pp. 15532-15540.
Huge et al. "A model to investigate postoperative ileus with strain gauge transducers in awake rats" J Surg Res. 74(2):112-8 (1998). (Abstact Only).
Hynes et al., "X-ray crystal structure of the protease inhibitor domain of alzheimer's amyloid b-protein precursor," Biochemistry, 1990, vol. 29, pp. 10018-10022.
International Preliminary Report on Patentability from International Application No. PCT/US2008/073665 dated Feb. 24, 2010.
International Preliminary Report on Patentability from International Application No. PCT/US2008/074061 dated Mar. 4, 2010.
International Search Report from International Application No. PCT/US11/20377 dated Jun. 28, 2011.
International Search report from International Application No. PCT/US2004/028256 dated 2005.
International Search Report from International Application No. PCT/US05/34335 dated Jul. 21, 2008.
International Search Report from International Application No. PCT/US07/63703 dated Dec. 21, 2007.
International Search Report from International Application No. PCT/US12/20470 dated Apr. 30, 2012.
International Search Report from International Application No. PCT/US2008/074061 dated Dec. 29, 2008.
International Search Report from International Application No. PCT/US2010/020257 dated Jun. 1, 2010.
U.S. Appl. No. 10/016,329, filed Oct. 26, 2001, Markland.
U.S. Appl. No. 11/860,853, filed Sep. 25, 2007, Ladner et al.
U.S. Appl. No. 11/930,700, filed Oct. 31, 2007, Ladner et al.
U.S. Appl. No. 12/471,875, filed May 26, 2009, Ley et al.
"Current Protocols in Molecular Biology", 1989, John Wiley & Sons, pp. 6.3.1-6.3.6.
A.F. Williams; A.N. Barclay, Ann. Rev Immunol., 1988, vol. 6, pp. 381-405.
Altschul et al., "Gapped BLAST and PSI-BLAST: a new generation of protein database search programs," Nucleic Acids Research, 1997, vol. 25, pp. 3389-3402, Oxford University Press.
Carlson et al., Anal. Biochem., 1988, vol. 168, pp. 428-435.
Chothia, C. et al., "Canoical Structures for the Hypervariable Regions of Immunoglobins" J. Mol. Biol., 1987, vol. 196, pp. 901-917.
Communication from the European Patent Office for EP Application No. 10180484.7 dated Dec. 11, 2013, 3 pages.
Corpet et al., "Recent improvements of the ProDom database of protein domain families," Nucl. Acids Res., 1999, vol. 27, pp. 263-267.
English Translation of Final Office Action for Japanese Application No. 2004-510605 dated Apr. 28, 2010, 3 pages.
English Translation of Office Action for Japanese Application No. 2010-004265 dated May 1, 2012, 3 pages.

(56) References Cited

OTHER PUBLICATIONS

English Translation of Office Action for Japanese Patent Application No. 2004-510605 dated Jul. 10, 2009, 6 pages.
English Translation of Office Action for JP 2011-164650 mailed Oct. 2, 2013, 5 pages.
English Translation of Official Action for Japanese Application No. 2007-533689 dated Apr. 27, 2011, 6 pages.
English Translation of Official Action for Japanese Application No. 2007-533689, mail date Nov. 18, 2011, 8 pages.
English Translation of Official Action for Japanese Application No. 2007-533689, mail date Sep. 18, 2012, 5 pages.
English Translation of Official Action for Japanese Application No. 2011-164650, mail date Mar. 21, 2013, 5 pages.
English Translation of Official Action for Japanese Application No. 2012-242083 dated May 26, 2014, 2 pages.
European Search Report for EP Application No. 07023364.8, mail date Jun. 6, 2008, 7 pages.
Examination Report for Canadian Application No. 2581680 dated Feb. 17, 2012, 5 pages.
Examination Report No. 1 for Australian Patent Application No. 2011201811 dated Feb. 11, 2013, 7 pages.
Examination Report No. 2 on Australian Patent Application No. 2008202377 dated Oct. 4, 2010, 2 pages.
Examination Report No. 2 on Australian Patent Apppplication No. 2011201811 dated Feb. 13, 2013, 3 pages.
Examiner's First Report on Australian Patent Application No. 2003243394 dated Sep. 6, 2006, 2 pages.
Examiner's First Report on Australian Patent Application No. 2005289621 dated Apr. 2010, 2 pages.
Examiner's First Report on Australian Patent Application No. 2008202377 dated Aug. 12, 2009, 2 pages.
Examiner's First Report on Australian Patent Application No. 2011218732 dated Apr. 2012, 1 page.
Examiner's Report for Canadian Application No. 2488558 dated Mar. 7, 2012, 2 pages.
Examiner's Report for Canadian Application No. 2488558 dated Nov. 12, 2010, 3 pages.
Examiner's Report No. 2 on Australian Patent Application No. 2003243394 dated Sep. 26, 2007, 3 pages.
Examiner's Report No. 3 on Australian Patent Application No. 2008202377 dated Jan. 31, 2011, 2 pages.
Extended European Search Report and Search Opinion from European Application No. 10180486.2 dated Feb. 23, 2011.
Extended European Search Report for EP Application No. 13174097.9 dated Nov. 15, 2013, 16 pages.
Falquet et al., "The PROSITE databse, its status in 2002," Nucleic Acids Res., 2002, vol. 30, pp. 235-238.
Final Office Action for U.S. Appl. No. 11/931,373 dated Jan. 4, 2010, 14 pages.
Final Office Action for U.S. Appl. No. 10/456,986 dated May 18, 2005, 9 pages.
Final Office Action for U.S. Appl. No. 11/804,388 dated Nov. 17, 2011, 9 pages.
Final Office Action for U.S. Appl. No. 11/929,729 dated Aug. 22, 2011, 7 pages.
Final Office Action for U.S. Appl. No. 12/951,543 dated Jul. 18, 2013.
Final Office Action on U.S. Appl. No. 11/930,018 dated Jan. 11, 2010, 12 pages.
Final Office Action on U.S. Appl. No. 13/458,086 dated Aug. 7, 2013, 7 pages.
Gouzy et al., "Whole genome protein domain analysis using a new method for domain clustering," Computers and Chemistry, 1999, vol. 23, pp. 333-340.
Greilich et al., "Antifibrinolytic therapy during cardiopulmonary bypass reduces proinglammatory cytokine levels: a randomized, double-blind, placebo-controlled study of x-aminocaproic acid and aprotinin," J. Thorac. Cardiovasc. Surg., 2003, vol. 126, pp. 1498-1503.
Gribskov et al., "Profile Analysis", Meth. Enzymol., 1990, vol. 183, pp. 146-159.
Gribskov et al., "Profile analysis: Detection of distantly related proteins," Proc. Natl. Acad. Sci. USA, 1987, vol. 84, pp. 4355-4358.
Hwang I K et al: "Copper chaperone for Cu,Zn-SOD supplement potentiates the Cu,Zn-SOD function of neuroprotective effects against ischemic neuronal damage in the gerbil hippocampus", Free Radical Biology and Medicine, Elsevier Science, US, vol. 39, No. 3, Aug. 1, 2005, pp. 392-402, abstract only 2 pages.
Hynes et al., "X-ray Crystal Structure of the Protease Inhibitor Domain of Alzheimer's Amyloid β-Protein Precursor," Biochemistry, 32:10936-10943 (1993).
International Preliminary Examination Report for International Application No. PCT/US2003/017665 dated Mar. 30, 2005, 10 pages.
International Preliminary Report on Patentability for International Application No. PCT/US2005/034335 dated Mar. 3, 2009, 7 pages.
International Search Report for Application No. PCT/US2003/017665, mail date Jan. 6, 2005, 2 pages.
Krogh et al., "Hidden Markov Models in Computational Biology," J. Mol. Biol., 1994, vol. 235, pp. 1501-1531.
Markland et al., Iterative optimization of high-affinity protease inhibitors using phage display. 2. Plasma kallikrein and thrombin. Biochemistry. Jun. 18, 1996;35(24):8058-67.
Merrifield, B., "Solid Phase Synthesis," Science, 232:341-347 (1986).
Needleman; Wunsch, "A General Method Applicable to the Search for Similarities in the Amino Acide Sequence of Two Proteins". Mol. Biol., 1970, vol. 48, pp. 443-453.
Non-Final Office Action for U.S. Appl. No. 11/931,635 dated Nov. 12, 2008, 8 pages.
Non-Final Office Action for U.S. Appl. No. 10/456,986 dated Oct. 21, 2004, 17 pages.
Non-Final Office Action for U.S. Appl. No. 10/953,902 dated Dec. 14, 2005, 10 pages.
Non-Final Office Action for U.S. Appl. No. 11/125,639 dated Jul. 5, 2006, 8 pages.
Non-Final Office Action for U.S. Appl. No. 11/322,960 dated Oct. 31, 2006, 9 pages.
Non-Final Office Action for U.S. Appl. No. 11/323,261 dated Aug. 2, 2006, 4 pages.
Non-Final Office Action for U.S. Appl. No. 11/323,261 dated Dec. 26, 2006, 5 pages.
Non-Final Office Action for U.S. Appl. No. 11/323,261 dated Mar. 22, 2007, 7 pages.
Non-Final Office Action for U.S. Appl. No. 11/466,979 dated Dec. 5, 2008, 8 pages.
Non-Final Office Action for U.S. Appl. No. 11/466,979 dated Jun. 12, 2008, 9 pages.
Non-Final Office Action for U.S. Appl. No. 11/796,272 dated Feb. 2, 2009, 11 pages.
Non-Final Office Action for U.S. Appl. No. 11/796,272 dated Jan. 13, 2010, 8 pages.
Non-Final Office Action for U.S. Appl. No. 11/804,388 dated Dec. 8, 2009, 9 pages.
Non-Final Office Action for U.S. Appl. No. 11/804,388 dated Jun. 10, 2011, 8 pages.
Non-Final Office Action for U.S. Appl. No. 11/804,388 dated Jun. 15, 2010, 12 pages.
Non-Final Office Action for U.S. Appl. No. 11/860,853 dated Apr. 17, 2009, 8 pages.
Non-Final Office Action for U.S. Appl. No. 11/929,685 dated Dec. 2, 2008, 13 pages.
Non-Final Office Action for U.S. Appl. No. 11/929,729 dated Aug. 26, 2009, 12 pages.
Non-Final Office Action for U.S. Appl. No. 11/929,729 dated Dec. 29, 2010, 9 pages.
Non-Final Office Action for U.S. Appl. No. 11/929,729 dated May 26, 2010, 9 pages.
Non-Final Office Action for U.S. Appl. No. 11/929,822 dated Feb. 9, 2010, 6 pages.
Non-Final Office Action for U.S. Appl. No. 11/929,822 dated Jan. 10, 2011, 5 pages.

(56) References Cited

OTHER PUBLICATIONS

Non-Final Office Action for U.S. Appl. No. 11/929,876 dated Dec. 1, 2009, 10 pages.
Non-Final Office Action for U.S. Appl. No. 11/930,012 dated Aug. 27, 2009, 9 pages.
Non-Final Office Action for U.S. Appl. No. 11/930,018 dated Nov. 12, 2008, 14 pages.
Non-Final Office Action for U.S. Appl. No. 11/930,700 dated Nov. 9, 2009, 8 pages.
Non-Final Office Action for U.S. Appl. No. 11/930,802 dated Jan. 8, 2010, 9 pages.
Non-Final Office Action for U.S. Appl. No. 11/930,897 dated Nov. 6, 2009, 9 pages.
Non-Final Office Action for U.S. Appl. No. 11/931,361 dated Dec. 8, 2009, 8 pages.
Non-Final Office Action for U.S. Appl. No. 11/931,361 dated Jun. 15 2010, 10 pages.
Non-Final Office Action for U.S. Appl. No. 11/931,373 dated Jun. 12, 2009, 7 pages.
Non-Final Office Action for U.S. Appl. No. 11/931,373 dated May 4, 2010, 11 pages.
Non-Final Office Action for U.S. Appl. No. 11/931,665 dated Dec. 2, 2009, 10 pages.
Non-Final Office Action for U.S. Appl. No. 11/931,665 dated Jun. 14, 2010, 12 pages.
Non-Final Office Action for U.S. Appl. No. 11/931,810 dated Dec. 9, 2009, 10 pages.
Non-Final Office Action for U.S. Appl. No. 11/931,810 dated Jul. 12, 2010, 17 pages.
Non-Final Office Action for U.S. Appl. No. 11/931,941 dated Oct. 28, 2009, 8 pages.
Non-Final Office Action for U.S. Appl. No. 11/932,015 dated Oct. 27, 2009, 7 pages.
Non-Final Office Action for U.S. Appl. No. 11/932,098 dated Mar. 5, 2010, 12 pages.
Non-Final Office Action for U.S. Appl. No. 11/932,184 dated Oct. 27, 2009, 8 pages.
Non-Final Office Action for U.S. Appl. No. 12/951,543 dated Feb. 12, 2013, 10 pages.
Non-Final Office Action on U.S. Appl. No. 11/796,272 dated Jul. 31, 2009, 11 pages.
Non-Final Office Action on U.S. Appl. No. 13/458,086 dated Feb. 28, 2013, 15 pages.
Notice of Allowance for U.S. Appl. No. 10/456,986 dated Dec. 21, 2005, 6 pages.
Notice of Allowance for U.S. Appl. No. 10/953,902 dated May 31, 2006, 8 pages.
Notice of Allowance for U.S. Appl. No. 11/125,639 dated Mar. 19, 2007, 6 pages.
Notice of Allowance for U.S. Appl. No. 11/323,261 dated Jun. 27, 2007, 6 pages.
Notice of Allowance for U.S. Appl. No. 11/466,979 dated Aug. 13, 2009, 7 pages.
Notice of Allowance for U.S. Appl. No. 11/466,979 dated Dec. 4, 2009, 6 pages.
Notice of Allowance for U.S. Appl. No. 11/804,388 dated Feb. 16, 2012, 8 pages.
Notice of Allowance for U.S. Appl. No. 11/929,729 dated Dec. 12, 2011, 10 pages.
Notice of Allowance for U.S. Appl. No. 11/929,822 dated Jun. 10, 2011, 9 pages.
Notice of Allowance for U.S. Appl. No. 11/930,012 dated Jun. 3, 2010, 7 pages.
Notice of Allowance for U.S. Appl. No. 11/931,373 dated Sep. 22, 2010, 13 pages.
Notice of Allowance for U.S. Appl. No. 12/951,543 dated Dec. 12, 2013, 11 pages.
Office Action for European Application No. 03757339.1 dated Aug. 20, 2008, 5 pages.
Office Action for European Application No. 03757339.1 dated Dec. 8, 2008, 4 pages.
Office Action for European Application No. 03757339.1 dated May 11, 2009, 4 pages.
Office Action for European Application No. 07023364.8 dated Mar. 18, 2010, 5 pages.
Office Action for European Application No. 10180484.7 dated Feb. 16, 2012, 5 pages.
Office Action for European Application No. 10180486.2 dated Dec. 17, 2013, 4 pages.
Office Action for European Application No. 10180486.2 dated Feb. 16, 2012, 4 pages.
Official Action for Japanese Patent Application No. 2013-114068 dated Jun. 25, 2014, 2 pages. (English translation not available).
PCT International Search Report and Written Opinion dated Jul. 21, 2008 and issued in PCT/US05/34335.
Schultz et al., "SMART: a web-based tool for the study of genetically mobile domains," Nucl. Acids Res, 2000, vol. 28, p. 231-234.
Schultz et al., "SMART, a simple modular architecture research tool: Identification of signaling domains," Proc. Natl. Acad. Sci. USA, 1998, vol. 95, p. 5857.
Sik Eum W et al: "In vivo protein transduction: biologically active intact pep-1-superoxide dismutase fusion protein efficiently protects against ischemic insult", Free Radical Biology and Medicine, Elsevier Science, US, vol. 37, No. 10, Nov. 15, 2004, pp. 1656-1669.
Sonhammer et al., "Pfam: A Comprehensive Database of Protein Domain Families Based on Seed Alignments," Proteins, 1997, vol. 28 (3), pp. 405-420.
Strom et al., Therapeutic Immunology, Austen et al. (Ed.), Blackwell Science, Cambridge MA, 1996; pp. 451-456.
Stultz et al., "Structural analysis based on state-space modeling," Protein Sci., 1993, vol. 2, pp. 305-314.
Supplemental Final Office Action on U.S. Appl. No. 11/930,018 dated Mar. 18, 2010, 13 pages.
Wood, Alastair, J.J, "Hemostatic Drugs" New England Journal of Medicine, Drug Therapy, vol. 339, No. 4, pp. 245-253 (1998).
Supplementary European Search Report including the European Search Opinion from corresponding European Application No. EP06848187.8, dated Dec. 7, 2009.
Taby et al., "Inhibition of activated protein C by aprotinin and the uses of the insolubilized inhibitor for its purification," Thrombosis Research, 1990, vol. 59, pp. 27-35.
Taggart et al., "Inactiviation of human-b-defensins 2 and 3 by elastolytic cathepsins1," The Journal of Immunology, 2003, vol. 170, pp. 931-937.
Takahashi, et al., "Production of humanized Fab fragment against human high affinity IgE receptor in *Pichia pastoris*" Biosci Biotechnol Biochem 64(10):2138-44 (2000).
Tamura, et al., "Focal cerebral ischaemia in the rat: 1. Description of technique and early neuropathological consequences following middle cerebral artery occlusion" J Cereb Blood Flow Metab 1:53-60 (1981).
The Merck Index: 145, 263, 427, 428, 1183, and 1184 (1989).
Tian et al., "Synthesis of Optically Pure C?-methyl-arginine," Int. J. Peptide Res., 40:119-126 (1992).
Travis et al., "Pulmonary perspective: potential problems in designing elastase inhibitors for therapy," Am. Rev. Respir. Dig., 1991, vol. 143, pp. 1412-1415.
Tremblay et al., "Anti-inflammatory activity of neutrophil elastase inhibitors," Current Opinion in Investigational Drugs, 2003, vol. 4, No. 5, pp. 556-565.
Tschesche et al., "Semisynthetic engineering of proteinase inhibitor homologues," Biochim. Biophys. Acta, vol. 913, pp. 97-101 (1987).
Uebel,"Die behandlung con kniegelenksarthrosen mit trasylol," Langenbacks Arch. Chir., vol. 325, pp. 356-358 (1969). English Abstract Only.
Urlaub et al., "Isolation of Chinese hamster cell mutants deficient in dihydrofolate reductase activity", Proc. Natl. Acad. Sci. USA 77:4216-4220 (1980).
Van Der Logt et al., "Intron-Exon Organization of the Human Gene Coding for the Lipoprotein-associated Coagulation Inhibitor: The Factor Xa Dependent of Inhibitor of the Extrinsic Pathway of Coagulation," Biochemistry, 30:1571-1577 (1991).

(56) References Cited

OTHER PUBLICATIONS

Van Dijl et al., "Signal Peptidase 1 of *Bacillus subtillis*: Patterns of Conserved Amino Acids in Prokaryotic and Eukaryotic Type 1 Signal Peptidases," The EMBO Journal, 11:2819-2828 (1992).
Varadi et al., "Location of Plasminogen-Binding Sites in Human Fibrin(ogen)," Biochemistry, 22:2440-2446 (1983).
Varadi, et al., Segment of Fibrinogen Is in a Region Essential for Plasminogen Binding by Fibrin Fragment E, Biochemistry, 23:2108-2112 (1984).
Vedvick, et al., "High-Level Secretion of Biologically Active Aprotinin from the Yeast *Pichia pastoris*," J. Ind. Microbiol., 7:197-201 (1991).
Veronese, "Peptide and protein PEGylation: a review of problems and solutions," Biomaterials, Mar. 1, 2001, vol. 22, No. 5, pp. 405-417.
Vidal et al., "Making sense of antisense," European Journal of Cancer, 2005, vol. 41, pp. 2812-2818.
Viswanathan M. et al., "Engineered protein protease inhibitors", Current Enzyme Inhibition, Jan. 1, 2009, pp. 87-98, vol. 5, No. 2, Betham Science Publishers Ltd., Hilversum, NL.
Volpe-Junior et al., "Augmented plasma and tissue kallikrein like activity in synovial fluid of patients with inflammatory articular diseases," Inflamm. Res., 1996, vol. 45, pp. 198-202.
Wade, et al., "Solid-Phase Synthesis of ?-Human Atrial Natriuretic Factor: Comparison of the Boc-Polystyrene and Fmoc-Polyamide Methods," Biopolymers, 25: S21-S37 (1986).
Wagner et al., High Level Expression, Purification, and Characterization of the Kunitz-Type Protease Domain of Protease Nexin-2/Amyloid β-Protein Precursor, Biochemical and Biophysical Research Communications, 186: 1138-1145 (1992).
Wang et al., "Monitoring of heparin-induced anticoagulation with kaolin-activated clotting time in cadiac surgical patients treated with aprotinin," Anesthesiology, vol. 77, pp. 1080-1084 (1992).
Wark P.A., "DX-890 (Dyax)", iDrugs, 5, pp. 586-589, Jun. 2002.
Wellington et al., "Tranexannic Acid: A review of its use in the management of menorrhagia", Drugs, vol. 63, No. 13, pp. 1417-1433, 2003.
Wells, "Addivity of Mutational Effects in Proteins", Biochemistry, vol. 29 (37), pp. 8509-8517 (1990).
Wendel et al., Lower Cardiac Troponin T Levels in Patients Undergoing Cardiopulmonary Bypass and Receiving High-Dose Aprotinin Therapy Indicate Reduction of Perioperative Myocardial Damage; Journal of Thoracic Cardiovascular Surgery, vol. 109, No. 6, pp. 1164-1172 (1995).
Wilson, et al., "The Calculation and Synthesis of a Template Molecule," Tetrahedron, 49:3655-3663 (1993).
Worthy et al., "Current status review kallikreins and kinins: mediators in inflammatory joint disease," Int. J. Exp, 1990.
Worthy, K. et al., "Kallikreins and Kinins: Mediators in Inflammatory Joint Disease?", International Review of Experimental Pathology, pp. 587-601, vol. 71, No. 4, Blackwell Scientific, Oxford GB (Aug. 1, 1990).
Written Opinion from International Application No. PCT/US05/34335 dated Jul. 21, 2008.
Written Opinion from International Application No. PCT/US11/20377 dated Jun. 28, 2011.
Written Opinion from International Application No. PCT/US2008/074061 dated Dec. 29, 2008.
Wun et al., "Cloning and Characterization of a cDNA Coding for the Lipoprotein-associated Coagulation Inhibitor Shows that it Consists of Three Tandem Kunitz-type Inhibitory Domains," J. Biol. Chem. 263:6001-6004 (1988).
Wun et al., "Cloning and characterization of a cDNA coding for the lipoprotein-associated coagulation inhibitor shows that it consists of three tandem Kunitz-type inhibitory domains," The Journal of Biological Chemistry, 1988, vol. 263, No. 13, pp. 6001-6004.

XP_376532.2 (GI:51465288): "Predicted: KIAA0408", GenBank Record created on Aug. 19, 2004, GenBank [online] Bethesda, MD USA: United States National Library of Medicine, retrieved from internet using <URL:http://www.ncbi.nlm.nih.gov/protein/XP_376532.2?report=genpept> GenBank Accession No. XP_376532.2 (GI:51465288).
Xu et al., "The crystal structure of bikunin from the inter-a-inhibitor complex: a serine protease inhibitor with two Kumitz domains," J. Mol. Biol. Mar. 13, 1998, vol. 276, No. 5, pp. 955-966.
Dittmar et al., "Fischer-344 rats are unsuitable for the MCAO filament model due to their cerebrovascular anatomy" J Neurosci Methods 156: 50 (2006).
De Wildt, et al. "Antibody arrays for high-throughput screening of antibody-antigen interactions", Nat. Biotechnol. 18:989-994 (2000).
De Campos, et al., "Antioedematogenic and antinociceptive actions of NPC 18521, a novel bradykinin B2 receptor antagonist", Eur J Pharmacol316, 277-286 (1996).
Murkin et al., "Aprotinin significantly decreases bleeding and transfusion requirements in patients receiving aspirin and undergoing cardiac operations," J. Thorac. Cardiovasc. Surg., vol. 107, pp. 554-561 (1994).
Naess, et al., "Effects of a Combined Drug Regimen on Tumour Necrosis Factor and Plasma Kallikrein Activity in Experimental Endotoxaemia," Eur. J. Surg., 160:77-86 (1994).
Nagai et al., "Synthesis of a Bicyclic Dipeptide with the Shape of a-Turn Central Part," Tetrahedron Letters, 26(5):647-650 (1985).
Nagai, et al., Bicyclic Turned Dipeptide (BTD) as a a-Turn Mimetic; its Design, Synthesis, and Incorporation into Bioactive Peptides, Tetrahedron, 49:3577-3592 (1993).
Nektartm—Transforming Therapeutics, Nektar Advanced PEGylation: Polyethylene Glycol and Derivatives for Advanced PEGylation, pp. 1-24, catalogue 2004.
Nektartm—Transforming Therapeutics, Nektar Molecule Engineering: Polyethylene Glycol and Derivatives for Advanced PEGylation, pp. 1-20, catalogue—2003.
Neuhaus, et al., "Effect of Aprotinin on Intraoperative Bleeding and Fibrinolysis in Liver Transplantation," Lancet, 2: 924-925 (1989).
Ngo et al., "The protein folding problem and tertiary structure prediction, Chapter 14: Computational complexity protein structure prediction, and the Levinthal paradox," pp. 433-440 and 492-495 only (1994).
Ngo, et al., "Computational Complexity, Protein Structure Prediction, and the Levinthal Paradox", The Protein Folding Problem and Tertiary Structure Prediction, Chapter 14, pp. 433-440 and 492-495 only (1994).
Ning, et. al., "Production of recombinant humanized anti-HBsAg Fab fragment from *Pichia pastoris* by fermentation.", J Biochem Mol Biol. ;38(3):294-9. (May 31, 2005).
NM_008455.2 (GI: 236465804): "Plasma kallikrein precursor", GenBank Record created on Dec. 29, 2010 GenBank [online] Bethesda, MD USA: United States National Library of Medicine, retrieved from internet using <URL: http://www.ncbi.nlm.nih.gov/nuccore/236465804?sat=14&satkey=4833839> GenBank Accession No. NM_008455.2 (GI: 236465804).
NM_012725.2 (GI:162138904): "Plasma kallikrein precursor", GenBank Record created on Dec. 26, 2010 GenBank [online] Bethesda, MD USA: United States National Library of Medicine, retrieved from internet using <URL: http://www.ncbi.nlm.nih.gov/nuccore/162138904?sat=14&satkey=5346361> GenBank Accession No. NM_012725.2 (GI:162138904).
NOF Corporation, "PEG Derivatives, Phospholipid and Drug Delivery Materials for Pharmaceutical Products and Formulations," pp. 1-59, catalogue Ver. 8—Apr. 2006.
NOF Corporation, "PEG Derivatives, Phospholipid and Drug Delivery Materials for Pharmaceuticals," pp. 1-46, catalogue—2003, 1st.
NOF Corporation, "PEG Derivatives, Phospholipid and Drug Delivery Materials for Pharmaceuticals," pp. 1-50, catalogue—2003 2nd.
Novotney et al., "Purification and Characterization of the Lipoprotein-associated Coagulation Inhibitor from Human Plasma," J. Biol. Chem. 264:18832-18837 (1989).
Novotny et al., "Purification of characterization of the lipoprotein-associated coagulation inhibitor from human plasma," The Journal of Biological Chemistry, 1989, vol. 264, No. 31, pp. 18832-18837.

(56) References Cited

OTHER PUBLICATIONS

NP_000217.2 (GI:55956899): "keratin, type I cytoskeletal 9", GenBank Record created on Dec. 27, 2010 GenBank [online] Bethesda, MD USA: United States National Library of Medicine, retrieved from internet using <URL: http://www.ncbi.nlm.nih.gov/protein/55956899?sat=14&satkey=4890700> GenBank Accession No. NP_000217.2 (GI:55956899).

NP_000418.2 (GI:109255251): "loricrin", GenBank Record created on Nov. 3, 2010 GenBank [online] Bethesda, MD USA: United States National Library of Medicine, retrieved from internet using <URL:http://www.ncbi.nlm.nih.gov/protein/109255251?sat=14&satkey=6156833> GenBank Accession No. NP_000418.2 (GI:109255251).

NP_000883.2 (GI: 78191798): "Plasma kallikrein preproprotein", GenBank Record created on Nov. 21, 2010, GenBank [online] Bethesda, MD USA: United States National Library of Medicine, retrieved from internet using <URL: http://www.ncbi.nlm.nih.gov/protein/78191798?sat=14&satkey=4530481> GenBank Accession No. NP_000883.2 (GI: 78191798).

NP_000892 (GI: 158508572): "mineralocorticoid receptor isoform 1", GenBank Record created on Dec. 27, 2010, GenBank [online] Bethesda, MD USA: United States National Library of Medicine, retrieved from internet using <URL: http://www.ncbi.nlm.nih.gov/protein/158508572?sat=14&satkey=4536058> GenBank Accession No. NP_000892.2 (GI: 158508572).

NP_005850.1 (GI:5032007): "transcriptional activator protein Pur-alpha", GenBank Record created on Dec. 28, 2010, GenBank [online] Bethesda, MD USA: United States National Library of Medicine, retrieved from internet using <URL:http://www.ncbi.nlm.nih.gov/protein/5032007?sat=14&satkey=4526134> GenBank Accession No. NP_005850.1 (GI:5032007).

NP_006228.3 (GI:110347449): "POU domain, class 4, transcription factor 1", GenBank Record created on Dec. 27, 2010, GenBank [online] Bethesda, MD USA: United States National Library of Medicine, retrieved from internet using <URL:http://www.ncbi.nlm.nih.gov/protein/110347449?sat=14&satkey=4536081> GenBank Accession No. NP_006228.3 (GI:110347449).

NP_009060.2 (GI:22547197): "zinc finger protein ZIC 2", GenBank Record created on Dec. 24, 2010, GenBank [online] Bethesda, MD USA: United States National Library of Medicine, retrieved from internet using <URL:http://www.ncb.nlm.nih.gov/protein/22547197?sat=14&satkey=4290853> GenBank Accession No. NP_0090602 (GI:22547197).

NP_031393.2 (GI:21396480): "RNA-binding protein Raly isoform 2", GenBank Record created on Dec. 25, 2010, GenBank [online] Bethesda, MD USA: United States National Library of Medicine, retrieved from internet using <URL:http://www.ncb.nlm.nih.gov/protein/21396480?sat=14&satkey=4835374> GenBank Accession No. NP_031393.2 (GI:21396480).

NP_032481.2 (GI: 236465805): "Plasma kallikrein precursor", GenBank Record created on Dec. 29, 2010 GenBank [online] Bethesda, MD USA: United States National Library of Medicine, retrieved from internet using <URL: http://www.ncbi.nlm.nih.gov/protein/236465805?sat=14&satkey=4833839> GenBank Accession No. NP_032481.2 (GI:236465805).

NP_036857.2 (GI:162138905): "Plasma kallikrein precursor", GenBank Record created on Dec. 26, 2010 GenBank [online] Bethesda, MD USA: United States National Library of Medicine, retrieved from internet using <URL: http://www.ncbi.nlm.nih.gov/protein/162138905?sat=14&satkey=5346361> GenBank Accession No. NP_036857.2 (GI:162138905).

NP_056932.2 (GI:153791670): "Plasma kallikrein preproprotein", GenBank Record created on Dec. 27, 2010, GenBank [online] Bethesda, MD USA: United States National Library of Medicine, retrieved from internet using <URL: http://www.ncbi.nlm.nih.gov/protein/153791670?sat=14&satkey=4553701> GenBank Accession No. NP_056932.2 (GI:153791670).

NP_061856.1 (GI:9506713): "H/ACA ribonucleoprotein complex subunit 1", GenBank Record created on Dec. 24, 2010, GenBank [online] Bethesda, MD USA: United States National Library of Medicine, retrieved from internet using <URL:http://www.ncb.nlm.nih.gov/protein/9506713?sat=14&satkey=4524138> GenBank Accession No. NP_061856.1 (GI:9506713).

NP_065104.1 (GI:9966841): "cell death regulator Aven", GenBank Record created on Dec. 26, 2010, GenBank [online] Bethesda, MD USA: United States National Library of Medicine, retrieved from internet using <URL:http://www.ncb.nlm.nih.gov/protein/9966841?sat=14&satkey=4843224> GenBank Accession No. NP_065104.1 (GI:9966841).

NP_115818.2 (GI:53829370): "neuralized-like protein 4 isoform 1", GenBank Record created on Dec. 27, 2010, GenBank [online] Bethesda, MD USA: United States National Library of Medicine, retrieved from internet using <URL: http://www.ncbi.nlm.nih.gov/protein/53829370?sat=14&satkey=4560911> GenBank Accession No. NP_115818.2 (GI:53829370).

NP_476429.2 (GI:109148552): "keratin, type II cytoskeletal 3", GenBank Record created on Dec. 24, 2010 GenBank [online] Bethesda, MD USA: United States National Library of Medicine, retrieved from internet using <URL: http://www.ncbi.nlm.nih.gov/protein/109148552?sat=14&satkey=6358709> GenBank Accession No. NP_NP_476429.2 (GI:109148552).

NP_631961.1 (GI:21327701): "TATA-binding protein-associated factor 2N isoform 1", GenBank Record created on Dec. 25, 2010, GenBank [online] Bethesda, MD USA: United States National Library of Medicine, retrieved from internet using <URL: http://www.ncbi.nlm.nih.gov/protein/21327701?sat=14&satkey=4528109> GenBank Accession No. NP_631961.1 (GI:21327701).

NP_787059.2 (GI:40068462): "AT-rich interactive domain-containing protein 1B isoform 3", GenBank Record created on Mar. 4, 2010, GenBank [online] Bethesda, MD USA: United States National Library of Medicine, retrieved from Internet using <URL:http://www.ncbi.nlm.nih.gov/protein/NP_787059.2?report=genpept> GenBank Accession No. NP_787059.2 (GI:40068462).

Nwariaku, et al., "Effect of a bradykinin antagonist on the local inflammatory response following thermal injury" Burns, 22:324-327 (1996).

O'Reilly, et al., "Angiostatin: A Novel Angiogenesis Inhibitor That Mediates the Suppression of Metases by a Lewis Lung Carcinoma," Cell, 79 317-328 (1994).

Okamoto, et al., "A Finding of Highly Selective Synthetic Inhibitor of Plasma Kallikrein; Its Action to Bradykinin Generation, Intrinsic Coagulation and Experimental DIC," Agents Actions Suppl., 38(I):198-205 (1992).

Pan et al., "Reperfusion inury following cerebral ischemia: pathophysiology, MR imaging, and potential therapies," Neuroradiology, 2007, vol. 49, pp. 93-102.

Park, et al., "Three Dimensional Structure of the Kringle Sequence: Structure of Prothrombin Fragment 1," Biochemistry, 25:3977-3982 (1986).

Petersen et al., "Inhibitory propterties of separate recombinant Kunitz-type-protease-inhibitor domains from tissuefactor-pathway inhibitor," Eur. J. Biochem., 1996, vol. 235, pp. 310-316.

Phillips, "The challenge of gene therapy and DNA dellicery," J. Pharm. Pharmacology, vol. 53, pp. 1169-1174 (2001).

Pintigny et al., "Aprotinin can inhibit the proteolytic activity of thrombin: a fluorescence and an enzymatic study," Eur. J. Biochem., 1992, vol. 207, pp. 89-95.

Piro et al., "Role for the Kunitz-3 domain of tissue factor pathway inhibitor-a in cell surface binding," Circulation, 2004, vol. 110, pp. 3567-3572.

Pirollo et al., "Targeted delivery of small interfering RNA: approaching effective cancer therapies," Cancer Res., 2008, vol. 68, No. 5, pp. 1247-1250.

(56) References Cited

OTHER PUBLICATIONS

Pitt et al., "Rabbit monoarticular arthritis as a model for intra-articular drug injections. The local action of administered cortisol and a-1 proteinase inhibitor," Agents and Actions, vol. 15, No. 5-6, abstract online, retrieved from internet <URl:http://www.springerlink.com/content/j82860503948741/p> (Dec. 1984).

Polypure, Products; PEG amines; PEG acids and amino acids, PEG thils and disulfides; BIOTINS, Apr. 2005.

Polypure, Products; PEG amines; PEG acids and amino acids; PEG thiols and disulfides; BIOTINS, Apr. 2004.

Poznansky et al., "Growth hormone-albumin-conjugates reduced renal toxicity and altered plasma clearance," 1988, vol. 239, pp. 18-22.

Preliminary Report on Patentability from International Application No. PCT/US11/20377 dated Jun. 28, 2011.

Putterman, C., "Aprotinin Therapy in Septic Shock," ACTA Chir. Scand., 155:367 (1989).

\* cited by examiner

```
5AOX1
-------------------------------->                                BstB I
CG ACT TTT AAC GAC AAC TTG AGA AGA TCA AAA AAC AAC TAA TTA TTC GAA

ACG     ATG AGA TTC CCA TCT ATC TTC ACT GCT GTT TTG TTC GCT GCT
        M   R   F   P   S   I   F   T   A   V   L   F   A   A

TCC TCT GCT TTG GCT GCT CCA GTT AAC ACC ACT ACT GAA GAC GAG ACT
S   S   A   L   A   A   P   V   N   T   T   T   E   D   E   T

GCT CAA ATT CCT GCT GAG GCT GTC ATC GGT TAC TCT GAC TTG GAA GGT
A   Q   I   P   A   E   A   V   I   G   Y   S   D   L   E   G

GAC TTC GAC GTC GCT GTT TTG CCA TTC TCT AAC TCT ACT AAC AAC GGT
D   F   D   V   A   V   L   P   F   S   N   S   T   N   N   G

TTG TTG TTC ATC AAC ACT ACC ATC GCT TCT ATC GCT GCT AAG GAG GAA
L   L   F   I   N   T   T   I   A   S   I   A   A   K   E   E

GGT GTT TCC CTC GAG AAG AGA GAG GCT ATG CAC TCT TTC TGT GCT TTC
G   V   S   L   E   K   R   E   A   M   H   S   F   C   A   F

AAG GCT GAC GAC GGT CCG TGC AGA GCT GCT CAC CCA AGA TGG TTC TTC
K   A   D   D   G   P   C   R   A   A   H   P   R   W   F   F

AAC ATC TTC ACG CGT CAA TGC GAG GAG TTC ATC TAC GGT GGT TGT GAG
N   I   F   T   R   Q   C   E   E   F   I   Y   G   G   C   E

GGT AAC CAA AAC AGA TTC GAG TCT CTA GAG GAG TGT AAG AAG ATG TGT
G   N   Q   N   R   F   E   S   L   E   E   C   K   K   M   C
                            EcoR I
ACT AGA GAC TAG TAA GAA TTC GCC TTA GAC ATG ACT GTT CCT CAG TTC
T   R   D   *   *                                   <--------
                                                          3'AOX1
AAG TTG GGC ACT TAC GAG AAG
           3'AOX1
```

FIGURE 2

```
SEQ ID 2:   (amino acids 3-60)  ----MHSFCAFKA-DDGPCRAAHPRWFFNIFTRQCEEFIYGG
SEQ ID 4:                       ----MHSFCAFKA-DDGPCKANHLRFFFNIFTRQCEEFSYGG
SEQ ID 5:                       ----MHSFCAFKA-DDGHCKANHQRFFFNIFTRQCEEFTYGG
SEQ ID 6:                       ----MHSFCAFKA-DDGHCKANHQRFFFNIFTRQCEQFTYGG
SEQ ID 7:                       ----MHSFCAFKA-DDGHCKASLPRFFFNIFTRQCEEFIYGG
SEQ ID 8:                       ----MHSFCAFKA-DDGHCKANHQRFFFNIFTRQCEEFSYGG
SEQ ID 9:                       ----MHSFCAKFA-DDGHCKGAHLRFFFNIFTRQCEEFIYGG
SEQ ID 10:                      ----MHSFCAFKA-DDGRCKGAHLRFFFNIFTRQCEEFIYGG
SEQ ID 11:                      ----MHSFCAFKA-DGGRCRGAHPRWFFNIFTRQCEEFSYGG
SEQ ID 12:                      ----MHSFCAFKA-DDGPCRAAHPRWFFNIFTRQCEEFSYGG
SEQ ID 13:                      ----MHSFCAFKA-DVGRCRGAHPRWFFNIFTRQCEEFSYGG
SEQ ID 14:                      ----MHSFCAFKA-DVGRCRGAQPRFFFNIFTRQCEEFSYGG
SEQ ID 15:                      ----MHSFCAFKA-DDGSCRAAHLRWFFNIFTRQCEEFSYGG
SEQ ID 16:                      ----MHSFCAFKA-EGGSCRAAHQRWFFNIFTRQCEEFSYGG
SEQ ID 17:                      ----MHSFCAFKA-DDGPCRGAHLRFFFNIFTRQCEEFSYGG
SEQ ID 18:                      ----MHSFCAFKA-DDGHCRGALPRWFFNIFTRQCEEFSYGG
SEQ ID 19:                      ----MHSFCAFKA-DSGNCRGNLPRFFFNIFTRQCEEFSYGG
SEQ ID 20:                      ----MHSFCAFKA-DSGRCRGNHQRFFFNIFTRQCEEFSYGG
SEQ ID 21:                      ----MHSFCAFKA-DGGRCRAIQPRWFFNIFTRQCEEFSYGG
SEQ ID 22:                      ----MHSFCAFKA-DDGRCRGAHPRWFFNIFTRQCEEFSYGG
BPTI (SEQ ID 29):               ----RPDFCLEPP-YTGPCKARIIRYFYNAKAGLCQTFVYGG
ITI-D1 (SEQ ID 30):             ----KEDSCQLGY-SAGPCMGMTSRYFYNGTSMACETFQYGG
ITI-D2 (SEQ ID 31):             ----TVAACNLPI-VRGPCRAFIQLWAFDAVKGKCVLFPYGG
LACI-D1 (SEQ ID 32):            ----MHSFCAFKA-DDGPCKAIMKRFFFNIFTRQCEEFIYGG
LACI-D2 (SEQ ID 33):            -----KPDFCFLEE-DPGICRGYITRYFYNNQTKQCERFKYGG
LACI-D3 (SEQ ID 34):            -----GPSWCLTPA-DRGLCRANENRFYYNSVIGKCRPFKYSG
HKI B9 (SEQ ID 35):             -----LPNVCAFPM-EKGPCQTYMTRWFFNFETGECELFAYGG
Cα3 (SEQ ID 36):                -----ETDICKLPK-DEGTCRDFILKWYYDPNTKSCARFWYGG
TFPI-2 D1 (SEQ ID 37):          -----NAEICLLPL-DYGPCRALLLRYYYDRYTQSCRQFLYGG
TFPI-2 D2 (SEQ ID 38):          -----VPKVCRLQVSVDDQCEGSTEKYFPNLSSMTCEKFFSGG
TFPI-2 D3 (SEQ ID 39):          -----IPSFCYSPK-DEGLCSANVTRYYFNPRYRTCDAFTYTG
APP-I (SEQ ID 40):              ---RNREVCSEQA-ETGPCRAMISRWYFDVTEGKCAPFFYGG
EpiNE7 (SEQ ID 41):             ----RPDFCLEPP-YTGPCVAMFPRYFYNAKAGLCQTFVYGG
BITI-E7-141 (SEQ ID 42):        ----RPDFCQLGY-SAGPCVAMFPRYFYNGTSMACQTFVYGG
MUTT26A (SEQ ID 43):            ----RPDFCQLGY-SAGPCVAMFPRYFYNGASMACQTFVYGG
MUTQE (SEQ ID 44):              ----RPDFCQLGY-SAGPCVAMFPRYFYNGTSMACETFVYGG
MUT1619 (SEQ ID 45):            ----RPDFCQLGY-SAGPCVGMFSRYFYNGTSMACQTFVYGG
EPI-HNE-1 (SEQ ID 46):          EAEARPDFCLEPP-YTGPCIAFFPRYFYNAKAGLCQTFVYGG
EPI-HNE-2 (SEQ ID 47):          ------AACNLPI-VRGPCIAFFPRWAFDAVKGKCVLFPYGG
EPI-HNE-3 (SEQ ID 48):          ------AACNLPI-VRGPCIAFFPRWAFDAVKGKCVLFPYGG
EPI-HNE-4 (SEQ ID 49):          ------EACNLPI-VRGPCIAFFPRWAFDAVKGKCVLFPYGG
DPI14 KR (SEQ ID 50):           --EAVREVCSEQA-ETGPCIAFFPRWYFDVTEGKCAPFFYGG
DPI24 KR (SEQ ID 51):           --EANAEICLLPL-DYGPCIAFFPRYYYDRYTQSCRQFLYGG
DPI68 KR (SEQ ID 52):           --EAKPDFCFLEE-DPGICIGFFPRYFYNNQAKQCERFVYGG
DPI84 KR (SEQ ID 53):           --EAETDICKLPK-DEGTCIAFFPRWYYDPNTKSCARFVYGG
```

FIGURE 3A

```
SEQ ID 2:       (cont.)                         CEGNQ--NRFESLEECKKMCTRD
SEQ ID 4:       (cont.)                         CGGNQ--NRFESLEECKKMCTRD
SEQ ID 5:       (cont.)                         CGGNQ--NRFESLEECKKMCTRD
SEQ ID 6:       (cont.)                         CAGNQ--NRFESLEECKKMCTRD
SEQ ID 7:       (cont.)                         CGGNQ--NRFESLEECKKMCTRD
SEQ ID 8:       (cont.)                         CGGNQ--NRFESLEECKKMCTRD
SEQ ID 9:       (cont.)                         CEGNQ--NRFESLEECKKMCTRD
SEQ ID 10:      (cont.)                         CEGNQ--NRFESLEECKKMCTRD
SEQ ID 11:      (cont.)                         CGGNQ--NRFESLEECKKMCTRD
SEQ ID 12:      (cont.)                         CGGNQ--NRFESLEECKKMCTRD
SEQ ID 13:      (cont.)                         CGGNQ--NRFESLEECKKMCTRD
SEQ ID 14:      (cont.)                         CGGNQ--NRFESLEECKKMCTRD
SEQ ID 15:      (cont.)                         CGGNQ--NRFESLEECKKMCTRD
SEQ ID 16:      (cont.)                         CGGNQ--NRFESLEECKKMCTRD
SEQ ID 17:      (cont.)                         CGGNQ--NRFESLEECKKMCTRD
SEQ ID 18:      (cont.)                         CGGNQ--NRFESLEECKKMCTRD
SEQ ID 19:      (cont.)                         CGGNQ--NRFESLEECKKMCTRD
SEQ ID 20:      (cont.)                         CGGNQ--NRFESLEECKKMCTRD
SEQ ID 21:      (cont.)                         CGGNQ--NRFESLEECKKMCTRD
SEQ ID 22:      (cont.)                         CGGNQ--NRFESLEECKKMCTRD
BPTI (SEQ ID 29):           (cont.)             CRAKR--NNFKSAEDCMRTCGGA
ITI-D1 (SEQ ID 30):         (cont.)             CMGNG--NNFVTEKECLQTCRTV
ITI-D2 (SEQ ID 31):         (cont.)             CQGNG--NKFYSEKECREYCGVP
LACI-D1 (SEQ ID 32):        (cont.)             CEGNQ--NRFESLEECKKMCTRD
LACI-D2 (SEQ ID 33):        (cont.)             CLGNM--NNFETLEECKNICEDG
LACI-D3 (SEQ ID 34):        (cont.)             CGGNE--NNFTSKQECLRACKKG
HKI B9 (SEQ ID 35):         (cont.)             CGGNS--NNFLRKEKCEKFCKFT
Cα3 (SEQ ID 36):            (cont.)             CGGNE--NKFGSQKECEKVCAPV
TFPI-2 D1 (SEQ ID 37):      (cont.)             CEGNA--NNFYTWEACDDACWRI
TFPI-2 D2 (SEQ ID 38):      (cont.)             CHRNRIENRFPDEATCMGFCAPK
TFPI-2 D3 (SEQ ID 39):      (cont.)             CGGND--NNFVSREDCKRACAKA
APP-I (SEQ ID 40):          (cont.)             CGGNR--NNFDTEEYCMAVCGSA
EpiNE7 (SEQ ID 41):         (cont.)             CMGNG--NNFKSAEDCMRTCGGA
BITI-E7-141 (SEQ ID 42):    (cont.)             CMGNG--NNFVTEKDCLQTCRGA
MUTT26A (SEQ ID 43):        (cont.)             CMGNG--NNFVTEKDCLQTCRGA
MUTQE (SEQ ID 44):          (cont.)             CMGNG--NNFVTEKDCLQTCRGA
MUT1619 (SEQ ID 45):        (cont.)             CMGNG--NNFVTEKDCLQTCRGA
EPI-HNE-1 (SEQ ID 46):      (cont.)             CMGNG--NNFKSAEDCMRTCGGA
EPI-HNE-2 (SEQ ID 47):      (cont.)             CQGNG--NKFYSEKECREYCGVP
EPI-HNE-3 (SEQ ID 48):      (cont.)             CQGNG--NKFYSEKECREYCGVP
EPI-HNE-4 (SEQ ID 49):      (cont.)             CQGNG--NKFYSEKECREYCGVP
DPI14 KR (SEQ ID 50):       (cont.)             CGGNR--NNFDTEEYCMAVCGSA
DPI24 KR (SEQ ID 51):       (cont.)             CEGNA--NNFYTWEACDDACWRI
DPI68 KR (SEQ ID 52):       (cont.)             CLGNM--NNFETLEECKNICEDG
DPI84 KR (SEQ ID 53):       (cont.)             CGGNE--NKFGSQKECEKVCAPV
```

FIGURE 3B

SEQUENCE LISTING

```
<160> NUMBER OF SEQ ID NOS: 57

<210> SEQ ID NO 1
<211> LENGTH: 58
<212> TYPE: PRT
<213> ORGANISM: Artificial Sequence
<220> FEATURE:
<223> OTHER INFORMATION: Polypeptide Inhibiting Kallikrein
<220> FEATURE:
<221> NAME/KEY: VARIANT
<222> LOCATION: 1, 2, 3, 4, 6, 7, 8, 9, 20, 24, 25, 26, 27, 28, 29, 41,
      42, 44, 46, 47, 48, 49, 50, 52, 53, 54, 56, 57, 58
<223> OTHER INFORMATION: Xaa = any amino acid
<220> FEATURE:
<221> NAME/KEY: VARIANT
<222> LOCATION: 10
<223> OTHER INFORMATION: Xaa = Asp or Glu
<220> FEATURE:
<221> NAME/KEY: VARIANT
<222> LOCATION: 11
<223> OTHER INFORMATION: Xaa = Asp, Gly, Ser, Val, Asn, Ile, Ala or Thr
<220> FEATURE:
<221> NAME/KEY: VARIANT
<222> LOCATION: 13
<223> OTHER INFORMATION: Xaa = Arg, His, Pro, Asn, Ser, Thr, Ala, Gly,
      Lys or Gln
<220> FEATURE:
<221> NAME/KEY: VARIANT
<222> LOCATION: 15
<223> OTHER INFORMATION: Xaa = Arg, Lys, Ala, Ser, Gly, Met, Asn or Gln
<220> FEATURE:
<221> NAME/KEY: VARIANT
<222> LOCATION: 16
<223> OTHER INFORMATION: Xaa = Ala, Gly, Ser, Asp or Asn
<220> FEATURE:
<221> NAME/KEY: VARIANT
<222> LOCATION: 17
<223> OTHER INFORMATION: Xaa = Ala, Asn, Ser, Ile, Gly, Val, Gln or Thr
<220> FEATURE:
<221> NAME/KEY: VARIANT
<222> LOCATION: 18
<223> OTHER INFORMATION: Xaa = His, Leu, Gln or Ala
```

```
<220> FEATURE:
<221> NAME/KEY: VARIANT
<222> LOCATION: 19
<223> OTHER INFORMATION: Xaa = Pro, Gln, Leu, Asn or Ile
<220> FEATURE:
<221> NAME/KEY: VARIANT
<222> LOCATION: 21
<223> OTHER INFORMATION: Xaa = Trp, Phe, Tyr, His or Ile
<220> FEATURE:
<221> NAME/KEY: VARIANT
<222> LOCATION: 22
<223> OTHER INFORMATION: Xaa = Tyr or Phe
<220> FEATURE:
<221> NAME/KEY: VARIANT
<222> LOCATION: 23
<223> OTHER INFORMATION: Xaa = Tyr or Phe
<220> FEATURE:
<221> NAME/KEY: VARIANT
<222> LOCATION: 31
<223> OTHER INFORMATION: Xaa = Glu, Asp, Gln, Asn, Ser, Ala, Val, Leu,
     Ile or Thr
<220> FEATURE:
<221> NAME/KEY: VARIANT
<222> LOCATION: 32
<223> OTHER INFORMATION: Xaa = Glu, Gln, Asp, Asn, Pro, Thr, Leu, Ser,
     Ala, Gly or Val
<220> FEATURE:
<221> NAME/KEY: VARIANT
<222> LOCATION: 34
<223> OTHER INFORMATION: Xaa = Thr, Ile, Ser, Val, Ala, Asn, Gly or Leu
<220> FEATURE:
<221> NAME/KEY: VARIANT
<222> LOCATION: 35
<223> OTHER INFORMATION: Xaa = Tyr, Trp or Phe
<220> FEATURE:
<221> NAME/KEY: VARIANT
<222> LOCATION: 39
<223> OTHER INFORMATION: Xaa = Glu, Gly, Ala, Ser or Asp
<220> FEATURE:
<221> NAME/KEY: VARIANT
<222> LOCATION: 40
<223> OTHER INFORMATION: Xaa = Gly, Ala,
<220> FEATURE:
<221> NAME/KEY: VARIANT
<222> LOCATION: 43
<223> OTHER INFORMATION: Xaa = Asn, Gly
<220> FEATURE:
<221> NAME/KEY: VARIANT
<222> LOCATION: 45
<223> OTHER INFORMATION: Xaa = Phe, Tyr

<400> SEQUENCE: 1

Xaa Xaa Xaa Xaa Cys Xaa Xaa Xaa Xaa Xaa Xaa Gly Xaa Cys Xaa Xaa
1               5                   10                  15

Xaa Xaa Xaa Xaa Xaa Xaa Xaa Xaa Xaa Xaa Xaa Xaa Xaa Cys Xaa Xaa
            20                  25                  30

Phe Xaa Xaa Gly Gly Cys Xaa Xaa Xaa Xaa Xaa Xaa Xaa Xaa Xaa
        35                  40                  45

Xaa Xaa Cys Xaa Xaa Xaa Cys Xaa Xaa Xaa
    50                  55

<210> SEQ ID NO 2
<211> LENGTH: 60
<212> TYPE: PRT
<213> ORGANISM: Artificial
<220> FEATURE:
<223> OTHER INFORMATION: Artificial Kunitz Domain
```

<400> SEQUENCE: 2

Glu Ala Met His Ser Phe Cys Ala Phe Lys Ala Asp Asp Gly Pro Cys
1               5                   10                  15

Arg Ala Ala His Pro Arg Trp Phe Phe Asn Ile Phe Thr Arg Gln Cys
            20                  25                  30

Glu Glu Phe Ile Tyr Gly Gly Cys Gly Gly Asn Gln Asn Arg Phe Glu
        35                  40                  45

Ser Leu Glu Glu Cys Lys Lys Met Cys Thr Arg Asp
    50                  55                  60

<210> SEQ ID NO 3
<211> LENGTH: 180
<212> TYPE: DNA
<213> ORGANISM: Artificial
<220> FEATURE:
<223> OTHER INFORMATION: Artificial Kunitz Domain coding sequence

<400> SEQUENCE: 3
gaggctatgc actctttctg tgctttcaag gctgacgacg gtccgtgcag agctgctcac       60
ccaagatggt tcttcaacat cttcacgcgt caatgcgagg agttcatcta cggtggttgt      120
gagggtaacc aaaacagatt cgagtctcta gaggagtgta agaagatgtg tactagagac      180

<210> SEQ ID NO 4
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 4

Met His Ser Phe Cys Ala Phe Lys Ala Asp Asp Gly Pro Cys Lys Ala
1               5                   10                  15

Asn His Leu Arg Phe Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 5
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 5

Met His Ser Phe Cys Ala Phe Lys Ala Asp Asp Gly His Cys Lys Ala
1               5                   10                  15

Asn His Gln Arg Phe Phe Phe Asn Ile Phe Thr Arg Gln Cys Glu Glu
            20                  25                  30

Phe Thr Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 6
<211> LENGTH: 58
<212> TYPE: PRT
<213> ORGANISM: Artificial Sequence

```
<220> FEATURE:
<223> OTHER INFORMATION: Synthetically generated peptide

<400> SEQUENCE: 6

Met His Ser Phe Cys Ala Phe Lys Ala Asp Asp Gly His Cys Lys Ala
1               5                   10                  15

Asn His Gln Arg Phe Phe Phe Asn Ile Phe Thr Arg Gln Cys Glu Gln
            20                  25                  30

Phe Thr Tyr Gly Gly Cys Ala Gly Asn Gln Asn Arg Phe Glu Ser Leu
        35                  40                  45

Glu Glu Cys Lys Lys Met Cys Thr Arg Asp
    50                  55

<210> SEQ ID NO 7
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 7

Met His Ser Phe Cys Ala Phe Lys Ala Asp Asp Gly His Cys Lys Ala
1               5                   10                  15

Ser Leu Pro Arg Phe Phe Phe Asn Ile Phe Thr Arg Gln Cys Glu Glu
            20                  25                  30

Phe Ile Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 8
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 8

Met His Ser Phe Cys Ala Phe Lys Ala Asp Asp Gly His Cys Lys Ala
1               5                   10                  15

Asn His Gln Arg Phe Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 9
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 9

Met His Ser Phe Cys Ala Phe Lys Ala Asp Asp Gly His Cys Lys Gly
1               5                   10                  15

Ala His Leu Arg Phe Phe Phe Asn Ile Phe Thr Arg Gln Cys Glu Glu
            20                  25                  30
```

```
Phe Ile Tyr Gly Gly Cys Glu Gly Asn Gln Asn Arg Phe Glu Ser Leu
        35                  40                  45

Glu Glu Cys Lys Lys Met Cys Thr Arg Asp
 50                  55

<210> SEQ ID NO 10
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 10

Met His Ser Phe Cys Ala Phe Lys Ala Asp Asp Gly Arg Cys Lys Gly
 1               5                  10                  15

Ala His Leu Arg Phe Phe Phe Asn Ile Phe Thr Arg Gln Cys Glu Glu
                20                  25                  30

Phe Ile Tyr Gly Gly Cys Glu Gly Asn Gln Asn Arg Phe Glu Ser Leu
        35                  40                  45

Glu Glu Cys Lys Lys Met Cys Thr Arg Asp
 50                  55

<210> SEQ ID NO 11
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 11

Met His Ser Phe Cys Ala Phe Lys Ala Asp Gly Gly Arg Cys Arg Gly
 1               5                  10                  15

Ala His Pro Arg Trp Phe Phe Asn Ile Phe Thr Arg Gln Cys Glu Glu
                20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
 50                  55

<210> SEQ ID NO 12
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 12

Met His Ser Phe Cys Ala Phe Lys Ala Asp Asp Gly Pro Cys Arg Ala
 1               5                  10                  15

Ala His Pro Arg Trp Phe Phe Asn Ile Phe Thr Arg Gln Cys Glu Glu
                20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
 50                  55

<210> SEQ ID NO 13
<211> LENGTH: 58
<212> TYPE: PRT
<213> ORGANISM: Artificial Sequence
<220> FEATURE:
<223> OTHER INFORMATION: Synthetically generated peptide
```

```
<400> SEQUENCE: 13

Met His Ser Phe Cys Ala Phe Lys Ala Asp Val Gly Arg Cys Arg Gly
1               5                   10                  15

Ala His Pro Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 14
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 14

Met His Ser Phe Cys Ala Phe Lys Ala Asp Val Gly Arg Cys Arg Gly
1               5                   10                  15

Ala Gln Pro Arg Phe Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 15
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 15

Met His Ser Phe Cys Ala Phe Lys Ala Asp Asp Gly Ser Cys Arg Ala
1               5                   10                  15

Ala His Leu Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 16
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 16

Met His Ser Phe Cys Ala Phe Lys Ala Glu Gly Gly Ser Cys Arg Ala
1               5                   10                  15

Ala His Gln Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55
```

-continued

```
<210> SEQ ID NO 17
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 17

Met His Ser Phe Cys Ala Phe Lys Ala Asp Asp Gly Pro Cys Arg Gly
1               5                   10                  15

Ala His Leu Arg Phe Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 18
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 18

Met His Ser Phe Cys Ala Phe Lys Ala Asp Asp Gly His Cys Arg Gly
1               5                   10                  15

Ala Leu Pro Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 19
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 19

Met His Ser Phe Cys Ala Phe Lys Ala Asp Ser Gly Asn Cys Arg Gly
1               5                   10                  15

Asn Leu Pro Arg Phe Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 20
<211> LENGTH: 58
<212> TYPE: PRT
<213> ORGANISM: Artificial Sequence
<220> FEATURE:
<223> OTHER INFORMATION: Synthetically generated peptide
```

<400> SEQUENCE: 20

Met His Ser Phe Cys Ala Phe Lys Ala Asp Ser Gly Arg Cys Arg Gly
1               5                   10                  15

Asn His Gln Arg Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
            35                  40                  45

Glu Glu Cys Lys Lys Met Cys Thr Arg Asp
    50                  55

<210> SEQ ID NO 21
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 21

Met His Ser Phe Cys Ala Phe Lys Ala Asp Gly Gly Arg Cys Arg Ala
1               5                   10                  15

Ile Gln Pro Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
            35                  40                  45

Glu Glu Cys Lys Lys Met Cys Thr Arg Asp
    50                  55

<210> SEQ ID NO 22
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 22

Met His Ser Phe Cys Ala Phe Lys Ala Asp Asp Gly Arg Cys Arg Gly
1               5                   10                  15

Ala His Pro Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
            35                  40                  45

Glu Glu Cys Lys Lys Met Cys Thr Arg Asp
    50                  55

<210> SEQ ID NO 23
<211> LENGTH: 6
<212> TYPE: DNA
<213> ORGANISM: Artificial Sequence
<220> FEATURE:
<223> OTHER INFORMATION: Modified Cloning Site

<400> SEQUENCE: 23 ttcgaa                                                          6

<210> SEQ ID NO 24
<211> LENGTH: 8
<212> TYPE: DNA
<213> ORGANISM: Artificial Sequence
<220> FEATURE:
<223> OTHER INFORMATION: Modified Cloning Site

```
<400> SEQUENCE: 24 ttcgcgaa                                                                       8

<210> SEQ ID NO 25
<211> LENGTH: 6
<212> TYPE: DNA
<213> ORGANISM: Artificial Sequence
<220> FEATURE:
<223> OTHER INFORMATION: Modified Cloning Site

<400> SEQUENCE: 25 gacgtc                                                                         6

<210> SEQ ID NO 26
<211> LENGTH: 10
<212> TYPE: DNA
<213> ORGANISM: Artificial Sequence
<220> FEATURE:
<223> OTHER INFORMATION: Modified Cloning Site

<400> SEQUENCE: 26
gacgtacgtc                                                                    10

<210> SEQ ID NO 27
<211> LENGTH: 548
<212> TYPE: DNA
<213> ORGANISM: Artificial Sequence
<220> FEATURE:
<223> OTHER INFORMATION: Nucleotide Sequence of Fusion Protein

<400> SEQUENCE: 27 cgactttaa cgacaacttg agaagatcaa aaaacaacta attattcgaa acgatgagat             60
tcccatctat cttcactgct gttttgttcg ctgcttcctc tgctttggct gctccagtta           120
acaccactac tgaagacgag actgctcaaa ttcctgctga ggctgtcatc ggttactctg           180
acttggaagg tgacttcgac gtcgctgttt tgccattctc taactctact aacaacggtt           240
tgttgttcat caacactacc atcgcttcta tcgctgctaa ggaggaaggt gtttccctcg           300
agaagagaga ggctatgcac tctttctgtg ctttcaaggc tgacgacggt ccgtgcagag           360
ctgctcaccc aagatggttc ttcaacatct tcacgcgtca atgcgaggag ttcatctacg           420
gtggttgtga gggtaaccaa aacagattcg agtctctaga ggagtgtaag aagatgtgta           480
ctagagacta gtaagaattc gccttagaca tgactgttcc tcagttcaag ttgggcactt           540
acgagaag                                                                   548

<210> SEQ ID NO 28
<211> LENGTH: 145
<212> TYPE: PRT
<213> ORGANISM: Artificial Sequence
<220> FEATURE:
<223> OTHER INFORMATION: Fusion Protein

<400> SEQUENCE: 28

Met Arg Phe Pro Ser Ile Phe Thr Ala Val Leu Phe Ala Ala Ser Ser
1               5                  10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60
```

```
Phe Ile Asn Thr Thr Ile Ala Ser Ile Ala Ala Lys Glu Glu Gly Val
 65                  70                  75                  80

Ser Leu Glu Lys Arg Glu Ala Met His Ser Phe Cys Ala Phe Lys Ala
                 85                  90                  95

Asp Asp Gly Pro Cys Arg Ala Ala His Pro Arg Trp Phe Phe Asn Ile
            100                 105                 110

Phe Thr Arg Gln Cys Glu Glu Phe Ile Tyr Gly Gly Cys Glu Gly Asn
        115                 120                 125

Gln Asn Arg Phe Glu Ser Leu Glu Glu Cys Lys Lys Met Cys Thr Arg
    130                 135                 140

Asp
145

<210> SEQ ID NO 29
<211> LENGTH: 58
<212> TYPE: PRT
<213> ORGANISM: Bos taurus

<400> SEQUENCE: 29

Arg Pro Asp Phe Cys Leu Glu Pro Pro Tyr Thr Gly Pro Cys Lys Ala
  1               5                  10                  15

Arg Ile Ile Arg Tyr Phe Tyr Asn Ala Lys Ala Gly Leu Cys Gln Thr
                 20                  25                  30

Phe Val Tyr Gly Gly Cys Arg Ala Lys Arg Asn Asn Phe Lys Ser Ala
             35                  40                  45

Glu Asp Cys Met Arg Thr Cys Gly Gly Ala
     50                  55

<210> SEQ ID NO 30
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 30

Lys Glu Asp Ser Cys Gln Leu Gly Tyr Ser Ala Gly Pro Cys Met Gly
  1               5                  10                  15

Met Thr Ser Arg Tyr Phe Tyr Asn Gly Thr Ser Met Ala Cys Glu Thr
                 20                  25                  30

Phe Gln Tyr Gly Gly Cys Met Gly Asn Gly Asn Asn Phe Val Thr Glu
             35                  40                  45

Lys Glu Cys Leu Gln Thr Cys Arg Thr Val
     50                  55

<210> SEQ ID NO 31
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 31

Thr Val Ala Ala Cys Asn Leu Pro Ile Val Arg Gly Pro Cys Arg Ala
  1               5                  10                  15

Phe Ile Gln Leu Trp Ala Phe Asp Ala Val Lys Gly Lys Cys Val Leu
                 20                  25                  30
```

Phe Pro Tyr Gly Gly Cys Gln Gly Asn Gly Asn Lys Phe Tyr Ser Glu
            35                  40                  45

Lys Glu Cys Arg Glu Tyr Cys Gly Val Pro
 50                  55

<210> SEQ ID NO 32
<211> LENGTH: 58
<212> TYPE: PRT
<213> ORGANISM: Homo sapiens

<400> SEQUENCE: 32

Met His Ser Phe Cys Ala Phe Lys Ala Asp Asp Gly Pro Cys Lys Ala
 1               5                   10                  15

Ile Met Lys Arg Phe Phe Phe Asn Ile Phe Thr Arg Gln Cys Glu Glu
                20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
 50                  55

<210> SEQ ID NO 33
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 33

Lys Pro Asp Phe Cys Phe Leu Glu Glu Asp Pro Gly Ile Cys Arg Gly
 1               5                   10                  15

Tyr Ile Thr Arg Tyr Phe Tyr Asn Asn Gln Thr Lys Gln Cys Glu Arg
                20                  25                  30

Phe Lys Tyr Gly Gly Cys Leu Gly Asn Met Asn Asn Phe Glu Thr Leu
            35                  40                  45

Glu Glu Cys Lys Asn Ile Cys Glu Asp Gly
 50                  55

<210> SEQ ID NO 34
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 34

Gly Pro Ser Trp Cys Leu Thr Pro Ala Asp Arg Gly Leu Cys Arg Ala
 1               5                   10                  15

Asn Glu Asn Arg Phe Tyr Tyr Asn Ser Val Ile Gly Lys Cys Arg Pro
                20                  25                  30

Phe Lys Tyr Ser Gly Cys Gly Asn Glu Asn Asn Phe Thr Ser Lys
            35                  40                  45

Gln Glu Cys Leu Arg Ala Cys Lys Lys Gly
 50                  55

<210> SEQ ID NO 35
<211> LENGTH: 58
<212> TYPE: PRT
<213> ORGANISM: Artificial Sequence
<220> FEATURE:
<223> OTHER INFORMATION: Synthetically generated peptide

```
<400> SEQUENCE: 35

Leu Pro Asn Val Cys Ala Phe Pro Met Glu Lys Gly Pro Cys Gln Thr
1               5                   10                  15

Tyr Met Thr Arg Trp Phe Phe Asn Phe Glu Thr Gly Glu Cys Glu Leu
            20                  25                  30

Phe Ala Tyr Gly Gly Cys Gly Gly Asn Ser Asn Asn Phe Leu Arg Lys
        35                  40                  45

Glu Lys Cys Glu Lys Phe Cys Lys Phe Thr
    50                  55

<210> SEQ ID NO 36
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 36

Glu Thr Asp Ile Cys Lys Leu Pro Lys Asp Glu Gly Thr Cys Arg Asp
1               5                   10                  15

Phe Ile Leu Lys Trp Tyr Tyr Asp Pro Asn Thr Lys Ser Cys Ala Arg
            20                  25                  30

Phe Trp Tyr Gly Gly Cys Gly Gly Asn Glu Asn Lys Phe Gly Ser Gln
        35                  40                  45

Lys Glu Cys Glu Lys Val Cys Ala Pro Val
    50                  55

<210> SEQ ID NO 37
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 37

Asn Ala Glu Ile Cys Leu Leu Pro Leu Asp Tyr Gly Pro Cys Arg Ala
1               5                   10                  15

Leu Leu Leu Arg Tyr Tyr Tyr Asp Arg Tyr Thr Gln Ser Cys Arg Gln
            20                  25                  30

Phe Leu Tyr Gly Gly Cys Glu Gly Asn Ala Asn Asn Phe Tyr Thr Trp
        35                  40                  45

Glu Ala Cys Asp Asp Ala Cys Trp Arg Ile
    50                  55

<210> SEQ ID NO 38
<211> LENGTH: 61
<212> TYPE: PRT
<213> ORGANISM: Artificial Sequence
<220> FEATURE:
<223> OTHER INFORMATION: Synthetically generated peptide

<400> SEQUENCE: 38

Val Pro Lys Val Cys Arg Leu Gln Val Ser Val Asp Asp Gln Cys Glu
1               5                   10                  15

Gly Ser Thr Glu Lys Tyr Phe Phe Asn Leu Ser Ser Met Thr Cys Glu
            20                  25                  30

Lys Phe Phe Ser Gly Gly Cys His Arg Asn Arg Ile Glu Asn Arg Phe
        35                  40                  45

Pro Asp Glu Ala Thr Cys Met Gly Phe Cys Ala Pro Lys
    50                  55                  60
```

```
<210> SEQ ID NO 39
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 39

Ile Pro Ser Phe Cys Tyr Ser Pro Lys Asp Glu Gly Leu Cys Ser Ala
1               5                   10                  15

Asn Val Thr Arg Tyr Tyr Phe Asn Pro Arg Tyr Arg Thr Cys Asp Ala
            20                  25                  30

Phe Thr Tyr Thr Gly Cys Gly Gly Asn Asp Asn Phe Val Ser Arg
        35                  40                  45

Glu Asp Cys Lys Arg Ala Cys Ala Lys Ala
    50                  55

<210> SEQ ID NO 40
<211> LENGTH: 59
<212> TYPE: PRT
<213> ORGANISM: Artificial Sequence
<220> FEATURE:
<223> OTHER INFORMATION: Synthetically generated peptide

<400> SEQUENCE: 40

Arg Asn Arg Glu Val Cys Ser Glu Gln Ala Glu Thr Gly Pro Cys Arg
1               5                   10                  15

Ala Met Ile Ser Arg Trp Tyr Phe Asp Val Thr Glu Gly Lys Cys Ala
            20                  25                  30

Pro Phe Phe Tyr Gly Gly Cys Gly Gly Asn Arg Asn Asn Phe Asp Thr
        35                  40                  45

Glu Glu Tyr Cys Met Ala Val Cys Gly Ser Ala
    50                  55

<210> SEQ ID NO 41
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 41

Arg Pro Asp Phe Cys Leu Glu Pro Pro Tyr Thr Gly Pro Cys Val Ala
1               5                   10                  15

Met Phe Pro Arg Tyr Phe Tyr Asn Ala Lys Ala Gly Leu Cys Gln Thr
            20                  25                  30

Phe Val Tyr Gly Gly Cys Met Gly Asn Gly Asn Asn Phe Lys Ser Ala
        35                  40                  45

Glu Asp Cys Met Arg Thr Cys Gly Gly Ala
    50                  55

<210> SEQ ID NO 42
<211> LENGTH: 58
<212> TYPE: PRT
<213> ORGANISM: Artificial Sequence
<220> FEATURE:
<223> OTHER INFORMATION: Synthetically generated peptide
```

```
<400> SEQUENCE: 42

Arg Pro Asp Phe Cys Gln Leu Gly Tyr Ser Ala Gly Pro Cys Val Ala
1               5                   10                  15

Met Phe Pro Arg Tyr Phe Tyr Asn Gly Thr Ser Met Ala Cys Gln Thr
            20                  25                  30

Phe Val Tyr Gly Gly Cys Met Gly Asn Gly Asn Asn Phe Val Thr Glu
        35                  40                  45

Lys Asp Cys Leu Gln Thr Cys Arg Gly Ala
    50                  55

<210> SEQ ID NO 43
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 43

Arg Pro Asp Phe Cys Gln Leu Gly Tyr Ser Ala Gly Pro Cys Val Ala
1               5                   10                  15

Met Phe Pro Arg Tyr Phe Tyr Asn Gly Ala Ser Met Ala Cys Gln Thr
            20                  25                  30

Phe Val Tyr Gly Gly Cys Met Gly Asn Gly Asn Asn Phe Val Thr Glu
        35                  40                  45

Lys Asp Cys Leu Gln Thr Cys Arg Gly Ala
    50                  55

<210> SEQ ID NO 44
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 44

Arg Pro Asp Phe Cys Gln Leu Gly Tyr Ser Ala Gly Pro Cys Val Ala
1               5                   10                  15

Met Phe Pro Arg Tyr Phe Tyr Asn Gly Thr Ser Met Ala Cys Glu Thr
            20                  25                  30

Phe Val Tyr Gly Gly Cys Met Gly Asn Gly Asn Asn Phe Val Thr Glu
        35                  40                  45

Lys Asp Cys Leu Gln Thr Cys Arg Gly Ala
    50                  55

<210> SEQ ID NO 45
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 45

Arg Pro Asp Phe Cys Gln Leu Gly Tyr Ser Ala Gly Pro Cys Val Gly
1               5                   10                  15

Met Phe Ser Arg Tyr Phe Tyr Asn Gly Thr Ser Met Ala Cys Gln Thr
            20                  25                  30

Phe Val Tyr Gly Gly Cys Met Gly Asn Gly Asn Asn Phe Val Thr Glu
        35                  40                  45

Lys Asp Cys Leu Gln Thr Cys Arg Gly Ala
    50                  55
```

<210> SEQ ID NO 46
<211> LENGTH: 62
<212> TYPE: PRT
<213> ORGANISM: Artificial Sequence
<220> FEATURE:
<223> OTHER INFORMATION: Synthetically generated peptide

<400> SEQUENCE: 46

Glu Ala Glu Ala Arg Pro Asp Phe Cys Leu Glu Pro Pro Tyr Thr Gly
1               5                   10                  15

Pro Cys Ile Ala Phe Phe Pro Arg Tyr Phe Tyr Asn Ala Lys Ala Gly
            20                  25                  30

Leu Cys Gln Thr Phe Val Tyr Gly Gly Cys Met Gly Asn Gly Asn Asn
        35                  40                  45

Phe Lys Ser Ala Glu Asp Cys Met Arg Thr Cys Gly Gly Ala
    50                  55                  60

<210> SEQ ID NO 47
<211> LENGTH: 56
<212> TYPE: PRT
<213> ORGANISM: Artificial Sequence
<220> FEATURE:
<223> OTHER INFORMATION: Synthetically generated peptide

<400> SEQUENCE: 47

Ala Ala Cys Asn Leu Pro Ile Val Arg Gly Pro Cys Ile Ala Phe Phe
1               5                   10                  15

Pro Arg Trp Ala Phe Asp Ala Val Lys Gly Lys Cys Val Leu Phe Pro
            20                  25                  30

Tyr Gly Gly Cys Gln Gly Asn Gly Asn Lys Phe Tyr Ser Glu Lys Glu
        35                  40                  45

Cys Arg Glu Tyr Cys Gly Val Pro
    50                  55

<210> SEQ ID NO 48
<211> LENGTH: 56
<212> TYPE: PRT
<213> ORGANISM: Artificial Sequence
<220> FEATURE:
<223> OTHER INFORMATION: Synthetically generated peptide

<400> SEQUENCE: 48

Ala Ala Cys Asn Leu Pro Ile Val Arg Gly Pro Cys Ile Ala Phe Phe
1               5                   10                  15

Pro Arg Trp Ala Phe Asp Ala Val Lys Gly Lys Cys Val Leu Phe Pro
            20                  25                  30

Tyr Gly Gly Cys Gln Gly Asn Gly Asn Lys Phe Tyr Ser Glu Lys Glu
        35                  40                  45

Cys Arg Glu Tyr Cys Gly Val Pro
    50                  55

<210> SEQ ID NO 49
<211> LENGTH: 56
<212> TYPE: PRT
<213> ORGANISM: Artificial Sequence
<220> FEATURE:
<223> OTHER INFORMATION: Synthetically generated peptide

<400> SEQUENCE: 49

Glu Ala Cys Asn Leu Pro Ile Val Arg Gly Pro Cys Ile Ala Phe Phe
1               5                   10                  15

Pro Arg Trp Ala Phe Asp Ala Val Lys Gly Lys Cys Val Leu Phe Pro
            20                  25                  30

Tyr Gly Gly Cys Gln Gly Asn Gly Asn Lys Phe Tyr Ser Glu Lys Glu
        35                  40                  45

Cys Arg Glu Tyr Cys Gly Val Pro
    50                  55

<210> SEQ ID NO 50
<211> LENGTH: 60
<212> TYPE: PRT
<213> ORGANISM: Artificial Sequence
<220> FEATURE:
<223> OTHER INFORMATION: Synthetically generated peptide

<400> SEQUENCE: 50

Glu Ala Val Arg Glu Val Cys Ser Glu Gln Ala Glu Thr Gly Pro Cys
1               5                   10                  15

Ile Ala Phe Phe Pro Arg Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
        35                  40                  45

Thr Glu Glu Tyr Cys Met Ala Val Cys Gly Ser Ala
    50                  55                  60

<210> SEQ ID NO 51
<211> LENGTH: 60
<212> TYPE: PRT
<213> ORGANISM: Artificial Sequence
<220> FEATURE:
<223> OTHER INFORMATION: Synthetically generated peptide

<400> SEQUENCE: 51

Glu Ala Asn Ala Glu Ile Cys Leu Leu Pro Leu Asp Tyr Gly Pro Cys
1               5                   10                  15

Ile Ala Phe Phe Pro Arg Tyr Tyr Tyr Asp Arg Tyr Thr Gln Ser Cys
            20                  25                  30

Arg Gln Phe Leu Tyr Gly Gly Cys Glu Gly Asn Ala Asn Asn Phe Tyr
        35                  40                  45

Thr Trp Glu Ala Cys Asp Asp Ala Cys Trp Arg Ile
    50                  55                  60

<210> SEQ ID NO 52
<211> LENGTH: 60
<212> TYPE: PRT
<213> ORGANISM: Artificial Sequence
<220> FEATURE:
<223> OTHER INFORMATION: Synthetically generated peptide

<400> SEQUENCE: 52

Glu Ala Lys Pro Asp Phe Cys Phe Leu Glu Glu Asp Pro Gly Ile Cys
1               5                   10                  15

Ile Gly Phe Phe Pro Arg Tyr Phe Tyr Asn Asn Gln Ala Lys Gln Cys
            20                  25                  30

Glu Arg Phe Val Tyr Gly Gly Cys Leu Gly Asn Met Asn Asn Phe Glu
        35                  40                  45

Thr Leu Glu Glu Cys Lys Asn Ile Cys Glu Asp Gly
    50                  55                  60

```
<210> SEQ ID NO 53
<211> LENGTH: 60
<212> TYPE: PRT
<213> ORGANISM: Artificial Sequence
<220> FEATURE:
<223> OTHER INFORMATION: Synthetically generated peptide

<400> SEQUENCE: 53

Glu Ala Glu Thr Asp Ile Cys Lys Leu Pro Lys Asp Glu Gly Thr Cys
1               5                   10                  15
Ile Ala Phe Phe Pro Arg Trp Tyr Tyr Asp Pro Asn Thr Lys Ser Cys
                20                  25                  30
Ala Arg Phe Val Tyr Gly Gly Cys Gly Gly Asn Glu Asn Lys Phe Gly
            35                  40                  45
Ser Gln Lys Glu Cys Glu Lys Val Cys Ala Pro Val
    50                  55                  60

<210> SEQ ID NO 54
<211> LENGTH: 304
<212> TYPE: PRT
<213> ORGANISM: Homo sapiens

<400> SEQUENCE: 54

Met Ile Tyr Thr Met Lys Lys Val His Ala Leu Trp Ala Ser Val Cys
1               5                   10                  15
Leu Leu Leu Asn Leu Ala Pro Ala Pro Leu Asn Ala Asp Ser Glu Glu
                20                  25                  30
Asp Glu Glu His Thr Ile Ile Thr Asp Thr Glu Leu Pro Pro Leu Lys
            35                  40                  45
Leu Met His Ser Phe Cys Ala Phe Lys Ala Asp Asp Gly Pro Cys Lys
    50                  55                  60
Ala Ile Met Lys Arg Phe Phe Phe Asn Ile Phe Thr Arg Gln Cys Glu
65                  70                  75                  80
Glu Phe Ile Tyr Gly Gly Cys Glu Gly Asn Gln Asn Arg Phe Glu Ser
                85                  90                  95
Leu Glu Glu Cys Lys Lys Met Cys Thr Arg Asp Asn Ala Asn Arg Ile
            100                 105                 110
Ile Lys Thr Thr Leu Gln Gln Glu Lys Pro Asp Phe Cys Phe Leu Glu
    115                 120                 125
Glu Asp Pro Gly Ile Cys Arg Gly Tyr Ile Thr Arg Tyr Phe Tyr Asn
130                 135                 140
Asn Gln Thr Lys Gln Cys Glu Arg Phe Lys Tyr Gly Gly Cys Leu Gly
145                 150                 155                 160
Asn Met Asn Asn Phe Glu Thr Leu Glu Glu Cys Lys Asn Ile Cys Glu
                165                 170                 175
Asp Gly Pro Asn Gly Phe Gln Val Asp Asn Tyr Gly Thr Gln Leu Asn
            180                 185                 190
Ala Val Asn Asn Ser Leu Thr Pro Gln Ser Thr Lys Val Pro Ser Leu
    195                 200                 205
Phe Glu Phe His Gly Pro Ser Trp Cys Leu Thr Pro Ala Asp Arg Gly
210                 215                 220
Leu Cys Arg Ala Asn Glu Asn Arg Phe Tyr Tyr Asn Ser Val Ile Gly
225                 230                 235                 240
Lys Cys Arg Pro Phe Lys Tyr Ser Gly Cys Gly Gly Asn Glu Asn Asn
                245                 250                 255
Phe Thr Ser Lys Gln Glu Cys Leu Arg Ala Cys Lys Lys Gly Phe Ile
            260                 265                 270
```

```
Gln Arg Ile Ser Lys Gly Gly Leu Ile Lys Thr Lys Arg Lys Arg Lys
            275                 280                 285

Lys Gln Arg Val Lys Ile Ala Tyr Glu Glu Ile Phe Val Lys Asn Met
        290                 295                 300

<210> SEQ ID NO 55
<211> LENGTH: 58
<212> TYPE: PRT
<213> ORGANISM: Bos taurus

<400> SEQUENCE: 55

Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
    50                  55

<210> SEQ ID NO 56
<211> LENGTH: 58
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 10
<223> OTHER INFORMATION: Xaa = Asp or Glu
<220> FEATURE:
<221> NAME/KEY: VARIANT
<222> LOCATION: 11
<223> OTHER INFORMATION: Xaa = Asp, Gly, Ser, Val, Asn, Ile, Ala or Thr
<220> FEATURE:
<221> NAME/KEY: VARIANT
<222> LOCATION: 13
<223> OTHER INFORMATION: Xaa = Arg, His, Pro, Asn, Ser, Thr, Ala, Gly,
     Lys or Gln
<220> FEATURE:
<221> NAME/KEY: VARIANT
<222> LOCATION: 15
<223> OTHER INFORMATION: Xaa = Arg, Ala, Ser, Gly, Met, Asn or Gln
<220> FEATURE:
<221> NAME/KEY: VARIANT
<222> LOCATION: 16
<223> OTHER INFORMATION: Xaa = Ala, Gly, Ser, Asp or Asn
<220> FEATURE:
<221> NAME/KEY: VARIANT
<222> LOCATION: 17
<223> OTHER INFORMATION: Xaa = Ala, Asn, Ser, Ile, Gly, Val, Gln or Thr
<220> FEATURE:
<221> NAME/KEY: VARIANT
<222> LOCATION: 18
<223> OTHER INFORMATION: Xaa = His, Leu, Gln or Ala
<220> FEATURE:
<221> NAME/KEY: VARIANT
<222> LOCATION: 19
<223> OTHER INFORMATION: Xaa = Pro, Gln, Leu, Asn or Ile
<220> FEATURE:
<221> NAME/KEY: VARIANT
<222> LOCATION: 21
<223> OTHER INFORMATION: Xaa = Trp, Phe, Tyr, His or Ile
<220> FEATURE:
<221> NAME/KEY: VARIANT
<222> LOCATION: 31
<223> OTHER INFORMATION: Xaa = Glu, Asp, Gln, Asn, Ser, Ala, Val, Leu,
     Ile or Thr
```

```
<220> FEATURE:
<221> NAME/KEY: VARIANT
<222> LOCATION: 32
<223> OTHER INFORMATION: Xaa = Glu, Gln, Asp, Asn, Pro, Thr, Leu, Ser,
      Ala, Gly or Val
<220> FEATURE:
<221> NAME/KEY: VARIANT
<222> LOCATION: 34
<223> OTHER INFORMATION: Xaa = Thr, Ile, Ser, Val, Ala, Asn, Gly or Leu
<220> FEATURE:
<221> NAME/KEY: VARIANT
<222> LOCATION: 35
<223> OTHER INFORMATION: Xaa = Tyr, Trp or Phe
<220> FEATURE:
<221> NAME/KEY: VARIANT
<222> LOCATION: 39
<223> OTHER INFORMATION: Xaa = Glu, Gly, Ala, Ser or Asp

<400> SEQUENCE: 56

Met His Ser Phe Cys Ala Phe Lys Ala Xaa Xaa Gly Xaa Cys Xaa Xaa
1               5                   10                  15

Xaa Xaa Xaa Arg Xaa Phe Phe Asn Ile Phe Thr Arg Gln Cys Xaa Xaa
            20                  25                  30

Phe Xaa Xaa Gly Gly Cys Xaa Gly Asn Gln Asn Arg Phe Glu Ser Leu
        35                  40                  45

Glu Glu Cys Lys Lys Met Cys Thr Arg Asp
    50                  55

<210> SEQ ID NO 57
<211> LENGTH: 58
<212> TYPE: PRT
<213> ORGANISM: Artificial
<220> FEATURE:
<223> OTHER INFORMATION: Synthetically generated peptide

<400> SEQUENCE: 57

Met His Ser Phe Cys Ala Phe Lys Ala Asp Asp Gly Pro Cys Arg Ala
1               5                   10                  15

Ala His Pro Arg Trp Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
        35                  40                  45

Glu Glu Cys Lys Lys Met Cys Thr Arg Asp
    50                  55
```

KALLIKREIN-INHIBITOR THERAPIES

CROSS-REFERENCE TO RELATED APPLICATIONS

This application is continuation of U.S. patent application Ser. No. 11/929,822, filed Oct. 30, 2007 (allowed), which is a continuation of U.S. patent application Ser. No. 11/466,979, filed Aug. 24, 2006 (now U.S. Pat. No. 7,704,949), which is a continuation of U.S. patent application Ser. No. 10/953,902, filed on Sep. 27, 2004 (now U.S. Pat. No. 7,153,829), which is a continuation-in-part of U.S. patent application Ser. No. 10/456,986, filed Jun. 6, 2003, (now U.S. Pat. No. 7,064,107), which claims priority to U.S. provisional application No. 60/387,239, filed on Jun. 7, 2002, and 60/407,003, filed on Aug. 28, 2002, the contents of all of which are incorporated herein by reference.

SUMMARY

Serine proteases such as, kallikrein (e.g., plasma kallikrein), are involved in pathways leading to excessive perioperative blood loss, the onset of systemic inflammatory response and nervous system pathophysiology. Inhibitors of kallikrein include proteinaceous and non-proteinaceous molecules. Exemplary plasma kallikrein inhibitors include those described in U.S. Pat. Nos. 6,333,402 and 6,057,287, the contents of which are incorporated herein by reference in their entirety.

Polypeptide and other inhibitors of plasma kallikrein can be used in therapeutic methods and compositions suitable for use in eliminating or reducing various ischemias, including but not limited to perioperative blood loss, cerebral ischemia, the onset of systemic inflammatory response, and/or reperfusion injury, e.g., reperfusion injury associated with cerebral ischemia or a focal brain ischemia. Perioperative blood loss results from invasive surgical procedures that lead to contact activation of complement components and the coagulation/fibrinolysis systems. The kallikrein inhibitors can be used to reduce or prevent perioperative blood loss and a systemic inflammatory response in patients subjected to invasive surgical procedures, especially cardiothoracic surgeries. The kallikrein inhibitors can also be used to reduce or prevent cerebral ischemia such as stroke, and/or reperfusion injury associated with cerebral ischemia. They can also prevent neurological and cognitive deficits associated with stroke, blood lose, and cerebral ischemia, e.g., events that are not associated with surgical intervention. The inhibitors can be administered prior to, during, or after an event, e.g., a cardiovascular event that can damage the central nervous system.

A variety of inhibitors of a kallikrein, e.g., a plasma kallikrein are described herein. Any one of these, or a combination of more than one of these, can be used in the following methods.

In one aspect, the disclosure features a method for preventing or reducing ischemia in a patient including administering to the patient a composition that includes an inhibitor of kallikrein, e.g., a plasma kallikrein. Typically the patient is a human patient. The composition can be administered in an amount effective to prevent or reduce ischemia in the patient. In a particular embodiment, the ischemia is at least partially due to blood loss, e.g., perioperative blood loss due to a surgical procedure performed on the patient. The surgical procedure can be, e.g., a cardiothoracic surgery, such as, for example, cardiopulmonary bypass or coronary artery bypass grafting. The inhibitor can be administered before, during, or after the procedure.

In another aspect, the disclosure features a method for preventing or reducing a systemic inflammatory response, e.g., a response associated with a surgical procedure in a patient or its onset. The method includes: administering to the patient a composition including an inhibitor of kallikrein, e.g., a plasma kallikrein. The composition can be administered before, during, or after surgery. In one embodiment, the surgical procedure is a cardiothoracic surgery, such as, for example, cardiopulmonary bypass or coronary artery bypass grafting.

In another aspect, the disclosure features a method for treating a brain or central nervous system (CNS) injury. The method can be used to prevent or reduce adverse effects of cerebral ischemia, e.g., stroke, and/or reperfusion injury, e.g., reperfusion injury associated with cerebral ischemia, in a patient including administering to the patient a composition including an inhibitor of kallikrein, e.g., a plasma kallikrein. In one embodiment, the cerebral ischemia is stroke, e.g., embolism-, thrombus- or hemorrhage-associated stroke. The method can include administering the inhibitor, before, during, or after the ischemia, e.g., at the time of reperfusion or at a time between 1-12 hours after an ischemic event, e.g., between 1-5 hours after such an event.

The inhibitor used in any disclosed method can have a Ki for kallikrein, e.g., plasma kallikrein of less than 50 nM, 5 nM, 1 nM, 500 pM, 100 pM, 50 pM, e.g., about 44 pM. The inhibitor can preferentially inhibit plasma kallikrein at least 100, 200, 500, or 1000 more than another kallikrein, e.g., human urine kallikrein, or another protease, e.g., plasmin or thrombin. For example, the inhibitor is other than aprotinin.

In one embodiment, the inhibitor is an agent that can cross the blood-brain barrier.

In one embodiment, the inhibitor includes a polypeptide that includes a Kunitz domain such as the amino acid sequence: Xaa1 Xaa2 Xaa3 Xaa4 Cys Xaa6 Xaa7 Xaa8 Xaa9 Xaa10 Xaa11 Gly Xaa13 Cys Xaa15 Xaa16 Xaa17 Xaa18 Xaa19 Xaa20 Xaa91 Xaa22 Xaa23 Xaa24 Xaa25 Xaa26 Xaa27 Xaa28 Xaa29 Cys Xaa31 Xaa32 Phe Xaa34 Xaa35 Gly Gly Cys Xaa39 Xaa40 Xaa41 Xaa42 Xaa43 Xaa44 Xaa45 Xaa46 Xaa47 Xaa48 Xaa49 Xaa50 Cys Xaa52 Xaa53 Xaa54 Cys Xaa56 Xaa57 Xaa58 (SEQ ID NO:1).

The framework of the Kunitz domain can be human or can differ from a human Kunitz domain framework by fewer than six, five, four, three, or two amino acids. For example, the framework of the Kunitz domain can be the framework of one of the Kunitz domains of human lipoprotein-associated coagulation inhibitor (LACI) protein, e.g., the first second or third Kunitz domain. Typically the polypeptide differs from BPTI and/or one or more of the LACI Kunitz domains by at least one, two, three, or four amino acids, e.g., at least one, two or three amino acids in the binding loops and/or at least two, three, four, or six amino acids in the framework region. For example, the polypeptide can include a non-naturally occurring Kunitz domain that is derived from a naturally occurring Kunitz domain, e.g., a human Kunitz domain. In one embodiment, an inhibitor that includes a Kunitz domain binds to plasma kallikrein with an affinity that is at least 10, 100, or 500 fold better than BPTI and/or LACI.

In one embodiment, the polypeptide that inhibits kallikrein is not immunogenic on second use.

In one embodiment, the polypeptide can have one or more of the following features: Xaa1, Xaa2, Xaa3, Xaa4, Xaa56, Xaa57 or Xaa58 are each individually an amino acid or absent; Xaa10 is an amino acid selected from the group consisting of: Asp and Glu; Xaa11 is an amino acid selected from the group consisting of: Asp, Gly, Ser, Val, Asn, Ile, Ala and Thr; Xaa13 is an amino acid selected from the group consisting of: Arg, His, Pro, Asn, Ser, Thr, Ala, Gly, Lys and Gln; Xaa15 is an amino acid selected from the group consisting of: Arg, Lys, Ala, Ser, Gly, Met, Asn and Gln; Xaa16 is an amino acid selected from the group consisting of Ala, Gly, Ser, Asp and Asn; Xaa17 is an amino acid selected from the group consisting of: Ala, Asn, Ser, Ile, Gly, Val, Gln and Thr; Xaa18 is an amino acid selected from the group consisting of: His, Leu, Gln and Ala; Xaa19 is an amino acid selected from the group consisting of: Pro, Gln, Leu, Asn and Ile; Xaa21 is an amino acid selected from the group consisting of: Trp, Phe, Tyr, His and Ile; Xaa22 is an amino acid selected from the group consisting of: Tyr and Phe; Xaa23 is an amino acid selected from the group consisting of Tyr and Phe; Xaa31 is an amino acid selected from the group consisting of: Glu, Asp, Gln, Asn, Ser, Ala, Val, Len, Ile and Thr; Xaa32 is an amino acid selected from the group consisting of: Glu, Gln, Asp Asn, Pro, Thr, Leu, Ser, Ala, Gly and Val; Xaa34 is an amino acid selected from the group consisting of: Thr, Ile, Ser, Val, Ala, Asn, Gly and Leu; Xaa35 is an amino acid selected from the group consisting of Tyr, Trp and Phe; Xaa39 is an amino acid selected from the group consisting of: Glu, Gly, Ala, Ser and Asp; Xaa40 is an amino acid selected from the group consisting of Gly and Ala; Xaa43 is an amino acid selected from the group consisting of Asn and Gly; Xaa45 is an amino acid selected from the group consisting of: Phe and Tyr; and wherein the polypeptide inhibits kallikrein.

In a particular embodiment, individual amino acid positions of SEQ ID NO:1 can be one or more of the following: Xaa10 is Asp, Xaa11 is Asp, Xaa13 is Pro, Xaa15 is Arg, Xaa16 is Ala, Xaa17 is Ala, Xaa18 is His, Xaa19 is Pro, Xaa21 is Trp, Xaa31 is Glu, Xaa32 is Glu, Xaa34 is Ile, Xaa35 is Tyr, Xaa39 is Glu.

The polypeptide can include (or consist of) the following amino acid sequence: Glu Ala Met His Ser Phe Cys Ala Phe Lys Ala Asp Asp Gly Pro Cys Arg Ala Ala His Pro Arg Tip Phe Phe Asn Ile Phe Thr Arg Gln Cys Glu Glu Phe Ile Tyr Gly Gly Cys Glu Gly Asn Gln Asn Arg Phe Glu Ser Leu Glu Gln Cys Lys Lys Met Cys Thr Arg Asp (SEQ ID NO:2), or a fragment thereof, e.g., amino acids 3-60 of SEQ ID NO:2 or other fragment that binds and inhibits kallikrein. For example, the polypeptide can have fewer than 80, 70, 65, or 60 amino acids.

In one embodiment, the polypeptide is modified, e.g., to include one or more polymer moieties, e.g., a plurality of polymer moieties, e.g., as described in U.S. Ser. No. 10/931,153, filed Aug. 30, 2004. For example, the polypeptide can include a plurality of polyethylene glycol moieties, e.g., one on an N-terminal amine and one attached to each lysine of the polypeptide. The polyethylene glycol moieties can be less than 10, 8, 7, or 6 kDa in average molecular weight. Other exemplary modifications include a label, e.g., a radioactive or MRI-detectable label.

In one embodiment, the inhibitor does not include a peptide or polypeptide. For example, the inhibitor can be small molecule, e.g., a compound described in WO 04/062657, e.g., an acylated 4-amidino- or 4-guanidinobenzylamines. The compound can have the general formula (I) P4-P3-P2-P1 (I), where P4 is a mono- or poly-substituted or unsubstituted benzylsulphonyl group, P3 is a mono- or poly-substituted or unsubstituted, natural or unnatural alpha-amino or alpha-imino acid with the D-configuration, P2 is a mono- or poly-substituted or unsubstituted natural or unnatural alpha-amino or alpha-imino acid with the L-configuration and P1 is a mono- or poly-substituted or unsubstituted 4-amidino- or 4-guanidinobenzylamine group.

The methods described herein can include administering an effective amount of the inhibitor of kallikrein. Such an amount can be an amount sufficient to produce an improvement detectable to one skilled in the art, to ameliorate at least one symptom, or to modulate (e.g., improve) at least one physiological parameter, e.g., to a statistically significant degree.

All patents, patent applications, and publications cited herein are incorporated herein by reference. In the case of conflict, the present application controls.

BRIEF DESCRIPTION OF THE DRAWINGS

FIG. 2 shows a portion of a DNA and corresponding deduced amino acid for an exemplary kallikrein inhibitor polypeptide in plasmid pPIC-K503. The inserted DNA encodes the matα Prepro signal peptide of Saccharomyces cerevisiae (underlined) fused in frame to the amino terminus of the PEP-1 polypeptide having the amino acid sequence enclosed by the boxed area. The amino acid sequence of the PEP-1 polypeptide shown in the boxed region is SEQ ID NO:2, and the corresponding nucleotide coding sequence is SEQ ID NO:3. The dashed arrows indicate the location and direction of two. PCR primer sequences in AOX regions that were used to produce sequencing templates. DNA sequence for the entire nucleotide sequence of the figure includes the structural coding sequence for the fusion protein and is designated SEQ ID NO:27. The double underlined portion of the sequence indicates a diagnostic probe sequence. BstB I and EcoR I indicate locations of their respective palindromic, hexameric, restriction endonuclease sites in the sequence. Asterisks denote translational stop codons. See text for details.

FIGS. 3A and 3B show an alignment of exemplary amino acid sequences, the native LACI sequence from which these variants were derived (SEQ ID NO:32), and other known Kunitz domains (SEQ ID NOS:29-31 and 33-53). Cysteine residues are highlighted.

DETAILED DESCRIPTION

Figure 1:
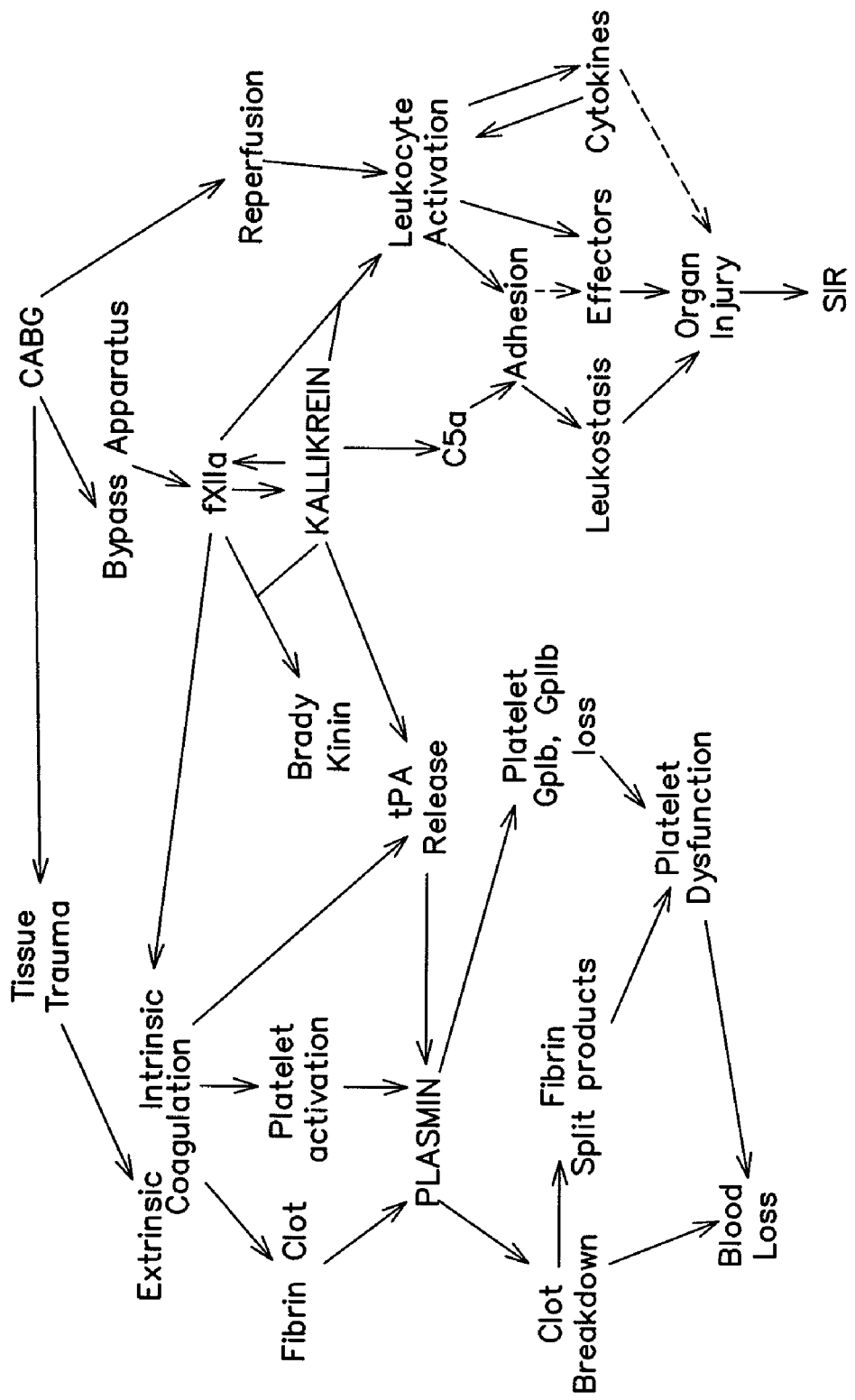
FIG. 1 is a simplified diagram of major multiple pathways and related events involved in the contact activation system and systemic inflammatory response (SIR) that may arise in a patient subjected to soft and bone tissue trauma such as that associated with a coronary artery bypass grafting (CABG) procedure, especially when the CABG procedure involves extra-corporeal blood circulation, such as cardiopulmonary bypass (Bypass Apparatus). Arrows indicate activation from one component or event to another component or event in the cascade. Arrows in both directions indicate activating effects of components or events in both directions. Broken arrows indicate likely participation of one component or event in the activation of another component or event. Abbreviations: "tPA", tissue plasminogen activator; "C5a", a protein component of the complement system; "fXIIa", activator protein of prekallikrein to form active kallikrein; "Extrinsic", extrinsic coagulation system; "Intrinsic", intrinsic coagulation system.
Figure 4:
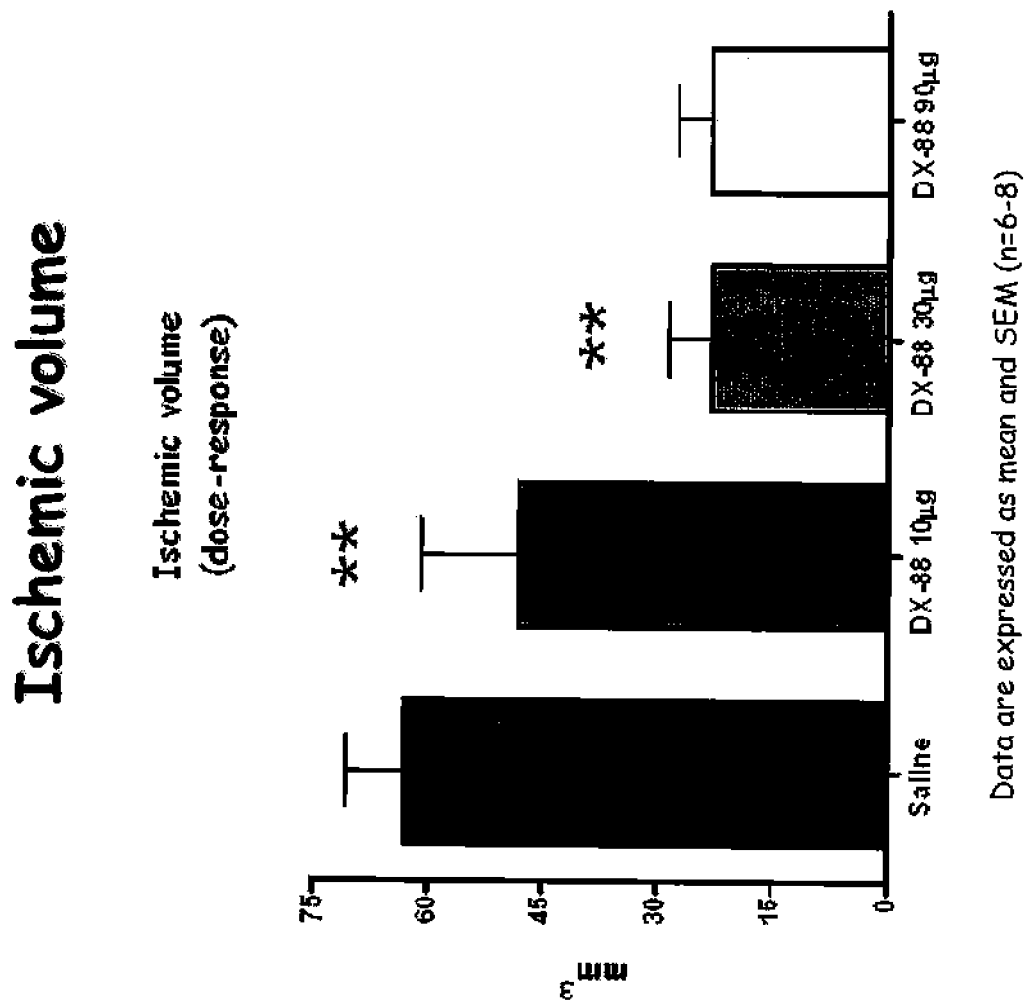
FIG. 4 is a graph depicting ischemic volume in C57B1/6 mice subjected to transient focal cerebral ischemia by middle cerebral artery occlusion (MCAO) using 5-0 microfilament and administered saline (control) or a kallikrein inhibitor polypeptide (DX-88) at various doses (10 µg, 30 µg, 90 µg). The saline or kallikrein inhibitor polypeptide was administered at the beginning of the ischemic period.
Figure 5:
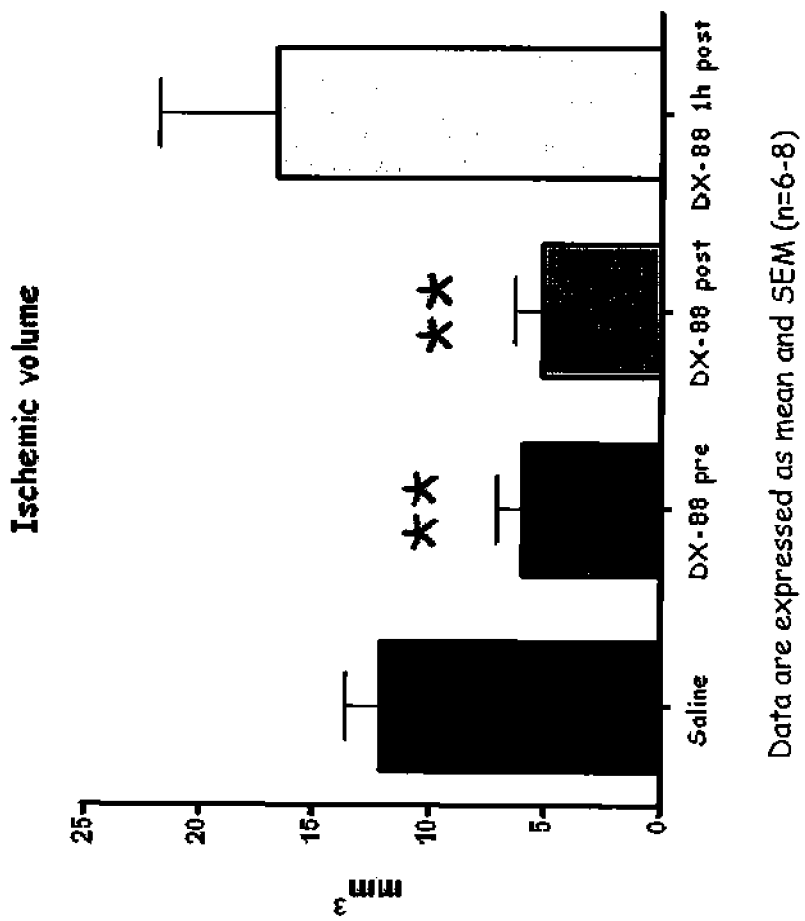
FIG. 5 is a graph depicting ischemic volume in C57B1/6 mice subjected to transient focal cerebral ischemia by middle cerebral artery occlusion (MCAO) using 6-0 microfilament and administered saline (control) or a kallikrein inhibitor polypeptide (DX-88) at various periods before and after ischemic damage. The kallikrein inhibitor polypeptide was administered at the beginning of the ischemic period (DX-88 pre), at the end of the ischemic period (DX-88 post), or at one hour after the beginning of the ischemic period (DX-88 1 h post). The kallikrein inhibitor polypeptide was administered at 30 µg.
Figure 6:
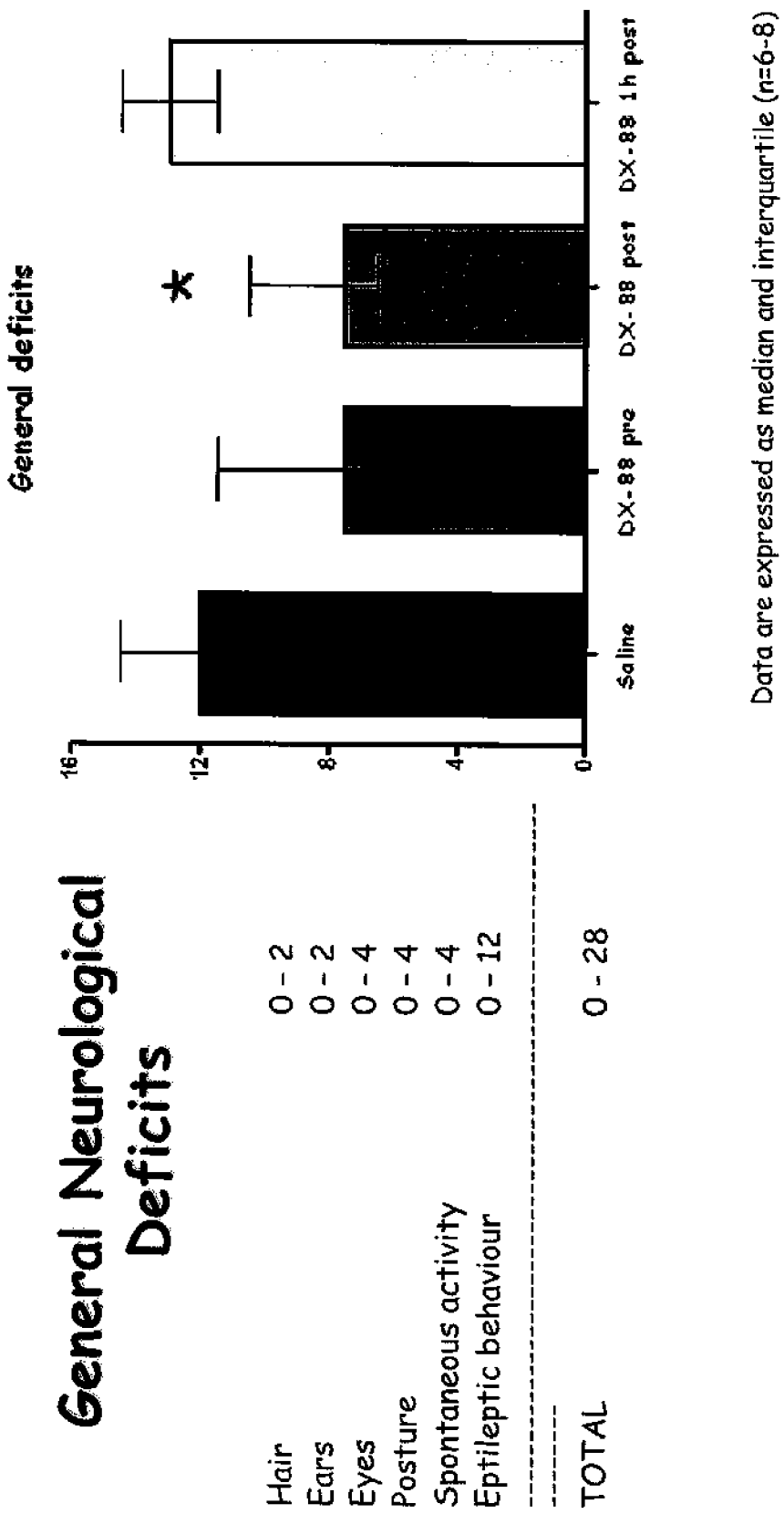
FIG. 6 is a graph depicting general neurological deficits in C57B1/6 mice subjected to transient focal cerebral ischemia by middle cerebral artery occlusion (MCAO) using 6-0 microfilament and administered saline (control) or a kallikrein inhibitor polypeptide (DX-88) at various periods before and after ischemic damage. The kallikrein inhibitor polypeptide was administered at the beginning of the ischemic period (DX-88 pre), at the end of the ischemic period (DX-88 post), or at one hour after the beginning of the ischemic period (DX-88 1 h post). The kallikrein inhibitor polypeptide was administered at 30 µg. General neurological deficits were measured based upon evaluation of the hair, ears, eyes, posture, spontaneous activity and eptileptic behavior in the mice.
Figures 7, 8:
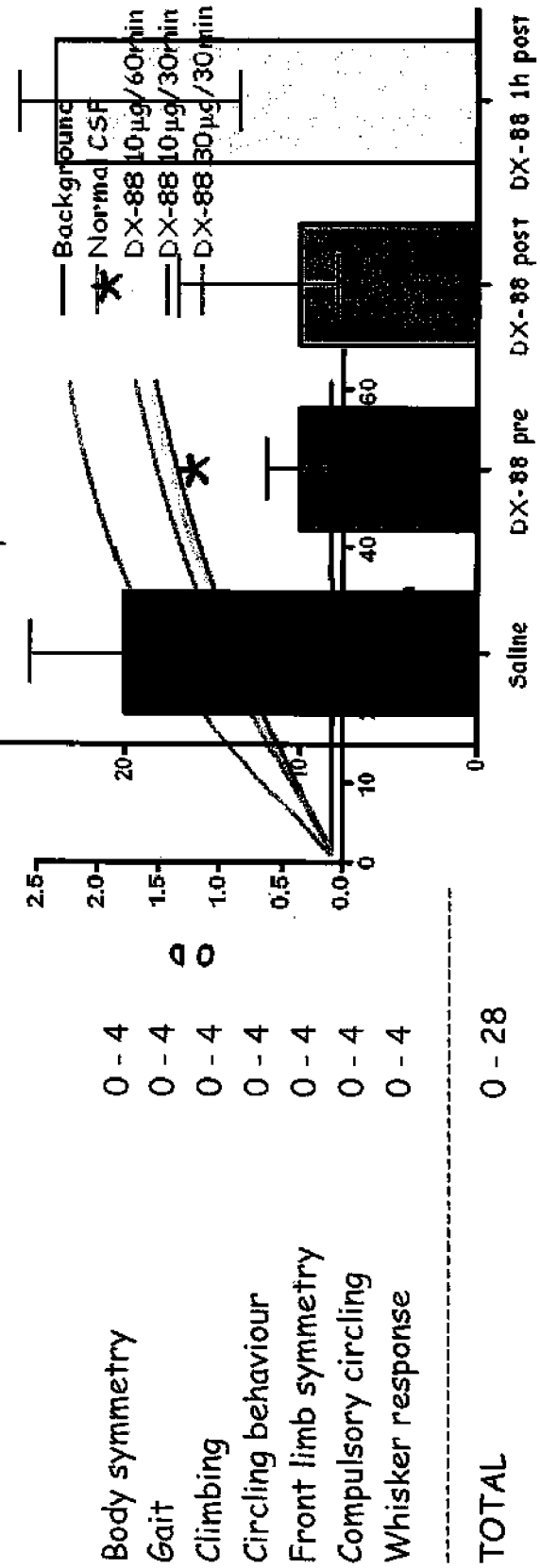
FIG. 7 is a graph depicting focal neurological deficits in C57B1/6 mice subjected to transient focal cerebral ischemia by middle cerebral artery occlusion (MCAO) using 6-0 microfilament and administered saline (control) or a kallikrein inhibitor polypeptide (DX-88) at various periods before and after ischemic damage. The kallikrein inhibitor polypeptide was administered at the beginning of the ischemic period (DX-88 pre), at the end of the ischemic period (DX-88 post), or at one hour after the beginning of the ischemic period (DX-88 1 h post). The kallikrein inhibitor polypeptide was administered at 30 µg. Focal neurological deficits were measured based upon evaluation of the body symmetry, gait, climbing ability, circling behavior, front limb symmetry, compulsory circling and whisker response in the mice.
FIG. 8 is a graph depicting the levels of a kallikrein activity found in the cerebral spinal fluid (CSF) of either untreated mice (normal CSF) or mice treated with a kallikrein inhibitor polypeptide (DX-88) at various doses (10 µg or 30 µg) measured at 30 or 60 minutes after administration.

Kallikrein inhibitors, particularly inhibitors of plasma kallikrein, can be used to prevent or treat disorders associated with blood loss or blood fluidity. For example, such inhibitors can be used to treat or prevent perioperative blood loss, a systemic inflammatory response (SIR) induced by kallikrein (especially, for example, in patients undergoing surgical procedures and particularly surgical procedures involving cardiothoracic surgery, e.g., cardiopulmonary bypass (CPB), such as a coronary artery bypass graft (CABG) procedures as well as in patients with other disorders), cerebral ischemia and/or reperfusion injury associated with ischemia, e.g., cerebral ischemia.

Further examples of applications for kallikrein inhibitors include pediatric cardiac surgery, lung transplantation, total hip replacement and orthotopic liver transplantation, and to reduce or prevent perioperative stroke during CABG, extracorporeal membrane oxygenation (ECMO) and cerebrovascular accidents (CVA) during these procedures. Kallikrein inhibitors can also be used for stroke, e.g., embolism, thrombus and/or hemorrhage associated stroke and for reperfusion injury associated with stroke.

Cardiothoracic surgery is surgery of the chest area, most commonly the heart and lungs. Typical diseases treated by cardiothoracic surgery include coronary artery disease, tumors and cancers of the lung, esophagus and chest wall, heart vessel and valve abnormalities, and birth defects involving the chest or heart. Where cardiothoracic surgery is utilized for treatment, the risk of blood loss (e.g., surgery-induced ischemia) and the onset of a systemic inflammatory response (SIR) is incurred. Surgery-induced SIR can result in severe organ dysfunction (systemic inflammatory response syndrome; SIRS).

Kunitz Domains

A number of useful inhibitors of kallikrein include a Kunitz domain.

As used herein, a "Kunitz domain" is a polypeptide domain having at least 51 amino acids and containing at least two, and preferably three, disulfides. The domain is folded such that the first and sixth cysteines, the second and fourth, and the third and fifth cysteines form disulfide bonds (e.g., in a Kunitz domain having 58 amino acids, cysteines can be present at positions corresponding to amino acids 5, 14, 30, 38, 51, and 55, according to the number of the BPTI sequence provided below, and disulfides can form between the cysteines at position 5 and 55, 14 and 38, and 30 and 51), or, if two disulfides are present, they can form between a corresponding subset of cysteines thereof. The spacing between respective cysteines can be within 7, 5, 4, 3 or 2 amino acids of the following spacing between positions corresponding to: 5 to 55, 14 to 38, and 30 to 51, according to the numbering of the BPTI sequence provided below. The BPTI sequence can be used a reference to refer to specific positions in any generic Kunitz domain. Comparison of a Kunitz domain of interest to BPTI can be performed by identifying the best fit alignment in which the number of aligned cysteines in maximized.

The 3D structure (at high resolution) of the Kunitz domain of BPTI is known. One of the X-ray structures is deposited in the Brookhaven Protein Data Bank as "6PTI". The 3D structure of some BPTI homologues (Eigenbrot et al., (1990) Protein Engineering, 3(7):591-598; Hynes et al., (1990) Biochemistry, 29:10018-10022) are known. At least seventy Kunitz domain sequences are known. Known human homologues include three Kunitz domains of LACI (Wun et al., (1988) J. Biol. Chem. 263(13):6001-6004; Girard et al., (1989) Nature, 338:518-20; Novotny et al, (1989) J. Biol. Chem., 264(31):18832-18837) two Kunitz domains of Inter-α-Trypsin Inhibitor, APP-I (Kido et al., (1988) J. Biol. Chem., 263(34):18104-18107), a Kunitz domain from collagen, and three Kunitz domains of TFPI-2 (Sprecher et al., (1994) PNAS USA, 91:3353-3357). LACI is a human serum phosphoglycoprotein with a molecular weight of 39 kDa (amino acid sequence in Table 1) containing three Kunitz domains.

TABLE 1

Exemplary Natural Kunitz Domains

```
LACI:          1  MIYTMKKVHA LWASVCLLLN LAPAPLNAds eedeehtiit dtelpplklM
(SEQ ID       51  HSFCAFKADD GPCKAIMKRF FFNIFTRQCE EFIYGGCEGN QNRFESLEEC
NO. 54)      101  KKMCTRDnan riikttlqqe kpdfCfleed pqiCrqyitr yfynnqtkqC
             151  erfkyqqClq nmnnfetlee CkniCedqpn gfqvdnygtq lnavnnsltp
             201  qstkvpslfe fhgpswCltp adrglCrane nrfyynsvig kCrpfkysgC
             251  ggnennftsk qeClraCkkg fiqriskggl iktkrkrkkq rvkiayeeif
             301  vknm
             The signal sequence (1-28) is uppercase and underscored
             LACI-K1 is uppercase
             LACI-K2 is underscored
             LACI-K3 is bold BPTI               1          2          3          4          5
(SEQ ID      1234567890123456789012345678901234557890123455789012345678
NO: 55)      RPDFCLEPPYTGPCKARIIRYFYNAKAGLCQTFVYGGCRAKRNNFKSAEDCMRTCGGA
```

The Kunitz domains above are referred to as LACI-K1 (residues 50 to 107), LACI-K2 (residues 121 to 178), and LACI-K3 (213 to 270). The cDNA sequence of LACI is reported in Wun et al. (J. Biol. Chem., 1988, 263(13):6001-6004). Girard et al. (Nature, 1989, 338:518-20) reports mutational studies in which the P1 residues of each of the three Kunitz domains were altered. LACI-K1 inhibits Factor VIIa (F.VIIa) when F.VIIa is complexed to tissue factor and LACI-K2 inhibits Factor Xa.

Proteins containing exemplary Kunitz domains include the following, with SWISS-PROT Accession Numbers in parentheses:
A4_HUMAN (P05067), A4_MACFA (P53601), A4_MACMU (P29216), A4_MOUSE (P12023), A4_RAT (P08592), A4_SAISC (Q95241), AMBP_PLEPL (P36992), APP2_HUMAN (Q06481), APP2_RAT (P15943), AXP1_ANTAF (P81547), AXP2_ANTAF (P81548), BPT1_BOVIN (P00974), BPT2_BOVIN (P04815), CA17_HUMAN (Q02388), CA36_CHICK (P15989), CA36_HUMAN (P12111), CRPT_BOOMI (P81162), ELAC_MACEU (O62845), ELAC_TRIVU (Q29143), EPPI_HUMAN (O95925), EPPI_MOUSE (Q9DA01), HTIB_MANSE (P26227), IBP_CARCR (P00993), IBPC_BOVIN (P00976), IBPI_TACTR (P16044), IBPS_BOVIN (P00975), ICS3_BOMMO (P07481), IMAP_DROFU (P11424), IP52_ANESU (P10280), ISC1_BOMMO (P10831), ISC2_BOMMO (P10832), ISH1_STOHE (P31713), ISH2_STOHE (P81129), ISIK_HELPO (P00994), ISP2_GALME (P81906), IVB1_BUNFA (P25660), IVB1_BUNMU (P00987), IVB1_VIPAA (P00991), IVB2_BUNMU (P00989), IVB2_DABRU (P00990), IVB2_HEMHA (P00985), IVB2_NAJNI (P00986), IVB3_VIPAA (P00992), IVBB_DENPO (P00983), IVBC_NAJNA (P19859), IVBC_OPHHA (P82966), IVBE_DENPO (P00984), IVBI_DENAN (P00980), IVBI_DENPO (P00979), IVBK_DENAN (P00982), IVBK_DENPO (P00981), IVBT_ERIMA (P24541), IVBT_NAJNA (P20229), MCPI_MELCP (P82968), SBPI_SARBU (P26228), SPT3_HUMAN (P49223), TKD1_BOVIN (Q28201), TKD1_SHEEP (Q29428), TXCA_DENAN (P81658), UPTI_PIG (Q29100), AMBP_BOVIN (P00978), AMBP_HUMAN (P02760), AMBP_MERUN (Q62577), AMBP_MESAU (Q60559), AMBP_MOUSE (Q07456), AMBP_PIG (P04366), AMBP_RAT (Q64240), IATR_HORSE (P04365), IATR_SHEEP (P13371), SPT1_HUMAN (O43278), SPT1_MOUSE (Q9R097), SPT2_HUMAN (O43291), SPT2_MOUSE (Q9WUO3), TFP2_HUMAN (P48307), TFP2_MOUSE (O35536), TFPI_HUMAN (P10646), TFPI_MACMU (Q28864), TFPI_MOUSE (O54819), TFPI_RABIT (P19761), TFPI_RAT (Q02445), YN81_CAEEL (Q03610)

A variety of methods can be used to identify a Kunitz domain from a sequence database. For example, a known amino acid sequence of a Kunitz domain; a consensus sequence, or a motif (e.g., the ProSite Motif) can be searched against the GenBank sequence databases (National Center for Biotechnology Information, National Institutes of Health, Bethesda Md.), e.g., using BLAST; against Pfam database of HMMs (Hidden Markov Models) (e.g., using default parameters for Pfam searching; against the SMART database; or against the ProDom database. For example, the Pfam Accession Number PF00014 of Pfam Release 9 provides numerous Kunitz domains and an HMM for identify Kunitz domains. A description of the Pfam database can be found in Sonhammer et al. (1997) *Proteins* 28(3):405-420 and a detailed description of HMMs can be found, for example, in Gribskov et al. (1990) *Meth. Enzymol.* 183:146-159; Gribskov et al. (1987) *Proc. Natl. Acad. Sci. USA* 84:4355-4358; Krogh et al. (1994) *J. Mol. Biol.* 235:1501-1531; and Stultz et al. (1993) *Protein Sci,* 2:305-314. The SMART database (Simple Modular Architecture Research Tool, EMBL, Heidelberg, Del.) of HMMs as described in Schultz et al. (1998), *Proc. Natl. Acad. Sci. USA* 95:5857 and Schultz et al. (2000) *Nucl. Acids Res* 28:231. The SMART database contains domains identified by profiling with the hidden Markov models of the HMMer2 search program (R. Durbin et al. (1998) *Biological sequence analysis: probabilistic models of proteins and nucleic acids.* Cambridge University Press). The database also is annotated and monitored. The ProDom protein domain database consists of an automatic compilation of homologous domains (Carpet et al. (1999), *Nucl. Acids Res.* 27:263-267). Current versions of ProDom are built using recursive PSI-BLAST searches (Altschul et al. (1997) *Nucleic Acids Res.* 25:3389-3402; Gouzy et al. (1999) *Computers and Chemistry* 23:333-340.) of the SWISS-PROT 38 and TREMBL protein databases. The database automatically generates a consensus sequence for each domain. Prosite lists the Kunitz domain as a motif and identifies proteins that include a Kunitz domain. See, e.g., Falquet et al. Nucleic Acids Res. 30:235-238 (2002).

Kunitz domains interact with target protease using, primarily, amino acids in two loop regions ("binding loops"). The first loop region is between about residues corresponding to amino acids 15-20 of BPTI. The second loop region is between about residues corresponding to amino acids 31-37 of BPTI. An exemplary library of Kunitz domains varies one or more amino acid positions in the first and/or second loop regions. Particularly useful positions to vary, when screening for Kunitz domains that interact with kallikrein or when selecting for improved affinity variants, include: positions 13, 16, 17, 18, 19, 31, 32, 34, and 39 with respect to the sequence of BPTI. At least some of these positions are expected to be in close contact with the target protease. It is also useful to vary other positions, e.g., positions that are adjacent to the aforementioned positions in the three-dimensional structure.

The "framework region" of a Kunitz domain is defined as those residues that are a part of the Kunitz domain, but specifically excluding residues in the first and second binding loops regions, i.e., about residues corresponding to amino acids 15-20 of BPTI and 31-37 of BPTI. Conversely, residues that are not in the binding loop may tolerate a wider range of amino acid substitution (e.g., conservative and/or non-conservative substitutions).

In one embodiment these Kunitz domains are variant forms of the looped structure including Kunitz domain 1 of human lipoprotein-associated coagulation inhibitor (LACI) protein. LACI contains three internal, well-defined, peptide loop structures that are paradigm Kunitz domains (Girard, T. et al., 1989. Nature, 338:518-520). Variants of Kunitz domain 1 of LACI described herein have been screened, isolated and bind kallikrein with enhanced affinity and specificity (see, for example, U.S. Pat. Nos. 5,795,865 and 6,057,287, incorporated herein by reference). These methods can also be applied to other Kunitz domain frameworks to obtain other Kunitz domains that interact with kallikrein, e.g., plasma kallikrein. Useful modulators of kallikrein function typically bind and/or inhibit kallikrein, as determined using kallikrein binding and inhibition assays.

An exemplary polypeptide that includes a Kunitz domain that inhibits kallikrein has the amino acid sequence defined by amino acids 3-60 of SEQ ID NO:2.

An exemplary polypeptide includes the amino acid sequence:

(SEQ ID NO: 1)
Xaa1 Xaa2 Xaa3 Xaa4 Cys Xaa6 Xaa7 Xaa8 Xaa9 Xaa10

Xaa11 Gly Xaa13 Cys Xaa15 Xaa16 Xaa17 Xaa18 Xaa19

Xaa20 Xaa21 Xaa22 Xaa23 Xaa24 Xaa25 Xaa26 Xaa27

Xaa28 Xaa29 Cys Xaa31 Xaa32 Phe Xaa34 Xaa35 Gly

Gly Cys Xaa39 Xaa40 Xaa41 Xaa42 Xaa43 Xaa44 Xaa45

Xaa46 Xaa47 Xaa48 Xaa49 Xaa50 Cys Xaa52 Xaa53

Xaa54 Cys Xaa56 Xaa57 Xaa58

"Xaa" refers to a position in a peptide chain that can be any of a number of different amino acids. In a first example, Xaa can by any amino acid except cysteine. In another example, one or more of the following apply: Xaa10 can be Asp or Glu; Xaa11 can be Asp, Gly, Ser, Val, Asn, Ile, Ala or Thr; Xaa13 can be Pro, Arg, His, Asn, Ser, Thr, Ala, Gly, Lys or Gln; Xaa15 can be Arg, Lys, Ala, Ser, Gly, Met, Asn or Gln; Xaa16 can be Ala, Gly, Ser, Asp or Asn; Xaa17 can be Ala, Asn, Ser, Ile, Gly, Val, Gln or Thr; Xaa18 can be His, Leu, Gln or Ala; Xaa19 can be Pro, Gln, Leu, Asn or Ile; Xaa21 can be Trp, Phe, Tyr, His or Ile; Xaa31 can be Glu, Asp, Gln, Asn, Ser, Ala, Val, Leu, Ile or Thr; Xaa32 can be Glu, Gln, Asp Asn, Pro, Thr, Leu, Ser, Ala, Gly or Val; Xaa34 can be Ile, Thr, Ser, Val, Ala, Asn, Gly or Leu; Xaa35 can be Tyr, Trp or Phe; Xaa39 can be Glu, Gly, Ala, Ser or Asp. Amino acids Xaa6, Xaa7, Xaa8, Xaa9, Xaa20, Xaa24, Xaa25, Xaa26, Xaa27, Xaa28, Xaa29, Xaa41, Xaa42, Xaa44, Xaa46, Xaa47, Xaa48, Xaa49, Xaa50, Xaa52, Xaa53 and Xaa54 can be any amino acid.

Additionally, each of the first four and at last three amino acids of SEQ ID NO:1 can optionally be present or absent and can be any amino acid, if present, e.g., any non-cysteine amino acid.

In one embodiment, the polypeptide has a sequence with one or more of the following properties: Xaa11 can be Asp, Gly, Ser or Val; Xaa13 can be Pro, Arg, His or Asn; Xaa15 can be Arg or Lys; Xaa16 can be Ala or Gly; Xaa17 can be Ala, Asn, Ser or Ile; Xaa18 can be His, Leu or Gln; Xaa19 can be Pro, Gln or Leu; Xaa21 can be Trp or Phe; Xaa31 is Glu; Xaa32 can be Glu or Gln; Xaa34 can be Ile, Thr or Ser; Xaa35 is Tyr; and Xaa39 can be Glu, Gly or Ala.

An exemplary polypeptide can include the following amino acids: Xaa10 is Asp; Xaa11 is Asp; Xaa13 can be Pro or Arg; Xaa15 is Arg; Xaa16 can be Ala or Gly; Xaa17 is Ala; Xaa18 is His; Xaa19 is Pro; Xaa21 is Trp; Xaa31 is Glu; Xaa32 is Glu; Xaa34 can be Ile or Ser; Xaa35 is Tyr; and Xaa39 is Gly.

It is also possible to use portions of the polypeptides described herein. For example, polypeptides could include binding domains for specific kallikrein epitopes. For example, the binding loops of Kunitz domains can by cyclized and used in isolation or can be grafted onto another domain, e.g., a framework of another Kunitz domain. It is also possible to remove one, two, three, or four amino acids from the N-terminus of an amino acid sequence described herein, and/or one, two, three, four, or five amino acids from the C-terminus of an amino acid sequence described herein.

Examples of sequences encompassed by SEQ ID NO:1 are described by the following (where not indicated, "Xaa" refers to any amino acid, any non-cysteine amino acid or any amino acid from the same set of amino acids that are allowed for SEQ ID NO:1):

(SEQ ID NO: 33)
Met His Ser Phe Cys Ala Phe Lys Ala Xaa10 Xaa11

Gly Xaa13 Cys Xaa15 Xaa16 Xaa17 Xaa18 Xaa19 Arg

Xaa21 Phe Phe Asn Ile Phe Thr Arg Gln Cys Xaa31

Xaa32 Phe Xaa34 Xaa35 Gly Gly Cys Xaa39 Gly Asn

Gln Asn Arg Phe Glu Ser Leu Glu Glu Cys Lys Lys

Met Cys Thr Arg Asp.

(amino acids 3-60 of SEQ ID NO: 2)
Met His Ser Phe Cys Ala Phe Lys Ala Asp Asp Gly Pro Cys Arg Ala Ala His Pro Arg Trp Phe Phe Asn Ile Phe Thr Arg Gln Cys Glu Glu Phe Ile Tyr Gly Gly Cys Glu Gly Asn Gln Asn Arg Phe Glu Set Leu Glu Glu Cys Lys Lys Met Cys Thr Arg Asp, (SEQ ID NO: 4)
Met His Ser Phe Cys Ala Phe Lys Ala Asp Asp Gly Pro Cys Lys Ala Asn His Leu Arg Phe Phe Asn Ile Phe Thr Arg Gln Cys Glu Glu Phe Ser Tyr Gly Gly Cys Gly Gly Asn Gln Asn Arg Phe Glu Ser Leu Gln Glu Cys Lys Lys Met Cys Thr Arg Asp, (SEQ ID NO: 5)
Met His Ser Phe Cys Ala Phe Lys Ala Asp Asp Gly His Cys Lys Ala Asn His Gln Arg Phe Phe Asn Ile Phe Thr Arg Gln Cys Glu Glu Phe Thr Tyr Gly Gly Cys Gly Gly Asn Gln Asn Arg Phe Glu Ser Leu Glu Glu Cys Lys Lys Met Cys Thr Arg Asp, (SEQ ID NO: 6)
Met His Ser Phe Cys Ala Phe Lys Ala Asp Asp Gly His Cys Lys Ala Asn His Gln Arg Phe Phe Asn Ile Phe Thr Arg Gln Cys Glu Gln Phe Thr Tyr Gly Gly Cys Ala Gly Asn Gln Asn Arg Phe Glu Ser Leu Glu Glu Cys Lys Lys Met Cys Thr Arg Asp, (SEQ ID NO: 7)
Met His Ser Phe Cys Ala Phe Lys Ala Asp Asp Gly His Cys Lys Ala Ser Len Pro Arg Phe Phe Asn Ile Phe Thr Arg Gin Cys Glu Glu Phe Ile Tyr Gly Gly Cys Gly Gly Asn Gln Asn Arg Phe Glu Ser Leu Glu Glu Cys Lys Lys Met Cys Thr Arg Asp, (SEQ ID NO: 8)
Met His Ser Phe Cys Ala Phe Lys Ala Asp Asp Gly His Cys Lys Ala Asn His Gln Arg Phe Phe Asn Ile Phe Thr Arg Gln Cys Glu Glu Phe Ser Tyr Gly

```
                                                    (SEQ ID NO: 9)
Met His Ser Phe Cys Ala Phe Lys Ala Asp Asp Gly
His Cys Lys Gly Ala His Leu Arg Phe Phe Asn
Ile Phe Thr Arg Gln Cys Glu Glu Phe Ile Tyr Gly
Gly Cys Glu Gly Asn Gln Asn Arg Phe Glu Ser Leu
Glu Glu Cys Lys Lys Met Cys Thr Arg Asp, (SEQ ID NO: 10)
Met His Ser Phe Cys Ala Phe Lys Ala Asp Asp Gly
Arg Cys Lys Gly Ala His Leu Arg Phe Phe Asn
Ile Phe Thr Arg Gln Cys Glu Glu Phe Ile Tyr Gly
Gly Cys Glu Gly Asn Gln Asn Arg Phe Gln Ser Leu
Glu Glu Cys Lys Lys Met Cys Thr Arg Asp, (SEQ ID NO: 11)
Met His Ser Phe Cys Ala Phe Lys Ala Asp Gly Gly
Arg Cys Arg Gly Ala His Pro Arg Trp Phe Phe Asn
Ile Phe Thr Arg Gln Cys Glu Glu Phe Ser Tyr Gly
Gly Cys Gly Gly Asn Gln Asn Arg Phe Glu Ser Leu
Glu Glu Cys Lys Lys Met Cys Thr Arg Asp, (SEQ ID NO: 12)
Met His Ser Phe Cys Ala Phe Lys Ala Asp Asp Gly
Pro Cys Arg Ala Ala His Pro Arg Trp Phe Phe Asn
Ile Phe Thr Arg Gln Cys Glu Glu Phe Ser Tyr Gly
Gly Cys Gly Gly Asn Gln Asn Arg Phe Glu Ser Leu
Glu Glu Cys Lys Lys Met Cys Thr Arg Asp, (SEQ ID NO: 13)
Met His Ser Phe Cys Ala Phe Lys Ala Asp Val Gly
Arg Cys Arg Gly Ala His Pro Arg Trp Phe Phe Asn
Ile Phe Thr Arg Gln Cys Glu Glu Phe Ser Tyr Gly
Gly Cys Gly Gly Asn Gln Asn Arg Phe Glu Ser Leu
Glu Glu Cys Lys Lys Met Cys Thr Arg Asp, (SEQ ID NO: 14)
Met His Ser Phe Cys Ala Phe Lys Ala Asp Val Gly
Arg Cys Arg Gly Ala Gln Pro Arg Phe Phe Phe Asn
Ile Phe Thr Arg Gln Cys Glu Glu Phe Ser Tyr Gly
Gly Cys Gly Gly Asn Gln Asn Arg Phe Glu Ser Leu
Glu Glu Cys Lys Lys Met Cys Thr Arg Asp, (SEQ ID NO: 15)
Met His Ser Phe Cys Ala Phe Lys Ala Asp Asp Gly
Ser Cys Arg Ala Ala His Leu Arg Trp Phe Phe Asn
Ile Phe Thr Arg Gln Cys Glu Glu Phe Ser Tyr Gly
Gly Cys Gly Gly Asn Gln Asn Arg Phe Glu Ser Leu
Glu Glu Cys Lys Lys Met Cys Thr Arg Asp, (SEQ ID NO: 16)
Met His Ser Phe Cys Ala Phe Lys Ala Gln Gly Gly
Ser Cys Arg Ala Ala His Gln Arg Trp Phe Phe Asn
Ile Phe Thr Arg Gln Cys Glu Gln Phe Ser Tyr Gly
Gly Cys Gly Gly Asn Gln Asn Arg Phe Glu Ser Leu
Glu Glu Cys Lys Lys Met Cys Thr Arg Asp, (SEQ ID NO: 17)
Met His Ser Phe Cys Ala Phe Lys Ala Asp Asp Gly
Pro Cys Arg Gly Ala His Leu Arg Phe Phe Phe Asn
Ile Phe Thr Arg Gln Cys Glu Glu Phe Ser Tyr Gly
Gly Cys Gly Gly Asn Gln Asn Arg Phe Glu Ser Leu
Glu Glu Cys Lys Lys Met Cys Thr Arg Asp, (SEQ ID NO: 18)
Met His Ser Phe Cys Ala Phe Lys Ala Asp Asp Gly
His Cys Arg Gly Ala Leu Pro Arg Trp Phe Phe Asn
Ile Phe Thr Arg Gln Cys Glu Glu Phe Ser Tyr Gly
Gly Cys Gly Gly Asn Gln Asn Arg Phe Glu Ser Leu
Glu Glu Cys Lys Lys Met Cys Thr Arg Asp, (SEQ ID NO: 19)
Met His Ser Phe Cys Ala Phe Lys Ala Asp Ser Gly
Asn Cys Arg Gly Asn Leu Pro Arg Phe Phe Phe Asn
Ile Phe Thr Arg Gln Cys Glu Glu Phe Ser Tyr Gly
Gly Cys Gly Gly Asn Gln Asn Arg Phe Gln Ser Leu
Glu Glu Cys Lys Lys Met Cys Thr Arg Asp, (SEQ ID NO: 20)
Met His Ser Phe Cys Ala Phe Lys Ala Asp Ser Gly
Arg Cys Arg Gly Asn His Gln Arg Phe Phe Phe Asn
Ile Phe Thr Arg Gln Cys Glu Glu Phe Ser Tyr Gly
Gly Cys Gly Gly Asn Gln Asn Arg Phe Glu Ser Leu
Glu Glu Cys Lys Lys Met Cys Thr Arg Asp, (SEQ ID NO: 21)
Met His Ser Phe Cys Ala Phe Lys Ala Asp Gly Gly
Arg Cys Arg Ala Ile Gln Pro Arg Trp Phe Phe Asn
Ile Phe Thr Arg Gln Cys Glu Glu Phe Ser Tyr Gly
Gly Cys Gly Gly Asn Gln Asn Arg Phe Glu Ser Leu
Glu Glu Cys Lys Lys Met Cys Thr Arg Asp, (SEQ ID NO: 22)
Met His Ser Phe Cys Ala Phe Lys Ala Asp Asp Gly
Arg Cys Arg Gly Ala His Pro Arg Trp Phe Phe Asn
Ile Phe Thr Arg Gln Cys Glu Glu Phe Ser Tyr Gly
Gly Cys Gly Gly Asn Gln Asn Arg Phe Glu Ser Leu
Glu Glu Cys Lys Lys Met Cys Thr Arg Asp.
```

Additional examples of sequence include those that differ by at least one amino acid, but fewer than seven, six, five, four, three, or two amino acids differences relative to an amino acid sequence described herein, e.g., an amino acid sequence provided above. In one embodiment, fewer than three, two, or one differences are in one of the binding loops. For example, the first binding loop may have no differences relative to an amino acid sequence described herein, e.g., an amino acid sequence provided above. In another example, neither the first nor the second binding loop differs from an amino acid sequence described herein, e.g., an amino acid sequence provided above.

FIGS. 3A and 3B provides an amino acid sequence alignment of these sequences, the native LACI sequence from which these variants were derived (SEQ ID NO:32), and other known Kunitz domains (SEQ ID NOS: 29-31 and 33-53). Still others polypeptides that inhibit kallikrein include an about 58-amino acid sequence of amino acids 3-60 of SEQ ID NO:2 or the PEP-1 polypeptide having the 60-amino acid sequence of SEQ ID NO:2. The term "PEP-1" and "DX-88" as used herein refer to the 60-amino acid sequence of SEQ ID NO:2. A nucleotide sequence encoding the amino acid sequence of SEQ ID NO:2 is provided in SEQ ID NO:3 (see, e.g., nucleotides 309-488 in FIG. 2). It is understood that based on the known genetic code, degenerate forms of the nucleotide sequence of SEQ ID NO:3 can be obtained by simply substituting one or more of the known degenerate codons for each amino acid encoded by the nucleotide sequence. Nucleotides 7-180 of SEQ ID NO:3, and degenerate forms thereof, encode the non-naturally occurring Kunitz domain polypeptide that includes the 58-amino acid sequence of amino acids 3-60 of SEQ ID NO:2, a related sequence, or a functional fragment thereof.

In one embodiment, the polypeptide that inhibits kallikrein is aprotinin. In another embodiment, the polypeptide is other than aprotinin, e.g., differs from aprotinin, by at least one, two, three, five, ten, or fifteen amino acids.

Polypeptides described herein can be made synthetically using any standard polypeptide synthesis protocol and equipment. For example, the stepwise synthesis of a polypeptide can be carried out by the removal of an amino (N) terminal-protecting group from an initial (i.e., carboxy-terminal) amino acid, and coupling thereto of the carboxyl end of the next amino acid in the sequence of the polypeptide. This amino acid is also suitably protected. The carboxyl group of the incoming amino acid can be activated to react with the N-terminus of the bound amino acid by formation into a reactive group such as formation into a carbodiimide, a symmetric acid anhydride, or an "active ester" group such as hydroxybenzotriazole or pentafluorophenyl esters. Preferred solid-phase peptide synthesis methods include the BOC method, which utilizes tert-butyloxycarbonyl as the α-amino protecting group, and the FMOC method, which utilizes 9-fluorenylmethloxycarbonyl to protect the α-amino of the amino acid residues. Both methods are well known to those of skill in the art (Stewart, J. and Young, J., Solid-Phase Peptide Synthesis (W.H. Freeman Co., San Francisco 1989); Merrifield, J., 1963. Am. Chem. Soc., 85:2149-2154; Bodanszky, M. and Bodanszky, A., The Practice of Peptide Synthesis (Springer-Verlag, New York 1984)). If desired, additional amino- and/or carboxy-terminal amino acids can be designed into the amino acid sequence and added during polypeptide synthesis.

Polypeptides can also be produced using recombinant technology. Recombinant methods can employ any of a number of cells and corresponding expression vectors, including but not limited to bacterial expression vectors, yeast expression vectors, baculovirus expression vectors, mammalian viral expression vectors, and the like. A polypeptide described herein can be produced by a transgenic animal, e.g., in the mammary gland of a transgenic animal. In some cases, it could be necessary or advantageous to fuse the coding sequence for a polypeptide that inhibits kallikrein (e.g., a polypeptide that includes a Kunitz domain) to another coding sequence in an expression vector to form a fusion polypeptide that is readily expressed in a host cell. Part or all of the additional sequence can be removed, e.g., by protease digestion.

An exemplary recombinant expression system for producing a polypeptide that inhibits kallikrein (e.g., a polypeptide that includes a Kunitz domain) is a yeast expression vector, which permits a nucleic acid sequence encoding the amino acid sequence for the inhibitor polypeptide to be linked in the same reading frame with a nucleotide sequence encoding the MATα prepro leader peptide sequence of Saccharomyces cerevisiae, which in turn is under the control of an operable yeast promoter. The resulting recombinant yeast expression plasmid can be transformed by standard methods into the cells of an appropriate, compatible yeast host, which cells are able to express the recombinant protein from the recombinant yeast expression vector. Preferably, a host yeast cell transformed with such a recombinant expression vector is also able to process the fusion protein to provide an active inhibitor polypeptide. An other exemplary yeast host for producing recombinant polypeptides is Pichia pastoris.

As noted above, polypeptides that inhibit kallikrein can include a Kunitz domain polypeptide described herein. Some polypeptides can include an additional flanking sequence, preferably of one to six amino acids in length, at the amino and/or carboxy-terminal end, provided such additional amino acids do not significantly diminish kallikrein binding affinity or kallikrein inhibition activity so as to preclude use in the methods and compositions described herein. Such additional amino acids can be deliberately added to express a polypeptide in a particular recombinant host cell or can be added to provide an additional function, e.g., to provide a linker to another molecule or to provide an affinity moiety that facilitates purification of the polypeptide. Preferably, the additional amino acid(s) do not include cysteine, which could interfere with the disulfide bonds of the Kunitz domain.

An exemplary Kunitz domain polypeptide includes the amino acid sequence of residues 3-60 of SEQ ID NO:2. When expressed and processed in a yeast fusion protein expression system (e.g., based on the integrating expression plasmid pHIL-D2), such a Kunitz domain polypeptide retains an additional amino terminal Glu-Ala dipeptide from the fusion with the MATalpha-prepro leader peptide sequence of S. cerevisiae. When secreted from the yeast host cell, most of the leader peptide is processed from the fusion protein to yield a functional polypeptide (referred to herein as "PEP-1") having the amino acid sequence of SEQ ID NO:2 (see boxed region in FIG. 2).

In one embodiment, an inhibitor of kallikrein, e.g., a polypeptide inhibitor, has a binding affinity for kallikrein that is on the order of 1000 times higher than that of aprotinin, which is currently approved for use in CABG procedures to reduce blood loss. The surprisingly high binding affinities of such kallikrein inhibitors combined with their high degree of specificity for kallikrein to the exclusion of other molecular targets (see Table 1, below) provide for particularly useful inhibitors. However, inhibitors with lesser affinity or specificity also have their applications.

A typical Kunitz domain, e.g., that includes, SEQ ID NO:1, contains a number of invariant positions, e.g., positions corresponding to position 5, 14, 30, 51 and 55 in the BPTI numbering scheme are cysteine. The spacing between these positions may vary to the extent allowable within the Kunitz domain fold, e.g., such that three disulfide bonds are formed.

Other positions such as, for example, positions 6, 7, 8, 9, 20, 24, 25, 26, 27, 28, 29, 41, 42, 44, 46, 47, 48, 49, 50, 52, 53 and 54, or positions corresponding to those positions, can be any amino acid (including non-naturally occurring amino acids). In a particularly preferred embodiment, one or more amino acids correspond to that of a native sequence (e.g., SEQ ID NO:32, see FIG. 3). In another embodiment, at least one variable position is different from that of the native sequence. In yet another preferred embodiment, the amino acids can each be individually or collectively substituted by a conservative or non-conservative amino acid substitution.

Conservative amino acid substitutions replace an amino acid with another amino acid of similar chemical structure and may have no affect on protein function. Non-conservative amino acid substitutions replace an amino acid with another amino acid of dissimilar chemical structure. Examples of conserved amino acid substitutions include, for example, Asn→Asp, Arg→Lys and Ser→Thr. In a preferred embodiment, 1, 2, 3, 4, 5, 6, 7, 8, 9, 10, 11, 12, 13, 14, 15, 16, 17, 18, 19, 20 and/or 21 of these amino acids can be independently or collectively, in any combination, selected to correspond to the corresponding position of SEQ ID NO:2.

Other positions, for example, positions 10, 11, 13, 15, 16, 17, 18, 19, 21, 22, 23, 31, 32, 34, 35, 39, 40, 43 and 45, or positions corresponding to those positions can be any of a selected set of amino acids. For example, SEQ ID NO:1 defines a set of possible sequences. Each member of this set contains, for example, a cysteine at positions 5, 14, 30, 51 and 55, and any one of a specific set of amino acids at positions 10, 11, 13, 15, 16, 17, 18, 19, 221, 22, 23, 31, 32, 34, 35, 39, 40, 43 and 45, or positions corresponding to those positions. In a preferred embodiment, 1, 2, 3, 4, 5, 6, 7, 8, 9, 10, 11, 12, 13, 14, 15, 16, 17, 18 and/or 19 of these amino acids can be independently or collectively, in any combination, selected to correspond to the corresponding position of SEQ ID NO:2. The polypeptide preferably has at least 80%, 85%, 90%, 95, 97, 98, or 99% identity to SEQ ID NO:2.

As used herein, the term "substantially identical" (or "substantially homologous") is used herein to refer to a first amino acid or nucleotide sequence that contains a sufficient number of identical or equivalent (e.g., with a similar side chain, e.g., conserved amino acid substitutions) amino acid residues or nucleotides to a second amino acid or nucleotide sequence such that the first and second amino acid or nucleotide sequences have similar activities. In the case of antibodies, the second antibody has the same specificity and has at least 50% of the affinity of the same.

Calculations of "homology" between two sequences can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent homology between two sequences can be accomplished using a mathematical algorithm. In a preferred embodiment, the percent homology between two amino acid sequences is determined using the Needleman and Wunsch (1970), J. Mol. Biol. 48:444-453, algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent homology between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a homology limitation) are a Blossum 62 scoring matrix with a gap penalty of 12, a gap extend penalty of 4, and a frameshift gap penalty of 5.

Useful polypeptides can also be encoded by a nucleic acid that hybridizes to a nucleic acid that encodes a polypeptide described herein. The nucleic acids can hybridize under medium, high, or very high stringency conditions. As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: (1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions in 6×SSC at about 45° C., followed by one or more washes in 0.2×SSC, 0.1% SDS at 60° C.; (3) high stringency hybridization conditions in 6×SSC at about 45° C., followed by one or more washes in 0.2×SSC, 0.1% SDS at 65° C.; and (4) very high stringency hybridization conditions are 0.5M sodium phosphate, 7% SDS at 65° C., followed by one or more washes at 0.2×SSC, 1% SDS at 65° C.

Kallikrein Inhibitors—Antibodies

One class of kallikrein inhibitors includes antibodies. Exemplary antibodies bind, e.g., specifically to kallikrein, e.g., plasma kallikrein. An antibody can inhibit kallikrein in a number of ways. For example, it can contact one or more residues of the active site, sterically hinder or obstruct access to the active site, prevent maturation of kallikrein, or destabilize a conformation required for catalytic activity.

As used herein, the term "antibody" refers to a protein that includes at least one immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab fragments, F(ab')$_2$, a Fd fragment, a Fv fragments, and dAb fragments) as well as complete antibodies.

The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) J. Mol. Biol. 196:901-917). Kabat definitions are used herein. Each VH and VL is typically composed of three CDR's and four FR's, arranged from amino-terminus to carboxy-terminus in the following order: FR1, CDR1, FR2, CDR2, FR3, CDR3, FR4.

An "immunoglobulin domain" refers to a domain from the variable or constant domain of immunoglobulin molecules. Immunoglobulin domains typically contain two β-sheets formed of about seven β-strands, and a conserved disulphide bond (see, e.g., A. F. Williams and A. N. Barclay 1988 *Ann. Rev Immunol.* 6:381-405).

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may omit one, two or more N- or C-terminal amino acids, internal amino acids, may include one or more insertions or additional terminal amino acids, or may include other alterations. In one embodiment, a polypeptide that includes immunoglobulin variable domain sequence can associate with another immunoglobulin variable domain sequence to form a target binding structure (or "antigen binding site"), e.g., a structure that preferentially interacts with an activated integrin structure or a mimic of an activated integrin structure, e.g., relative to an non-activated structure.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region includes three domains, CH1, CH2 and CH3. The light chain constant region includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system. The term "antibody" includes intact immunoglobulins of types IgA, IgG, IgE, IgD, IgM (as well as subtypes thereof). The light chains of the immunoglobulin may be of types kappa or lambda. In one embodiment, the antibody is glycosylated. An antibody can be functional or non functional for antibody-dependent cytotoxicity and/or complement-mediated cytotoxicity.

One or more regions of an antibody can be human or effectively human. For example, one or more of the variable regions can be human or effectively human. For example, one or more of the CDRs can be human, e.g., HC CDR1, HC CDR2, HC CDR3, LC CDR1, LC CDR2, and LC CDR3. Each of the light chain CDRs can be human. HC CDR3 can be human. One or more of the framework regions can be human, e.g., FR1, FR2, FR3, and FR4 of the HC or LC. In one embodiment, all the framework regions are human, e.g., derived from a human somatic cell, e.g., a hematopoietic cell that produces immunoglobulins or a non-hematopoietic cell.

In one embodiment, the human sequences are germline sequences, e.g., encoded by a germline nucleic acid. One or more of the constant regions can be human or effectively human. In another embodiment, at least 70, 75, 80, 85, 90, 92, 95, or 98% of, or the entire antibody can be human or effectively human. An "effectively human" immunoglobulin variable region is an immunoglobulin variable region that includes a sufficient number of human framework amino acid positions such that the immunoglobulin variable region does not elicit an immunogenic response in a normal human. An "effectively human" antibody is an antibody that includes a sufficient number of human amino acid positions such that the antibody does not elicit an immunogenic response in a normal human.

All or part of an antibody can be encoded by an immunoglobulin gene or a segment thereof. Exemplary human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 Kd or 214 amino acids) are encoded by a variable region gene at the NH2-terminus (about 110 amino acids) and a kappa or lambda constant region gene at the COOH—terminus. Full-length immunoglobulin "heavy chains" (about 50 Kd or 446 amino acids), are similarly encoded by a variable region gene (about 116 amino acids) and one of the other aforementioned constant region genes, e.g., gamma (encoding about 330 amino acids).

One exemplary method for identifying antibodies that bind to and inhibit kallikrein includes immunizing a non-human animal with kallikrein or a fragment thereof. Even small peptides can be used as immunogens. In one embodiment, a mutated kallikrein which has reduced or no catalytic activity is used as immunogen. Spleen cells can be isolated from the immunized animal and used to produce hybridoma cells using standard methods. In one embodiment, the non-human animal includes one or more human immunoglobulin genes.

Another exemplary method for identifying proteins that bind to and inhibit kallikrein includes: providing a library of proteins and selecting from the library one or more proteins that bind to a kallikrein or a fragment thereof. The selection can be performed in a number of ways. For example, the library can be provided in the format of a display library or a protein array. Prior to selecting, the library can be pre-screened (e.g., depleted) to remove members that interact with a non-target molecule, e.g., protease other than a kallikrein or a kallikrein in which the active site is inaccessible, e.g., bound by an inhibitor, e.g., aprotinin.

Antibody libraries, e.g., antibody display libraries, can be constructed by a number of processes (see, e.g., de Haard et al., (1999) *J. Biol. Chem* 274:18218-30; Hoogenboom et al. (1998) *Immunotechnology* 4:1-20. and Hoogenboom et al. (2000) *Immunol Today* 21:371-8). Further, elements of each process can be combined with those of other processes. The processes can be used such that variation is introduced into a single immunoglobulin domain (e.g., VH or VL) or into multiple immunoglobulin domains (e.g., VH and VL). The variation can be introduced into an immunoglobulin variable domain, e.g., in the region of one or more of CDR1, CDR2, CDR3, FR1, FR2, FR3, and FR4, referring to such regions of either and both of heavy and light chain variable domains. In one embodiment, variation is introduced into all three CDRs of a given variable domain. In another preferred embodiment, the variation is introduced into CDR1 and CDR2, e.g., of a heavy chain variable domain. Any combination is feasible.

In an exemplary system for recombinant expression of an antibody (e.g., a full length antibody or an antigen-binding portion thereof), a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells, and recover the antibody from the culture medium. For example, some antibodies can be isolated by affinity chromatography with a Protein A or Protein G. Antibodies can also be produced by a transgenic animal.

Kallikrein Inhibitors—Peptides

The binding ligand can include a peptide of 32 amino acids or less that independently binds to a target molecule. Some such peptides can include one or more disulfide bonds. Other peptides, so-called "linear peptides," are devoid of cysteines. In one embodiment, the peptides are artificial, i.e., not present in a Nature or not present in a protein encoded by one or more genomes of interest, e.g., the human genome. Synthetic peptides may have little or no structure in solution (e.g., unstructured), heterogeneous structures (e.g., alternative conformations or "loosely structured), or a singular native structure (e.g., cooperatively folded). Some synthetic peptides adopt a particular structure when bound to a target molecule. Some exemplary synthetic peptides are so-called "cyclic peptides" that have at least a disulfide bond and, for example, a loop of about 4 to 12 non-cysteine residues. Exemplary peptides are less than 28, 24, 20, or 18 amino acids in length.

Peptide sequences that independently bind kallkrein can be identified by any of a variety of methods. For example, they can be selected from a display library or an array of peptides. After identification, such peptides can be produced synthetically or by recombinant means. The sequences can be incorporated (e.g., inserted, appended, or attached) into longer sequences.

The following are some exemplary phage libraries that can be screened to find at least some of the peptide ligands described herein. Each library displays a short, variegated exogenous peptide on the surface of M13 phage. The peptide display of five of the libraries was based on a parental domain having a segment of 4, 5, 6, 7, 8, 10, 11, or 12 amino acids, respectively, flanked by cysteine residues. The pairs of cysteines are believed to form stable disulfide bonds, yielding a cyclic display peptide. The cyclic peptides are displayed at the amino terminus of protein III on the surface of the phage. The libraries were designated TN6/7, TN7/4, TN8/9, TN9/4, TN10/10. TN11/1, and TN12/1. A phage library with a 20-amino acid linear display was also screened; this library was designated Lin20.

The TN6/7 library was constructed to display a single cyclic peptide contained in a 12-amino acid variegated template. The TN6/6 library utilized a template sequence of $Xaa_1$-$Xaa_2$-$Xaa_3$-$Cys_4$-$Xaa_5$-$Xaa_6$-$Xaa_7$-$Xaa_8$-$Cys_9$-$Xaa_{10}$-$Xaa_{11}$-$Xaa_{12}$, where each variable amino acid position in the amino acid sequence of the template is indicated by a subscript integer. Each variable amino acid position (Xaa) in the template was varied to contain any of the common α-amino acids, except cysteine (Cys).

The TN7/4 library was constructed to display a single cyclic peptide contained in a 12-amino acid variegated template. The TN7/4 library utilized a template sequence of $Xaa_1$-$Xaa_2$-$Xaa_3$-$Cys_4$-$Xaa_8$-$Xaa_6$-$Xaa_7$-$Xaa_8$-$Xaa_9$-$Cys_{10}$-$Xaa_{11}$-$Xaa_{12}$-$Xaa_{13}$, where each variable amino acid position in the amino acid sequence of the template is indicated by a subscript integer. Each variable amino acid position (Xaa) in the template was varied to contain any of the common α-amino acids, except cysteine (Cys).

The TN8/9 library was constructed to display a single binding loop contained in a 14-amino acid template. The TN8/9 library utilized a template sequence of $Xaa_2$-$Xaa_2$-$Xaa_3$-$Cys_4$-$Xaa_5$-$Xaa_6$-$Xaa_7$-$Xaa_8$-$Xaa_9$-$Xaa_{10}$-$Cys$-$Xaa_{12}$-$Xaa_{13}$-$Xaa_{14}$. Each variable amino acid position (Xaa) in the template were varied to permit any amino acid except cysteine (Cys).

The TN9/4 library was constructed to display a single binding loop contained in a 15-amino acid template. The TN9/4 library utilized a template sequence $Xaa_1$-$Xaa_2$-$Xaa_3$-$Cys_4$-$Xaa_5$-$Xaa_6$-$Xaa_7$-$Xaa_8$-$Xaa_9$-$Xaa_{10}$-$Xaa_{11}$-$Cys_{12}$-$Xaa_{13}$-$Xaa_{14}$-$Xaa_{15}$. Each variable amino acid position (Xaa) in the template were varied to permit any amino acid except cysteine (Cys).

The TN10/10 library was constructed to display a single cyclic peptide contained in a 16-amino acid variegated template. The TN10/9 library utilized a template sequence $Xaa_1$-$Xaa_2$-$Xaa_3$-$Cys_4$-$Xaa_5$-$Xaa_6$-$Xaa_7$-$Xaa_8$-$Xaa_9$-$Xaa_{10}$-$Xaa_{11}$-$Xaa_{12}$-$Cys_{13}$-$Xaa_{14}$-$Xaa_{15}$-$Xaa_{16}$, where each variable amino acid position in the amino acid sequence of the template is indicated by a subscript integer. Each variable amino acid position (Xaa) was to permit any amino acid except cysteine (Cys).

The TN11/1 library was constructed to display a single cyclic peptide contained in a 17-amino acid variegated template. The TN11/1 library utilized a template sequence $Xaa_1$-$Xaa_2$-$Xaa_3$-$Cys_4$-$Xaa_5$-$Xaa_6$-$Xaa_7$-$Xaa_8$-$Xaa_9$-$Xaa_{10}$-$Xaa_{11}$-$Xaa_{12}$-$Xaa_{13}$-$Cys_{14}$-$Xaa_{15}$-$Xaa_{16}$-$Xaa_{17}$, where each variable amino acid position in the amino acid sequence of the template is indicated by a subscript integer. Each variable amino acid position (Xaa) was to permit any amino acid except cysteine (Cys).

The TN12/1 library was constructed to display a single cyclic peptide contained in an 18-amino acid template. The TN12/1 library utilized a template sequence $Xaa_1$-$Xaa_2$-$Xaa_3$-$Cys_4$-$Xaa_5$-$Xaa_6$-$Xaa_7$-$Xaa_8$-$Xaa_9$-$Xaa_{10}$-$Xaa_{11}$-$Xaa_{12}$-$Xaa_{13}$-$Xaa_{14}$-$Cys_{15}$-$Xaa_{16}$-$Xaa_{17}$-$Xaa_{18}$, where each variable amino acid position in the amino acid sequence of the template is indicated by a subscript integer. The amino acid positions $Xaa_1$, $Xaa_2$, $Xaa_{17}$ and $Xaa_{18}$ of the template were varied, independently, to permit each amino acid selected from the group of 12 amino acids consisting of Ala, Asp, Phe, Gly, His, Leu, Asn, Pro, Arg, Ser, Trp, and Tyr. The amino acid positions $Xaa_3$, $Xaa_5$, $Xaa_6$, $Xaa_7$, $Xaa_8$, $Xaa_9$, $Xaa_{10}$, $Xaa_{11}$, $Xaa_{12}$, $Xaa_{13}$, $Xaa_{14}$, $Xaa_{16}$, of the template were varied, independently, to permit any amino acid except cysteine (Cys).

The Lin20 library was constructed to display a single linear peptide in a 20-amino acid template. The amino acids at each position in the template were varied to permit any amino acid except cysteine (Cys).

The techniques discussed in Kay et al., *Phage Display of Peptides and Proteins: A Laboratory Manual* (Academic Press, Inc., San Diego 1996) and U.S. Pat. No. 5,223,409 are useful for preparing a library of potential binders corresponding to the selected parental template. The libraries described above can be prepared according to such techniques, and screened, e.g., as described above, for peptides that bind to and inhibit kallikrein.

In addition phage libraries or selected populations from phage libraries can be counter-selected, e.g., using kallikrein that is inactivated, e.g., by binding of aprotinin or another kallikrein inhibitor. Such procedures can be used to discard peptides that do not contact the active site.

Peptides can also be synthesized using alternative backbones, e.g., a peptoid backbone, e.g., to produce a compound which has increased protease resistance. In particular this method can be used to make a compound that binds to and inhibits kallikrein and which is not itself effectively cleaved by kallikrein.

Modifications

It is possible to modify polypeptides that inhibit a Kunitz domain in a variety of ways. For example, the polypeptides can be attached to one or more polyethylene glycol moieties to stabilize the compound or prolong retention times, e.g., by at least two, four, five, or eight fold.

A polypeptide that inhibits kallikrein can be associated with (e.g., conjugated to) a polymer, e.g., a substantially non-antigenic polymers, such as polyalkylene oxides or polyethylene oxides. Suitable polymers will vary substantially by weight. Polymers having molecular number average weights ranging from about 200 to about 35,000 (or about 1,000 to about 15,000, and 2,000 to about 12,500) can be used. A plurality of polymer moieties can be attached to one polypeptide, e.g., at least two, three, or four such moieties, e.g., having an average molecular weight of about 2,000 to 7,000 Daltons.

For example, the polypeptide can be conjugated to a water soluble polymer, e.g., hydrophilic polyvinyl polymers, e.g. polyvinylalcohol and polyvinylpyrrolidone. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene (Pluronics); polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturonic acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextrane sulfate, dextran, dextrins, glycogen, or the polysaccharide subunit of acid mucopolysaccharides, e.g. hyaluronic acid; polymers of sugar alcohols such as polysorbitol and polymannitol; heparin or heparon.

Other compounds can also be attached to the same polymer, e.g., a cytotoxin, a label, or another targeting agent or an unrelated agent. Mono-activated, alkoxy-terminated polyalkylene oxides (PAO's), e.g., monomethoxy-terminated polyethylene glycols (mPEG's); $C_{1-4}$ alkyl-terminated polymers; and bis-activated polyethylene oxides (glycols) can be used for crosslinking. See, e.g., U.S. Pat. No. 5,951,974
Kallikrein Inhibitors—Small Molecules An inhibitor of a kallikrein, e.g., plasma kallikrein, can also be a compound that is smaller than 3000, 2000 or 1000 Daltons. For example, the compound is a non-proteinaceous compound or a compound that includes fewer than five peptide bonds.

For example, the inhibitor can be a compound described in WO 04/062657, e.g., an acylated 4-amidino- or 4-guanidinobenzylamine. The compound can have the general formula (I) P4-P3-P2-P1 (I), where P4 is a mono- or poly-substituted or unsubstituted benzylsulphonyl group, P3 is a mono- or poly-substituted or unsubstituted, natural or unnatural alpha-amino or alpha-imino acid with the D-configuration, P2 is a mono- or poly-substituted or unsubstituted natural or unnatural alpha-amino or alpha-imino acid with the L-configuration and P1 is a mono- or poly-substituted or unsubstituted 4-amidino- or 4-guanidinobenzylamine group.

Another example is a compound represented by Structural Formula (I):

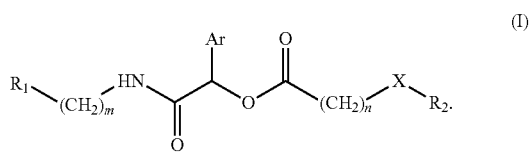

R1 is a substituted or unsubstituted aryl group or alkyl group; R2 is a substituted or unsubstituted aryl group or cycloalkyl group; Ar is a substituted or unsubstituted aryl group; X is a —CH2-, —O—, —S— or —CO—; m is an integer from zero to two; n is an integer from 0-2 when X is —O—, —S— and 1-2 when X is —CH2- or —CO—. Exemplary compounds are described in US 2004-044075.
Methods and Compositions The inhibitors described herein can be used in methods for preventing or reducing ischemia and/or reperfusion injury associated with ischemia; methods for preventing or reducing perioperative blood loss and/or a systemic inflammatory response (SIR) in a patient, especially associated with cardiothoracic surgery. The method includes administering a inhibitor of kallikrein, e.g., plasma kallikrein.

In one embodiment, a method for treatment involves the administration of a polypeptide comprising a Kunitz domain. One embodiment of the method involves using a polypeptide containing an amino acid sequence of SEQ ID NO:1 that has an affinity for kallikrein that is approximately 1000-fold or more higher than that of a broad range serine protease, e.g., aprotinin, which is isolated from bovine lung and currently approved for use in CABG procedures (TRASYLOL™, Bayer Corporation Pharmaceutical Division, West Haven, Conn.).

Patients subjected to any of a number of surgical procedures, especially those involving extra-corporeal circulation, e.g., cardiothoracic surgery, such as, for example, CPB, and/or bone trauma, such as sternal split or hip replacement, are at risk for perioperative blood loss and inflammation. Contact of a patient's blood with the cut surfaces of bone or of CPB equipment is sufficient to activate one or several undesirable cascade responses, including a contact activation system (CAS), which can lead to extensive perioperative blood loss requiring immediate blood transfusion, as well as a systemic inflammatory response (SIR), which, in turn, can result in permanent damage to tissues and organs. While not desiring to be limited to any particular mechanism or theory, it appears that the blood loss that occurs associated with cardiothoracic surgery, e.g., CPB, as in a CABG procedure, probably results from extensive capillary leakage, which can result in significant loss of blood that must be replaced by immediate blood transfusion.

The inhibitors described herein can be used to prevent or reduce various ischemias including, for example, perioperative blood loss and SIR in a patient subjected to a surgical procedure, and especially wherein the surgical procedure requires extra-corporeal circulation, e.g., cardiothoracic surgery, such as, for example, CPB. The inhibitors can be particularly useful for preventing or reducing perioperative blood loss and/or SIR in a patient subjected to a CABG procedure requiring CPB or other cardiac surgery. Further, the inhibitors described herein can be used to prevent or reduce cerebral ischemia (such as stroke) and/or reperfusion injury associated with cerebral ischemia (e.g., stroke).

Exemplary compositions for medical use comprise a kallikrein inhibitor described herein. Such compositions can further include one or more pharmaceutically acceptable buffers, carriers, and excipients, which can provide a desirable feature to the composition including, but not limited to, enhanced administration of the composition to a patient, enhanced circulating half-life of the inhibitor, enhanced compatibility of the inhibitor with patient blood chemistry, enhanced storage of the composition, and/or enhanced delivery and/or efficacy of the inhibitor upon administration to a patient. In addition to an inhibitor described herein, compositions can further include one or more other pharmaceutically active compounds that provide an additional prophylactic or therapeutic benefit to a patient, e.g., a patient of an invasive surgical procedure or a patent otherwise at risk for, having or previously had cerebral ischemia and/or reperfusion injury associated with cerebral ischemia. For example, the compositions can include another compound described herein.

Perioperative Blood Loss and Reduced Heart Bloodflow

Due to the many advances in medicine, a number of highly invasive surgical procedures are carried out each day that result in blood loss, or place patients at a high risk for blood loss. Such patients are generally carefully monitored to restore and maintain normal blood supply and hemostasis, and they may need blood transfusions. Surgical procedures that involve blood loss include those involving extra-corporeal circulation methods such as cardiothoracic surgery, e.g., CPB. In such methods, a patient's heart is stopped and the circulation, oxygenation, and maintenance of blood volume are carried out artificially using an extra-corporeal circuit and a synthetic membrane oxygenator. These techniques are commonly used during cardiac surgery. Additionally, it is apparent that surgery involving extensive trauma to bone, such as the sternal split necessary in CABG or hip replacement procedures, is also associated with activation of the CAS, which can result in a variety of disruptions in the blood and vasculature.

Atherosclerotic coronary artery disease (CAD) causes a narrowing of the lumen of one or several of the coronary arteries; this limits the flow of blood to the myocardium (i.e., the heart muscle) and can cause angina, heart failure, and myocardial infarcts. In the end stage of coronary artery atherosclerosis, the coronary circulation can be almost completely occluded, causing life threatening angina or heart failure, with a very high mortality. CABG procedures may be required to bridge the occluded blood vessel and restore blood to the heart; these are potentially life saving. CABG procedures are among the most invasive of surgeries in which one or more healthy veins or arteries are implanted to provide a "bypass" around the occluded area of the diseased vessel. CABG procedures carry with them a small but important perioperative risk, but they are very successful in providing patients with immediate relief from the mortality and morbidity of atherosclerotic cardiovascular disease. Despite these very encouraging results, repeat CABG procedures are frequently necessary, as indicated by an increase in the number of patients who eventually undergo second and even third procedures; the perioperative mortality and morbidity seen in primary CABG procedures is increased in these re-do procedures.

There have been improvements in minimally invasive surgical techniques for uncomplicated CAD. However, nearly all CABG procedures performed for valvular and/or congenital heart disease, heart transplantation, and major aortic procedures, are still carried out on patients supported by CPB. In CPB, large cannulae are inserted into the great vessels of a patient to permit mechanical pumping and oxygenation of the blood using a membrane oxygenator. The blood is returned to the patient without flowing through the lungs, which are hypoperfused during this procedure. The heart is stopped using a cardioplegic solution, the patient cooled to help prevent brain damage, and the peripheral circulating volume increased by an extracorporeal circuit, i.e., the CPB circuit, which requires "priming" with donor blood and saline mixtures are used to fill the extracorporeal circuit. CPB has been extensively used in a variety of procedures performed for nearly half a century with successful outcomes. The interaction between artificial surfaces, blood cells, blood proteins, damaged vascular endothelium, and extravascular tissues, such as bone, disturbs hemostasis and frequently activates the CAS, which, as noted above, can result in a variety of disruptions in the blood and vasculature. Such disruption leads to excess perioperative bleeding, which then requires immediate blood transfusion. A consequence of circulating whole blood through an extracorporeal circuit in CPB can also include the systemic inflammatory response (SIR), which is initiated by contact activation of the coagulation and complement systems. Indeed, much of the morbidity and mortality associated with seemingly mechanically successful CPB surgical procedures is the result of the effects of activating coagulation, fibrinolysis, or complement systems. Such activation can damage the pulmonary system, leading to adult respiratory distress syndrome (ARDS), impairment of kidney and splanchnic circulation, and induction of a general coagulopathy leading to blood loss and the need for transfusions. In addition to the dangers of perioperative blood loss, additional pathologies associated with SIR include neurocognitive deficits, stroke, renal failure, acute myocardial infarct, and cardiac tissue damage.

Blood transfusions also present a significant risk of infection and elevate the cost of CABG or other similar procedures that require CPB. In the absence of any pharmacological intervention, three to seven units of blood must typically be expended on a patient, even with excellent surgical techniques. Accordingly, there is considerable incentive for the development of new and improved pharmacologically effective compounds to reduce or prevent perioperative bleeding and SIR in patients subjected to CPB and CABG procedures. Use of the inhibitors described herein can improve these various treatments and lead to amelioration of the undesirable symptoms that can occur.

Cerebral Ischemia and Reperfusion Injury

The methods described herein are useful for reducing or preventing cerebral ischemia as well as reperfusion injury associated with cerebral ischemia. A "cerebral ischemic attack" or "cerebral ischemia" is an ischemic condition in which blood supply to the brain is blocked. This interruption in the blood supply to the brain may result from a variety of causes including, but not limited to, an intrinsic blockage or occlusion of the blood vessel itself, a remotely originated source of occlusion, decreased perfusion pressure or increased blood viscosity resulting in decreased cerebral blood flow, or ruptured or leaky blood vessels in the subarachnoid space or intracerebral tissue. Cerebral ischemia may result in either transient or permanent deficits and the seriousness of the neurological damage in a patient who has experienced cerebral ischemia depends on the intensity and duration of the ischemia event. A transient ischemia attack (TIA) is one in which the blood flow to the brain is briefly interrupted and causes temporary neurological deficits. Symptoms of TIA include numbness of weakness of face or limbs, loss of ability to speak clearly and/or understand the speech of others, a loss of vision or dimness of vision and dizziness. Permanent cerebral ischemia attacks, also called strokes, are caused by a longer interruption in blood flow to the brain resulting from an embolism, a thrombus or bleeding in the brain (e.g., a hemorrhage). The term "thromboembolic stroke" or "thromboembolism" is used herein to refer to a stroke caused by either a thrombosis or an embolism. A stroke causes a loss of neurons typically resulting in a neurological deficit that may improve but does not entirely resolve. The inhibitors described herein are useful in preventing or reducing stroke including embolic-, thrombolic-, thromboembolic- and hemorrhage-associated strokes. Strokes can be caused by a variety of causes. One category includes perioperative strokes that can be associated with thrombus or embolism formation.

In stroke patients, there is a core of the neurological deficit marked by total ischemia and/or tissue necrosis. This area is normally surrounded by ischemic tissue, referred to as the ischemic penumbra, that receives collateral circulation. Ischemia in the penumbra does not always result in irreversible damage. In some cases, restoration of blood flow (reperfusion) into the penumbra may prevent total ischemia and necrosis in this area. However, reperfusion has also been associated with injury to the tissue surrounding the core. Once blood flow is returned, blood cells such as neutrophils, attack the damaged tissue which can cause additional inflammation and/or damage. Reperfusion injury is associated with an influx of neutrophils into the affected tissue and subsequent activation of the neutrophils. Neutrophils can release lytic enzymes that directly induce tissue damage and proinflammatory mediators such as cytokines that amplify local inflammatory reaction. The influx of neutrophils to a site of ischemic damage can also plug capillaries and cause vasoconstriction. It has been found that kallikrein plays a role in neutrophil chemotaxis, neutrophil activation and reperfusion injury. Thus, the kallikrein inhibitors described herein can be used to prevent or reduce reperfusion injury, e.g., by reducing or preventing one or more of: 1) neutrophil infiltration, 2) neutrophil activation; 3) cytokine release; 4) elastase release; and 5) vasodilation. For example, a kallikrein inhibitor can be used to inhibit bradykinin and Factor XII.

Administration

A kallikrein inhibitor can be administered to a patient before, during, and/or after an ischemia event, e.g., a surgical procedure or cerebral ischemic attack, in a pharmaceutically acceptable composition or in connection with another disorder or event described herein. The patient is generally a human, but may also be a non-human mammal. Human patients include adults, e.g., patients between ages 19-25, 26-40, 41-55, 56-75, and 76 and older, and pediatric patients, e.g., patients between ages 0-2, 3-6, 7-12, and 13-18.

The term "pharmaceutically acceptable" composition refers to a non-toxic carrier or excipient that may be administered to a patient, together with a kallikrein inhibitor described herein. The carrier or excipient is chosen to be compatible with the biological or pharmacological activity of the composition. The inhibitors described herein can be administered locally or systemically by any suitable means for delivery of a kallikrein inhibitory amount of the inhibitor to a patient including but not limited to systemic administrations such as, for example, intravenous and inhalation. Parenteral administration is particularly preferred.

For parenteral administration, the polypeptides can be injected intravenously, intramuscularly, intraperitoneally, or subcutaneously. Intravenous administration is preferred. Typically, compositions for intravenous administration are solutions in sterile isotonic aqueous buffer. Other pharmaceutically acceptable carriers include, but are not limited to, sterile water, saline solution, and buffered saline (including buffers like phosphate or acetate), alcohol, vegetable oils, polyethylene glycols, gelatin, lactose, amylose, magnesium stearate, talc, silicic acid, paraffin, etc. Where necessary, the composition can also include a solubilizing agent and a local anaesthetic such as lidocaine to ease pain at the site of the injection, preservatives, stabilizers, wetting agents, emulsifiers, salts, lubricants, etc. as long as they do not react deleteriously with the active compounds. Similarly, the composition can comprise conventional excipients, e.g., pharmaceutically acceptable organic or inorganic carrier substances suitable for parenteral, enteral or intranasal application which do not deleteriously react with the active compounds. Generally, the ingredients will be supplied either separately or mixed together in unit dosage form, for example, as a dry lyophilized powder or water free concentrate in a hermetically sealed container such as an ampoule or sachette indicating the quantity of active agent in activity units. Where the composition is to be administered by infusion, it can be dispensed with an infusion bottle containing sterile pharmaceutical grade "water for injection" or saline. Where the composition is to be administered by injection, an ampoule of sterile water for injection or saline can be provided so that the ingredients can be mixed prior to administration.

In one embodiment, the inhibitor is administered to a patient as an intravenous infusion according to any approved procedure. For example, an inhibitor described herein can be administered to a patient subjected to a CABG procedure at the times similar to those currently used in approved protocols for administering aprotinin and in an amount necessary to provide a patient with a required number or concentration of kallikrein inhibitory units (KIU).

An inhibitor described herein can also be administered to a patient in the immediate postoperative period, when bleeding abnormalities can occur as a consequence of downstream effects of SIR. For example, in a procedure involving CPB, an inhibitor described herein can be administered to a patient as an initial loading dose, e.g., an effective amount over the course of a convenient time, such as 10 minutes, prior to induction of anesthesia. Then, at induction of anesthesia, a second dose of the inhibitor can be injected into the CPB priming fluid ("pump prime volume"). The patient can then be placed on a continuous and controlled intravenous infusion dose for the duration of the surgical procedure, and after the procedure if indicated.

In other embodiments, an inhibitor can be administered after an ischemic event, e.g., after a stroke, e.g., 5, 10, 15, 30, 45 minutes, 1, 2, 3, 5, 10, 15, 20 hours or more after a stroke. Preferably, the inhibitor is administered within 12 to 60 hours, e.g., within 24 to 48 hours, after a stroke. In some embodiments, an inhibitor is administered after an ischemic event, e.g., after a stroke, but prior to reperfusion of the damaged tissue. In other embodiments, an inhibitor is administered during reperfusion or after reperfusion has begun. In yet another embodiment, an inhibitor is administered after reperfusion has occurred.

An effective amount of an inhibitor (e.g., a Kunitz domain polypeptide or other compound described herein) can be administered alone or in combination with another therapeutic for the treatment of cerebral ischemia and/or reperfusion injury associated with cerebral ischemia. An effective amount is an amount sufficient to reduce one or more symptoms associated with cerebral ischemia and/or reperfusion injury associated with cerebral ischemia which otherwise would have occurred in a subject experiencing a cerebral ischemia and/or reperfusion injury associated with cerebral ischemia absent the treatment. Several physiological parameters may be used to assess stroke and reperfusion injury associated with stroke including infarct size, regional cerebral blood flow, intracranial pressure, anterograde amnesia, retrograde amnesia, dementia, cognitive function and/or emotion, and cerebral edema, for example, as compared to pretreatment patient parameters, untreated stroke patients or stroke patients treated with the other therapeutic agent but not the combination with the inhibitor (e.g., the Kunitz domain polypeptide or other compound described herein).

With respect to an implementation in which DX-88 or a DX-88-related inhibitor is used, the affinity constant (Ki) of DX-88 is at least about 1000 times greater than aprotinin for kallikrein inhibition. Accordingly, the dose of DX-88 or an inhibitor of similar affinity could be at least about 10, 50, 100, 500, or 1000 times lower than aprotinin on a mole per mole basis. The dose could also be modulated as a function of the amount of kallikrein activated during an event (e.g., CPB), the specificity of the DX-88-kallikrein interaction in vivo, the concentration of kallikrein eliciting SIRS, and pharmacological distribution.

The total amount of circulating prekallikrein in plasma is reported to be approximately 50 g/mL or 500 nM. If all prekallikrein is activated, at least 500 nmoles/L of DX-88 can be used to inhibit kallikrein in a stoichiometric manner. An individual having 5 L of plasma would require a dose of 2500 nmoles DX-88, or approximately 18 mg based on the molecular weight of DX-88 of 7,054 Daltons. The dose can be reduced proportionally if not all of the prekallikrein is activated.

As the concentration of active kallikrein may have to rise above a certain level to contribute to increased fluid and blood loss post-operatively, in many cases, it is not necessary to inactivate all active kallikrein. DX-88 would be expected to be effective at a significantly lower dose compared to aprotinin on the basis of its higher affinity for kallikrein. A plasma level of 10 nM DX-88 would inhibit 99.6% of the kallikrein present at a plasma concentration of 1 nM (i.e., only 0.4 pM free kallikrein remaining), while only 24.5% of the activated kallikrein would be inhibited by 10 nM aprotinin. These values were calculated using the standard equilibrium equation that relates the Ki of the binding interaction to the relative concentration of enzyme (plasma kallikrein) and inhibitor (DX-88). Plasma levels of at least 3 µM aprotinin would be required to inhibit kallikrein to the same extent as 10 nM DX-88. In other words, the high affinity of DX-88 for kallikrein can allow for a rapid therapeutic effect without maintaining high plasma inhibitor levels.

DX-88 also has greater specificity for kallikrein inhibition compared to aprotinin in vitro. Therefore, proteases other than kallikrein that are inhibited by aprotinin may lower the effective concentration of the inhibitor, thereby increasing the amount of aprotinin needed for a therapeutic effect.

An initial clinical dose of DX-88 for patients undergoing CPB has been estimated from the recommended high dose regimen of aprotinin ($2 \times 10^6$ KIU). Aprotinin is administered in three stages of $2 \times 10^6$ KIU each, consisting of a loading dose, a pump priming dose and a continuous intravenous infusion during CPB. Aprotinin is reported to have a specific inhibitory activity of 7,143 KIU/mgv, determined using a dog blood pressure assay. Therefore, $2 \times 10^6$ KIU of aprotinin is equivalent to 280 mg of the protein. In a patient having a plasma volume of 5 liters, 280 mg corresponds to approximately 8.6 µM aprotinin. The specific activity of aprotinin in the inhibitory assay used for DX-88 is approximately 0.5 KIU/mg determined using an enzymatic assay. A dose of 280 mg would correspond to a loading dose for aprotinin of approximately 140 KIU. The specific activity of DX-88 using the same assay is approximately 10 KIU/mg. A dose of only 14 mg of DX-88 would be required to provide a number of inhibitory units equivalent to 280 mg aprotinin. Thus, in certain embodiments, about 5-20, or 10-20 mg of DX-88 can be administered to a subject.

Administered "in combination," as used herein, means that two (or more) different treatments are delivered to the subject once the subject has been determined to be at risk for the disorder or during the course of the subject's affliction with the disorder, e.g., the two or more treatments are delivered after the subject has been diagnosed as at risk for the disorder or the two or more agents are delivered after the subject has been diagnosed with the disorder and before the disorder has been cured or eliminated. In some embodiments, the delivery of one treatment is still occurring when the delivery of the second begins, so that there is overlap. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered. The Kunitz domain polypeptide or other inhibitor can be administered before, concurrently with, or after the administration of another therapeutic, e.g., an anticoagulant agent, an antiplatelet agent or a thrombolytic agent.

Anticoagulation agents prevent the coagulation of blood components and thus prevent clot formation. Anticoagulants include, but are not limited to, heparin, warfarin, coumadin, dicumarol, phenprocoumon, acenocoumarol, ethyl biscoumacetate, hirudin, bivalarutin, and other direct thrombin inhibitors, and indandione derivatives.

Anti-platelet agents inhibit platelet aggregation and are often used to prevent thromboembolic stroke in patients who have experienced a transient ischemic attack or stroke. Anti-platelet agents include, but are not limited to, aspirin, thienopyridine derivatives such as ticlopodine and clopidogrel, dipyridamole and sulfinpyrazone, as well as RGD mimetics.

Thrombolytic agents lyse clots that cause the thromboembolic stroke. Thrombolytic agents have been used in the treatment of acute venous thromboembolism and pulmonary emboli and are well known in the art (e.g. see Hennekens et al, J Am Coll Cardiol; v. 25 (7 supp), p. 18S-22S (1995); Holmes, et al, J Am Coll Cardiol; v.25 (7 supply, p. 10S-17S (1995)). Thrombolytic agents include, but are not limited to, plasminogen, a2-antiplasmin, streptokinase, antistreplase, TNK, tissue plasminogen activator (tPA), and urokinase. "tPA" as used herein includes native tPA and recombinant tPA, as well as modified forms of tPA that retain the enzymatic or fibrinolytic activities of native tPA. The enzymatic activity of tPA can be measured by assessing the ability of the molecule to convert plasminogen to plasmin. The fibrinolytic activity of tPA may be determined by any in vitro clot lysis activity known in the art, such as the purified clot lysis assay described by Carlson, et al., Anal. Biochem. 168, 428-435 (1988) and its modified form described by Bennett, W. F. et al., 1991, supra.

Currently there are two regimens approved in the United States for administering aprotinin to a patient undergoing a CABG procedure (see, product label and insert for TRASYLOL™, Bayer Corporation Pharmaceutical Division, West Haven, Conn.). One such approved regimen uses a 2 million KIU intravenous loading dose, 2 million KILT into the pump prime volume, and 500,000 KIU per hour of surgery. Another approved regimen uses 1 million KIU intravenous loading dose, 1 million KIU into the pump prime volume, and 250,000 KIU Upper hour of surgery. As these regimens are based on KILL, the regimens are readily adapted to other kallikrein inhibitors described herein once the specific activity and KIU of a particular inhibitor has been determined by standard assays. Owing to the enhanced binding affinity and inhibitory activity in representative polypeptide inhibitors of kallikrein described herein relative to aprotinin, it is expected that the compositions and methods described herein are likely to require fewer milligrams (mg) per patient to provide a patient with the required number or concentration of KIU.

Several considerations regarding dosing with a polypeptide inhibitor of kallikrein can be illustrated by way of example with the representative PEP-I KI polypeptide having the amino sequence of SEQ ID NO:2 (molecular weight of 7,054 Daltons).

Table 1, below, provides a comparison of the affinity (Ki, app) of the PEP-1 KI polypeptide for kallikrein and eleven other known plasma proteases.

TABLE 1

| Protease Substrate | PEP-1 $K_i$, app (pM) | Aprotinin $K_i$, app (pM) |
|---|---|---|
| human plasma kallikrein | 44 | $3.0 \times 10^4$ |
| human urine kallikrein | $>1 \times 10^8$ | $4.0 \times 10^3$ |
| porcine pancreatic kallikrein | $2.7 \times 10^7$ | 550 |
| human C1r, activated | $>2.0 \times 10^8$ | $>1.0 \times 10^7$ |
| human C1s, activated | $>2.0 \times 10^7$ | $>1.0 \times 10^8$ |
| human plasma factor XIa | $1.0 \times 10^4$ | ND |
| human plasma factor XIIa | $>2.0 \times 10^7$ | $>1.0 \times 10^8$ |
| human plasmin | $1.4 \times 10^5$ | 894 |
| human pancreatic trypsin | $>2 \times 10^7$ | ND |
| human pancreatic chymotrypsin | $>2.0 \times 10^7$ | $7.3 \times 10^3$ |
| human neutrophil elastase | $>2.0 \times 10^7$ | $1.7 \times 10^3$ |
| human plasma thrombin | $>2.0 \times 10^7$ | $>1.0 \times 10^8$ |

ND = not determined

Clearly, the PEP-1 KI polypeptide is highly specific for human plasma kallikrein. Furthermore, the affinity ($K_i$,app) of PEP-1 for kallikrein is 1000 times higher than the affinity of aprotinin for kallikrein: the $K_i$,app of PEP-1 for kallikrein is about 44 pM (Table 1), whereas the $K_i$,app of aprotinin for kallikrein is 30,000 pM. Thus, a dose of PEP-1 could be approximately 1000 times lower than that used for aprotinin on a per mole basis. However, consideration of several other factors may provide a more accurate estimation of the dose of PEP-1 required in practice. Such factors include the amount of kallikrein activated during CPB in a particular patient, the concentration of kallikrein required to elicit an SIR, and the bioavailability and pharmacological distribution of PEP-1 in a patient. Nevertheless, use of a polypeptide that includes a Kunitz domain that inhibits kallikrein in doses currently approved for the use of aprotinin is still expected to provide significant improvements over the current use of the less specific, lower affinity, bovine aprotinin. Accordingly, lower doses, e.g., at least half, or a tenth of the approved aprotinin dose may be used for a kallikrein inhibitor which inhibits kallikrein at least 2, 10, 50, or 100 fold better than aprotinin.

For example, the total amount of circulating prekallikrein in plasma is estimated at approximately 500 nM (Silverberg, M. et al., "The Contact System and Its Disorders," in Blood: Principles and Practice of Hematology, Handin, R. et al., eds., J B Lippincott Co., Philadelphia, 1995). If all of the prekallikrein were activated, then at least 500 nM of PEP-1 would be required for a stoichiometric inhibition of kallikrein. An individual having 5 liters of plasma would therefore require about 18 mg of PEP-1 to achieve a plasma concentration of 500 nM.

Another factor to consider is the threshold concentration of kallikrein required to induce a SIR in a patient. If the concentration of active kallikrein must be maintained below, e.g., 1 nM, then owing to its high affinity for kallikrein, PEP-1 offers a significant advantage over aprotinin in the amount of protein that would be required to inhibit SIR. In particular, a concentration of PEP-1 of 1 nM would inhibit 99.6% of kallikrein present at 1 nM (i.e., only 0.4 pM free kallikrein remaining in the blood), whereas, an aprotinin concentration of 1 nM would only inhibit 24.5% of the kallikrein present at 1 nM. For aprotinin to inhibit 99% of the kallikrein at 1 nM, an aprotinin concentration in the plasma of at least 3 uM is required (i.e., 3000 times higher concentration than for PEP-1).

For a patient undergoing CPB, an initial clinical dose of PEP-1 can be estimated from a recommended dose regimen of aprotinin ($1 \times 10^6$ KIU) mentioned above. Aprotinin is reported in a package insert to have as specific inhibitory activity of 7143 KIU/mg determined using a dog blood pressure assay. Therefore, $1 \times 10^6$ KIU of aprotinin is equivalent to 140 mg of aprotinin (i.e., $1 \times 10^6$ KIU/7143 KIU/mg=140 mg of aprotinin). In a patient having a blood plasma volume of 5 liters, 140 mg corresponds to approximately 4.3 μM aprotinin (molecular weight of aprotinin is 6512 Daltons). The specific activity of aprotinin in the standard inhibitory assay used for PEP-1 is 0.4 KIU/mg of polypeptide. A dose of 140 mg would correspond to a loading dose for aprotinin of 56 KIU (140 mg×0.4 KIU/mg=56 KIU). In contrast, since the specific activity of the PEP-1 KI polypeptide is 10 KIU/mg in the standard inhibition assay, a dose of only 5.6 mg of PEP-1 would be required to provide the number of KIUs equivalent to 140 mg of aprotinin. In a patient with a plasma volume of 5 liters, this corresponds to about 160 nM PEP-1 (molecular weight of PEP-1 is 7054 Daltons), although a higher dose of the PEP-1 KI polypeptide can be required if all of the plasma kallikrein (500 nM) is activated and/or if this KI polypeptide is poorly distributed in a patient.

In some embodiment, the Kunitz domain polypeptide or KI polypeptide is administered in a dose of about 1-500 mg/m², preferably about 1-250 mg/m², 1-100 mg/m². For example, a KI polypeptide, e.g., a KI polypeptide described herein, can be administered to a subject at risk for cerebral ischemia, suffering from cerebrial ischemia, or who has suffered a cerebral ischemic attack at a dose of 1-100 mg/m².

Furthermore, the KI polypeptides can be non-naturally occurring, and they can be produced synthetically or recombinantly, as noted above, thereby avoiding potential contamination of transmissible diseases that can arise during isolation of a protein from a natural animal source, such as in the case of aprotinin, which is isolated from bovine lung. Increasingly important to administrative and public acceptance of a treatment or pharmaceutical composition comprising a polypeptide is the avoidance of possible contamination with and transmission to human patients of various pathological agents. Of particular interest for the safety of proteins isolated from a bovine tissue is the elimination of the possible risk of exposure to viral mediated diseases, bacterial mediated diseases, and, especially, transmissible bovine spongiform encephalopathies.

As variants of the Kunitz domain 1 of the human LACI protein, fewer side effects are expected from administering the KI polypeptides to patients than for aprotinin, which is a bovine protein that is documented to cause anaphylactic and anaphylactoid responses in patients, especially in repeat administrations, such as second time CABG procedures. Additionally, the highly specific binding of the KI polypeptides described herein to kallikrein will effectively limit or eliminate the thrombotic tendencies observed with aprotinin, and reduce the problems observed with graft patency following CABG procedures.

The invention will be further described with reference to the following non-limiting examples. The teachings of all the patents, patent applications and all other publications and websites cited herein are incorporated by reference in their entirety.

EXAMPLES

Example 1

An Exemplary Kallikrein Inhibitor Polypeptide

An exemplary non-naturally occurring, KI polypeptide (PEP-1) was identified as a kallikrein binding polypeptide displayed on a recombinant phage from a phage display library. PEP-1 has the amino acid sequence:

```
                                           (SEQ ID NO: 2)
Glu Ala Met His Ser Phe Cys Ala Phe Lys Ala Asp

Asp Gly Pro Cys Arg Ala Ala His Pro Arg Trp Phe

Phe Asn Ile Phe Thr Arg Gln Cys Glu Glu Phe Ile

Tyr Gly Gly Cys Glu Gly Asn Gln Asn Arg Phe Glu

Ser Leu Glu Glu Cys Lys Lys Met Cys Thr Arg Asp
```

The molecular weight of PEP-1 is 7,054 Daltons.

The nucleotide sequence (SEQ ID NO:3) of the recombinant phage DNA encoding the PEP-1 amino acid sequence (amino acids 1-60 of SEQ ID NO: 2) was isolated and sequenced by standard methods determined from the recombinant phage DNA.

PEP-1 was produced in amounts useful for further characterization as a recombinant protein in His4⁻ phenotype host cells of yeast strain *Pichia pastoris*.

Example 2

Construction of a Recombinant Plasmid to Express KI Polypeptides

The initial plasmid, pHIL-D2, was ampicillin resistant and contained a wild type His4 of *P. pastoris*. The final DNA sequence comprising the coding sequence for the matα Prepro-PEP-1 fusion protein in the recombinant expression plasmid pPIC-K503 is shown in FIG. 2. The DNA sequence of pHIL-D2 was modified to produce pPIC-K503, as follows:

1. The BstBI site in the 3' AOX1 region of pHIL-D2, located downstream of the His4 gene, was removed by partial restriction digestion, fill-in, and ligation, altering the sequence from TTCGAA (SEQ ID NO:23) to TTCGCGAA (SEQ ID NO:24). This modification was made in order to facilitate and direct the cloning of the expression cassette into the plasmid.

2. The AatII site bear the bla gene located downstream of His4 was removed by restriction digestion, fill-in, and ligation modifying the sequence from GACGTC (SEQ ID NO:25) to GACGTACGTC (SEQ ID NO:26). This modification was made to facilitate the cloning of expression cassettes having AatII sites into the plasmid.

The DNA encoding PEP-1 was synthesized based on the nucleotide sequence from the original, kallikrein binding, display phage and consisted of 450 base pairs (bp). The final DNA sequence of the insert in the pHIL-D2 plasmid would be flanked by a 5' AOX1 sequence and a 3' AOX1 sequence (portions of which are shown in FIG. 2) and encode a fusion protein comprising the matα Prepro signal peptide of *S. cerevisiae* fused to the structural coding sequence for the PEP-1 KI polypeptide. The signal peptide was added to facilitate the secretion of PEP-1 from the yeast host cells. The oligonucleotides to form the insert were synthesized and obtained commercially (Genesis Labs, The Woodlands, Tex.) and linked by polymerase chain reaction (PCR). The linked synthetic DNA encoding the matα Prepro-PEP-1 fusion protein was then incorporated by ligation into the modified pHIL-D2 plasmid between the BstBI and EcoRI sites.

The ligation products were used to transform *Escherichia coli* strain XL1 Blue, A PCR assay was used to screen *E. coli* transformants for the desired plasmid construct. DNA from cell extracts was amplified by PCR using primers containing the 5'AOX1 and 3'AOX1 sequences (see above and FIG. 2). PCR products of the correct number of base pairs were sequenced. Approximately 20-50 bp on either side of the cloning sites, in addition to the insert, were sequenced, and the expected sequence was obtained. The final DNA sequence of the insert in the pHIL-D2 plasmid (to yield plasmid pPIC-K503) is shown in FIG. 2 along with portions of flanking 5' and 3' AOX1 sequences (SEQ ID NO:27) and corresponding amino acid sequence of the fusion protein comprising the matα Prepro signal peptide of *S. cerevisiae* fused to the structural coding sequence for the PEP-1 KI polypeptide (SEQ ID NO:28). A transformant with the desired expression plasmid construct, plasmid pPIC-K503, was selected for preparing yeast cell lines for routine production of PEP-1.

Example 3

Manufacture of Pep-1 from Recombinant Yeast Cell Line

Spheroplasts of *P. pastoris* GS115 having the His4⁻ phenotype were transformed with the expression plasmid pPIC- K503 (above) following linearization of the plasmid at the SacI site and homologous recombination of the plasmid DNA into the host 5'AOX1 locus. The phenotype of the production strain is His4+. The entire plasmid was inserted into the 5'AOX1 genomic sequence of the yeast.

Isolates from the transformation were screened for growth in the absence of exogenous histidine with methanol as the sole carbon source. Greater than 95% of the transformants retained the wild type ability to grow with methanol as the sole carbon source, demonstrating that the plasmid had been inserted into the host genome by homologous recombination rather than transplacement, and did not require exogenous histidine for growth, demonstrating that the plasmid was integrated into the host genome. Selected colonies were cloned. Small culture expression studies were performed to identify clones secreting the highest levels of active PEP-1 into the culture medium. PEP-1 secretion levels in clarified culture supernatant solutions were quantified for PEP-1 levels by sodium dodecyl sulfate polyacrylamide gel electrophoresis (SDS-PAGE) and evaluated for kallikrein inhibition. A yeast clone was selected for PEP-I production based on its high level of PEP-1 expression among cultures sampled.

Master and working cell banks of PEP-1 producing *P. pastoris* were prepared commercially, MDS Pharma Services, Bothell, Wash.). A standard production of PEP-1 in yeast comprised three steps: (1) preparation of the seed culture, (2) fermentation, and (3) recovery of the culture.

The seed culture step consisted of the inoculation of six flasks (300 ml) containing sterile inoculum broth (yeast nitrogen base, potassium phosphate, and glycerol, pH 5) with the contents of a single vial of a working cell bank of PEP-1 producing *P. pastoris*. Flasks were inoculated in an orbital shaker (300 rpm) for approximately 13 hours at 30° C.±2° C.

Fermentations were performed in a closed 100 liter Braun fermenter filled with sterile broth. Each fermentation was initiated with the transfer of the contents of the six seed culture flasks to the fermenter. After approximately 24 hours, the glycerol in the fermenter became exhausted and additional glycerol was added for approximately 8 additional hours.

A mixed feed phase, which lasted approximately 83 hours, was then initiated by the addition of a glycerol and methanol feed. At the end of this time, the fermentation was terminated, and the fermenter contents were diluted with purified water.

The purification and processing of PEP-1 consisted of five steps: (1) expanded bed chromatography, (2) cation exchange chromatography, (3) hydrophobic interaction chromatography (HIC), (4) ultrafiltration and diafiltration, and (5) final filtration and packaging.

The initial purification step consisted of expanded bed chromatography. The diluted fermenter culture was applied to the equilibrated column packed with Streamline SP resin (Amersham Pharmacia Streamline 200 chromatography column, Amersham Pharmacia, Piscataway, N.J.). The diluted fermenter culture was applied to the equilibrated column. The column was then washed (50 mM acetic acid, pH 3.0-3.5) in an up-flow mode to flush the yeast cells from the expanded bed. The top adaptor was raised above the expanded bed enhance washing. The flow was stopped and the bed was allowed to settle. The adaptor was moved down so that it was slightly above the settled bed. The direction of the flow was reversed. The effluent was collected. Washing was continued in a downward mode using 50 mM sodium acetate, pH 4.0. The effluent was collected. PEP-1 was eluted from the column using 50 mM sodium acetate, pH 6.0. The eluate was collected in a 50 liter container. The eluate was then filtered through a 0.22µ filter into a clean container located in the purification site. Additional samples were collected for the determination of PEP-1 concentration.

A cation exchange chromatography step was then performed using the filtered eluate from the expanded bed column. PEP-1 eluted from the column using 15 mM trisodium citrate, pH 6.2.

Additional proteins were removed from the PEP-1 preparation by hydrophobic interaction chromatography (HIC). Prior to HIC, the eluate from the cation exchange column was diluted with ammonium sulfate. The eluate was applied to the column, and the PEP-1 was eluted using ammonium sulfate (0.572 M) in potassium phosphate (100 mM), pH 7.0. The eluate was collected in fractions based on $A_{280}$ values. All fractions were collected into sterile, pre-weighed PETG bottles.

Selected fractions were pooled into a clean container. The pool was concentrated by ultrafiltration. The concentrated PEP-1 preparation was immediately diafiltered against ten volumes of PBS, pH 7.0.

A final filtration step was performed prior to packaging in order to minimize the bioburden in the bulk PEP-1. The bulk solution was filtered through a 22µ filter and collected into a sterile, pre-weighed PETG bottle. A sample was removed for lot release testing. The remainder of the bulk was dispensed aseptically into sterile PETG bottles and stored at −20° C.

Example 4

Kallikrein Inhibition Assay

The potency assay of KI polypeptides, such as PEP-1, described herein was a kinetic test, which measured fluorescence generation following the kallikrein-mediated cleavage of a substrate, prolylphenylalanylarginyl amino methyl coumarin. A known amount of kallikrein was incubated with buffer, with a serially diluted KI polypeptide reference standard, or serially diluted KI polypeptide test samples. Each sample was run in triplicate. The substrate solution was added, and the plate read immediately using an excitation wavelength of 360 nm and an emission wavelength of 460 nm. At least two each of the reference standard and sample curves were required to have an R-squared value of ≥0.95 to be considered valid.

Example 5

Neuroprotective Effect of Kallikrein Inhibitor Polypeptide at Various Doses on Brain Ischemia/Reperfusion Injury The presence of tissue kallikrein in the brain and the identification of bradykinin B2 receptors on brain cells suggest that kinin system could play a role in the nervous system pathophysiology. Recent data showing the effectiveness of bradykinin B2 receptor antagonists in reducing ischemic brain damage further supports such a hypothesis.

In this example, a kallikrein inhibitor polypeptide (DX-88) is effective in reducing neurological deficits and brain injury after transient focal brain ischemia.

In vitro analysis was performed to determine whether DX-88 was able to cross the blood-brain barrier. Non-ischemic mice were treated iv with saline or DX-88 (10 µg/mouse or 30 µg/mouse) and plasma was drawn 30 or 60 min after administration. Thirty minutes after DX-88 treatment, plasma kallikrein inhibitory activity was 2 and 4 times higher in mice treated with 30 and 10 µg, respectively. Such a difference was not seen in plasma drawn 60 min after the infusion. In cerebral spinal fluid (CSF) from mice treated with 30 µg of DX-88, there was marked inhibitory activity with no difference between CSF drawn 30 or 60 min after DX-88 administration.

Isehemia was induced by occlusion of the middle cerebral artery (MCAO). At the end of the ischemic period (30 min), the filament was removed and reperfusion allowed. Mice received different doses of DX-88 iv at the beginning of the ischemic period. Twenty four hours after ischemia, neurological deficits and infarct size were evaluated. While saline treated mice showed stable scores, those who received 30 mg of DX-88 had significantly reduced general (13 and 10.5, median of saline and DX-88 treated mice, respectively) and focal (26 and 15.5, median of saline and DX-88 treated mice, respectively) deficits scores. In these mice the ischemic volume was also significantly reduced ($22.86 \pm 5.82$ mm$^3$, $23.04 \pm 4.34$ mm$^3$ respectively) compared to saline treated mice ($63.12 \pm 7.69$ mm$^3$). This study shows that: i) DX-88, in its active form, can cross rapidly the intact blood-brain barrier and thus reach brain tissue; ii) DX-88 has a significant neuroprotective effect against adverse consequences of brain ischemia and reperfusion injury.

Example 6

Neuroprotective Effect of Kallikrein Inhibitor Polypeptide Administered at Different Times During Brain Ischemia and Reperfusion Injury Ischemia was induced by occlusion of the middle cerebral artery by MCAO using a 6-0 monofilament. At the end of the 30 min ischemic period, the filament was removed and reperfusion allowed. Mice received DX-88 iv at the beginning of the ischemic period or at the end of it, during reperfusion.

It was first analyzed whether DX-88 was able to cross the blood-brain barrier and found that thirty minutes after treatment with 30 µg/mouse iv, a marked inhibitory activity was present in CSF. The same dose of DX-88 was given at the beginning of ischemic period. Twenty four hours after ischemia, neurological deficits and infarct size were evaluated. While saline treated mice showed stable scores, those who received of DX-88 had significantly reduced general (by 37.5%) and focal (by 50.0%) deficits scores. In these mice the ischemic volume was also significantly reduced by 50.9%. When given at reperfusion, DX-88 was similarly effective in improving general (by 38%) and focal (by 50.1%) deficits scores as well as the ischemic volume that was reduced by 58%.

This study shows that: i) this specific kallikrein inhibitor can cross rapidly the intact blood-brain barrier and thus possibly reach brain tissue in its active form; ii) it has a significant neuroprotective effect against adverse consequences of brain ischemia and reperfusion injury.

Other variations and embodiments of the invention described herein will now be apparent to those of ordinary skill in the art without departing from the scope of the invention or the spirit of the claims below.

What is claimed:

1. A method for reducing reperfusion injury in a patient the method comprising: administering to the patient a composition comprising an inhibitor of plasma kallikrein, in an amount effective to prevent or reduce neurocognitive defects due to reperfusion injury and/or damage to the central nervous system, wherein the inhibitor of plasma kallikrein comprises the amino acid sequence: Xaa1 Xaa2 Xaa3 Xaa4 Cys Xaa6 Xaa7 Xaa8 Xaa9 Xaa10 Xaa11 Gly Xaa13 Cys Xaa15 Xaa16 Xaa17 Xaa18 Xaa19 Xaa20 Xaa21 Xaa22 Xaa23 Xaa24 Xaa25 Xaa26 Xaa27 Xaa28 Xaa29 Cys Xaa31 Xaa32 Phe Xaa34 Xaa35 Gly Gly Cys Xaa39 Xaa40 Xaa41 Xaa42 Xaa43 Xaa44 Xaa45 Xaa46 Xaa47 Xaa48 Xaa49 Xaa50 Cys Xaa52 Xaa53 Xaa54 Cys Xaa56 Xaa57 Xaa58 (SEQ ID NO. 1), wherein Xaa1, Xaa2, Xaa3, Xaa4, Xaa56, Xaa57 or Xaa58 are each individually an amino acid or absent;

Xaa10 is Asp;
Xaa11 is Asp;
Xaa13 is Pro;
Xaa15 is Arg;
Xaa16 is Ala;
Xaa17 Ala;
Xaa18 is His;
Xaa19 is Pro;
Xaa21 is Trp;
Xaa22 is an amino acid selected from the group consisting of: Tyr and Phe;
Xaa23 is an amino acid selected from the group consisting of: Tyr and Phe;
Xaa31 is Glu;
Xaa32 is Glu;
Xaa34 is Ile;
Xaa35 is Tyr;
Xaa39 is Glu;
Xaa40 is an amino acid selected from the group consisting of: Gly and Ala;
Xaa43 is an amino acid selected from the group consisting of: Asn and Gly; and
Xaa45 is an amino acid selected from the group consisting of: Phe and Tyr.

2. The method of claim 1, wherein the reperfusion injury is reperfusion injury associated with cerebral ischemia.

3. The method of claim 2, wherein the cerebral ischemia is a stroke.

4. The method of claim 3, wherein the stroke is selected from the group consisting of an embolism associated stroke, a thrombus-associated stroke, a thromboembolitic stroke and a hemorrhage-associated stroke.

5. The method of claim 3, wherein the stroke is an embolism-associated stroke.

6. The method of claim 3, wherein the stroke is a thrombus-associated stroke.

7. The method of claim 6, wherein the thrombus-associated stroke is a perioperative stroke.

* * * * *